(12) United States Patent
Mazitschek et al.

(10) Patent No.: US 11,596,691 B2
(45) Date of Patent: *Mar. 7, 2023

(54) PHOTOSWITCHABLE HDAC INHIBITORS

(71) Applicant: The General Hospital Corporation, Boston, MA (US)

(72) Inventors: Ralph Mazitschek, Belmont, MA (US); Balaram Ghosh, Boston, MA (US); James Adam Hendricks, Watertown, MA (US); Surya Reis, Boston, MA (US); Stephen John Haggarty, Dorchester, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/091,863

(22) Filed: Nov. 6, 2020

(65) Prior Publication Data
US 2021/0162048 A1 Jun. 3, 2021

Related U.S. Application Data

(63) Continuation of application No. 15/968,634, filed on May 1, 2018, now Pat. No. 10,828,367, which is a continuation of application No. 14/775,340, filed as application No. PCT/US2014/026069 on Mar. 13, 2014, now Pat. No. 9,981,038.

(60) Provisional application No. 61/780,373, filed on Mar. 13, 2013.

(51) Int. Cl.
| | | |
|---|---|---|
| C07D 333/20 | (2006.01) |
| C07D 409/14 | (2006.01) |
| C07D 491/16 | (2006.01) |
| C07F 5/02 | (2006.01) |
| C07C 259/06 | (2006.01) |
| C07C 245/08 | (2006.01) |
| C07C 259/10 | (2006.01) |
| A61K 41/00 | (2020.01) |

(52) U.S. Cl.
CPC ........ *A61K 41/0028* (2013.01); *C07C 245/08* (2013.01); *C07C 259/06* (2013.01); *C07C 259/10* (2013.01); *C07D 333/20* (2013.01); *C07D 409/14* (2013.01); *C07D 491/16* (2013.01); *C07F 5/022* (2013.01)

(58) Field of Classification Search
None
See application file for complete search history.

(56) References Cited

U.S. PATENT DOCUMENTS

| 4,522,811 A | 6/1985 | Eppstein et al. |
| 6,468,798 B1 | 10/2002 | Debs et al. |
| 7,674,627 B2 | 3/2010 | Corcoran et al. |
| 9,981,038 B2 | 5/2018 | Mazitschek et al. |
| 10,828,367 B2 | 11/2020 | Mazitschek et al. |
| 2002/0161050 A1 | 10/2002 | Purchase et al. |
| 2005/0113450 A1 | 5/2005 | Thorarensen et al. |

FOREIGN PATENT DOCUMENTS

| WO | WO 1987/05297 | 9/1987 |
| WO | WO 2004/058234 | 7/2004 |
| WO | WO 2005/030705 | 4/2005 |
| WO | WO 2009/055917 | 5/2009 |
| WO | WO 2014/160221 | 10/2014 |

OTHER PUBLICATIONS

Karlicek et al. "Darstellung und Eigenschaften von Azoverbindungen mit funktioneller Karbohydroxamgruppe" Chem. zvesti, 1981, vol. 35, No. 4, pp. 491-499.*
Bandara and Burdette, "Photoisomerization in different classes of azobenzene," Chem. Soc. Rev., 2012, 41:1809-1825.
Beharry and Woolley, "Azobenzene photoswitches for biomolecules," Chem. Soc. Rev. Aug. 2011, 40:4422-37.
Bowers et al., "Total synthesis and biological mode of action of largazole: a potent class I histone deacetylase inhibitor," J. Am. Chem. Soc., Aug. 2008, 130:11219-11222.
Bradner et al., "Chemical Phylogenetics of Histone Deacetylases," Nature Chemical Biology, Mar. 2010, 6:238-243.
Bressi et al., "Exploration of the HDAC2 foot pocket: Synthesis and SAR of substituted N-(2-aminophenyl) benzamides," Bioorg. Med. Chem. Lett., May 2010, 20:3142-3145.
Brieke et al., "Light-Controlled Tools," Angewandte Chemie International Edition, Aug. 2012, 51(34):8446-8476.
Copeland et al., "Drug-target residence time and its implications for lead optimization," Nat. Rev. Drug Discov., Sep. 2006, 5:730-739.
EP Extended European Search Report in International Appln. No. 14774678, dated Oct. 12, 2016, 7 pages.
EP Office Action in European Appln. No. 14774678, dated Apr. 17, 2020, 4 pages.
EP Office Action in European Appln. No. 14774678, dated Feb. 9, 2021, 8 pages.
Haggarty and Tsai, "Probing the Role of HDACs and Mechanisms of Chromatin-Mediated Neuroplasticity," Neurobiol. Learn Mem., Jul. 2011, 96(1):41-52.
International Preliminary Report on Patentability in International Appln. No. PCT/US2014/026069, dated Sep. 15, 2015, 8 pages.
International Search Report and Written Opinion in International Appln. No. PCT/US2014/026069, dated Aug. 28, 2014, 11 pages.
Marchion and Munster, "Development of Histone Deacetylase Inhibitors for Cancer Treatment," Expert Review of Anticancer Therapy, 2007, 7(4): 583-598.
Markin et al., "Synthesis and properties of azo reagents chemically bonded via a silica surface", Database Accession No. 106: 5122, 1985, 2 pages.
McNamara et al., "Water-stable, hydroxamate anchors for functionalization of Ti02 surfaces with ultrafast interfacial electron transfer," Energy & Environmental Science, Jan. 2010, 3: 917.
Methot et al., "Exploration of the internal cavity of histone deacetylase (HDAC) with selective HDAC1/HDAC2 inhibitors (SHI-1:2)," Bioorg. Med. Chem. Lett., 2008, 18(3):973-8.
Moradei et al., "Novel aminophenyl benzamide-type histone deacetylase inhibitors with enhanced potency and selectivity," J. Med. Chem., Nov. 2007, 50:5543-5546.

(Continued)

Primary Examiner — Joseph R Kosack
(74) Attorney, Agent, or Firm — Fish & Richardson P.C.

(57) ABSTRACT
This invention relates to photoswitchable inhibitors of histone deacetylases and methods of using the same.

3 Claims, 26 Drawing Sheets

(56) References Cited

OTHER PUBLICATIONS

Swinney, "Applications of Binding Kinetics to Drug Discovery," Pharmaceutical Medicine, Jan. 2008, 22:23-34.
Swinney, D. Part VI: Topics in Biology-18 Molecular Mechanism of Action (MMoA) in Drug Discovery; Annual Reports in Medicinal Chemistry, 2011.
Tessier et al., "Diphenylmethylene hydroxamic acids as selective class IIa histone deacetylase inhibitors," Bioorg. Med. Chem. Lett., Oct. 2009, 19:5684-5688.
Wang et al., "On the function of the 14 A long internal cavity of histone deacetylase-like protein: implications for the design of histone deacetylase inhibitors," Med. Chem., Jun. 2004, 47:3409-3417.
Witter et al., "Optimization of biaryl Selective HDAC1&2 Inhibitors (SHI-1:2)," Bioorg. Med Chem. Lett., 2008, 18:726-731.
Woolfork and Roberts, "p-Phenylazobenzoyl Chloride for Identification and Chromatographic Separation of Colorless Compounds. II. Amines," Journal of Organic Chemistry, 1956, 21(4):436-438.
Office Action in European Appln. No. 14774678.8, dated Jun. 9, 2022, 5 pages.
STN Accession No. 2003:255113, "US 20020161050A1—Benzenebutyric acids and their derivatives as inhibitors of matrix metalloproteinases—XP055926830," dated Jan. 1, 2002, 17 pages.

\* cited by examiner

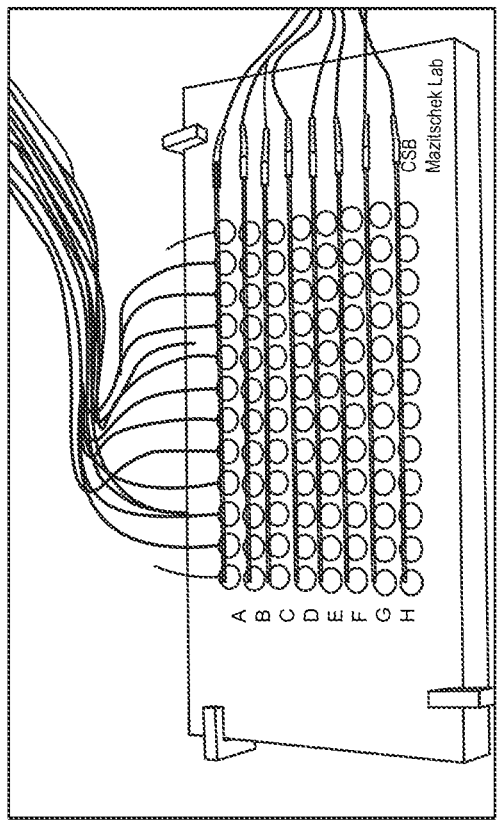
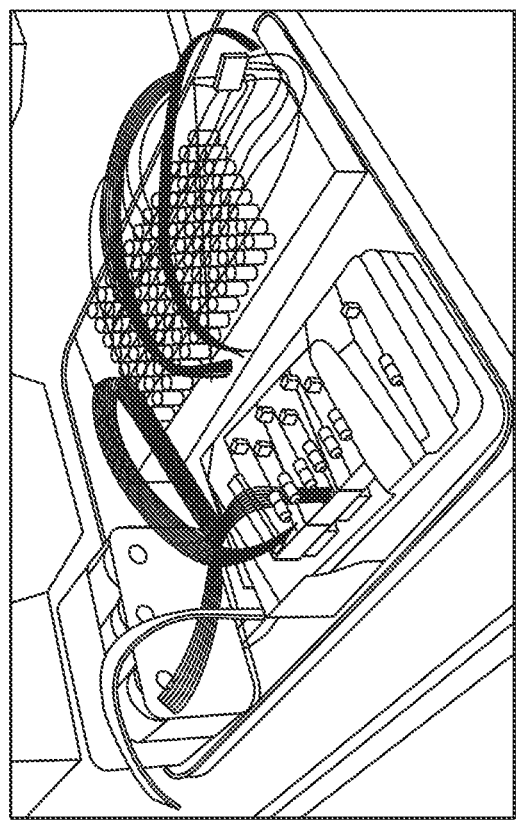
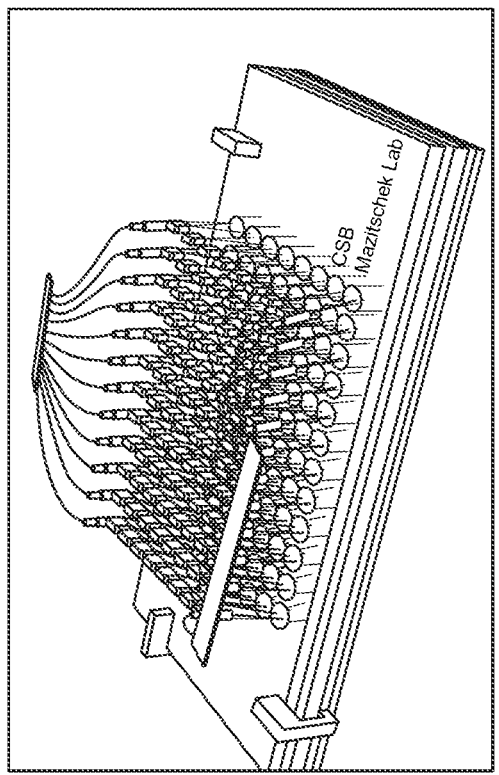
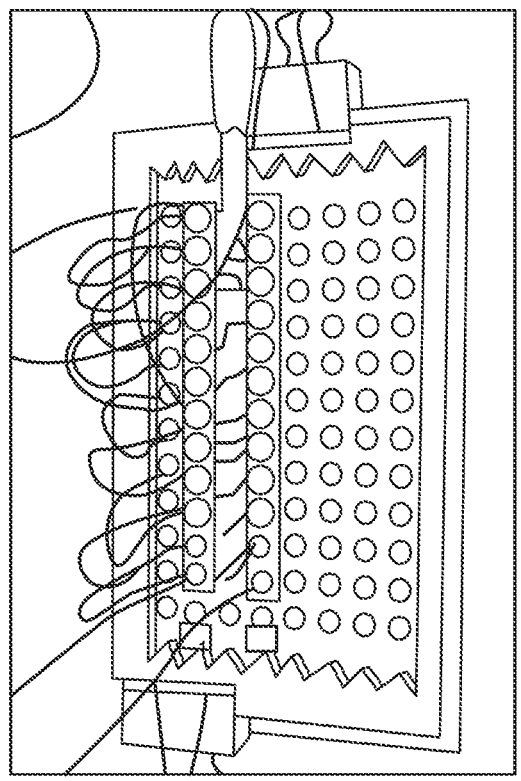
FIG. 4

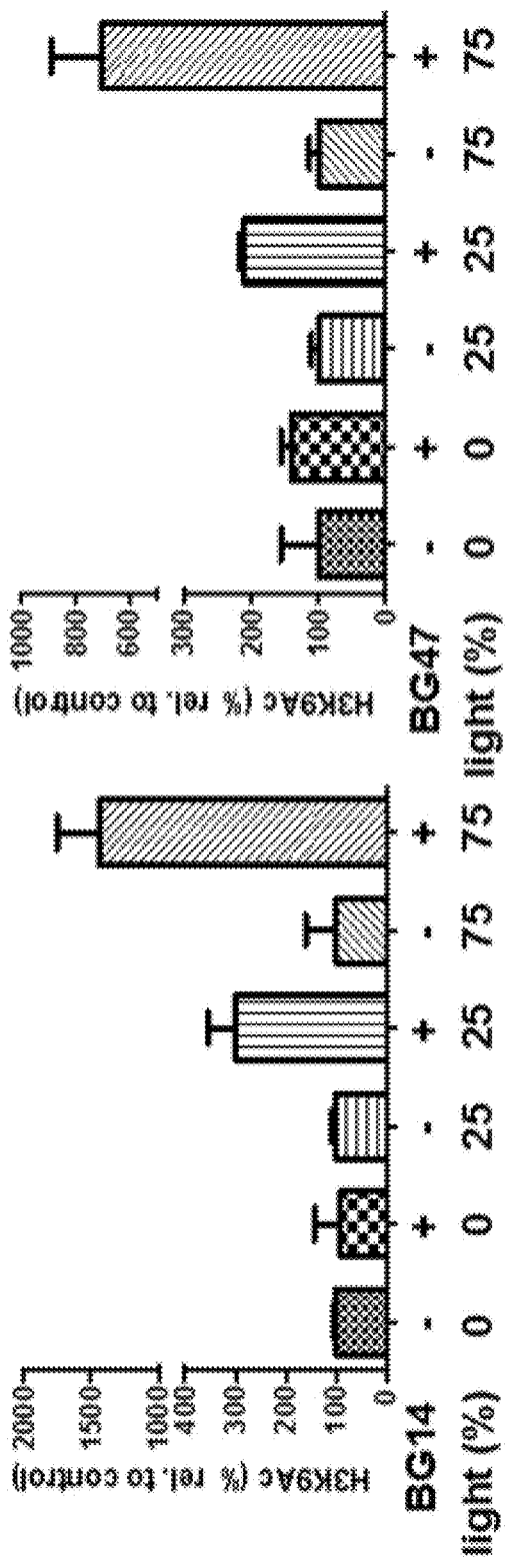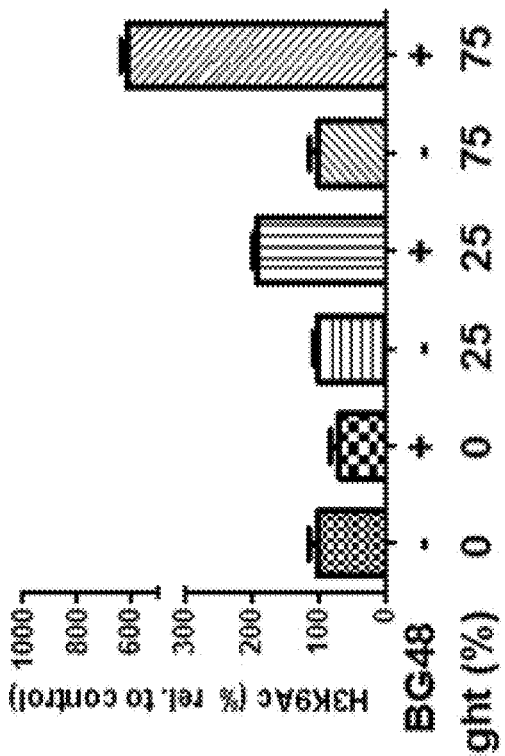

GeneMANIA Analysis of Core Gene Set

| Feature/Network | FDR | Genes in Network/Genome |
|---|---|---|
| Interphase of mitotic cell cycle | 3.27e-5 | 13 / 258 |
| Interphase | 3.27e-5 | 13 / 263 |
| S phase of mitotic cell cycle | 3.27e-5 | 10 / 132 |
| S phase | 3.94e-5 | 10 / 139 |
| G1/S transition of mitotic cell cycle | 3.94e-5 | 11 / 184 |
| cell cycle checkpoint | 3.26e-4 | 11 / 230 |
| positive regulation of release of cytochrome c from mitochondria | 1.09e-2 | 4 / 19 |
| regulation of mitochondrion organization | 1.19e-2 | 5 / 43 |
| positive regulation of mitochondrion organization | 2.69e-2 | 4 / 25 |
| regulation of release of cytochrome c from mitochondria | 3.86e-2 | 4 / 28 |

FIG. 15F

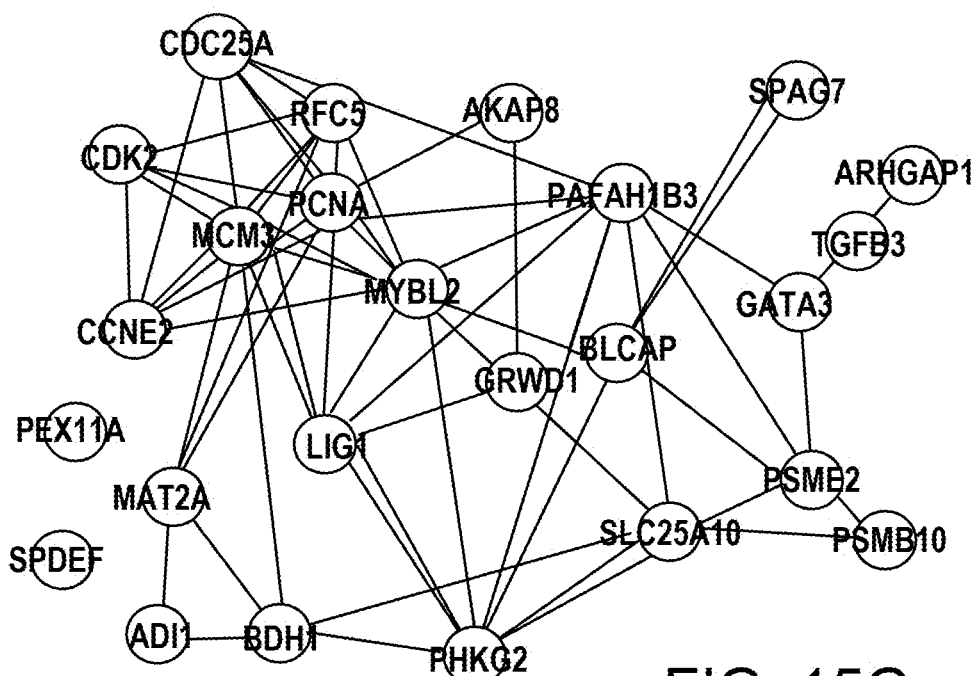

FIG. 15G

PHOTOSWITCHABLE HDAC INHIBITORS

CLAIM OF PRIORITY

This application is a continuation of U.S. patent application Ser. No. 15/968,634, filed May 1, 2018, which is a continuation of U.S. patent application Ser. No. 14/775,340, filed Sep. 11, 2015, now U.S. Pat. No. 9,981,038, which is a U.S. National Phase Application under 35 U.S.C. § 371 of International Patent Application No. PCT/US2014/026069, filed on Mar. 13, 2014, which claims the benefit of U.S. Provisional Application Ser. No. 61/780,373, filed on Mar. 13, 2013, all of which are incorporated herein by reference in its entirety.

FEDERALLY SPONSORED RESEARCH OR DEVELOPMENT

This invention was made with Government support under Grant Nos. R01DA028301, P50A086355, and T32-CA079443 awarded by the National Institutes of Health. The Government has certain rights in the invention.

TECHNICAL FIELD

This invention relates to photoswitchable inhibitors of histone deacetylases and methods of using the same.

BACKGROUND

Small molecule modulators of biomacromolecule function, in particular, receptors and enzymes, are widely used both as drugs to treat human diseases and as tool compounds to study biological processes. Importantly, small molecules enable scientific approaches that offer high spatial and temporal resolution, which can rarely be achieved with traditional molecular biological methods. However, when used in the context of larger biological settings such as organs or whole organisms, the spatiotemporal resolution of small molecules is limited and may be insufficient, resulting in side effects (when used as a drug) and indefinite experimental outcomes (when used as a tool). Thus, approaches that will provide an additional level of control with respect to time and space are highly desirable.

SUMMARY

Provided herein are inhibitors of histone deacetylases (HDACs) having photo-switchable modulators of protein function with short thermal relaxation kinetics. In some embodiments, the compounds provided herein are characterized as having a ground state, i.e. thermally relaxed, trans-isomer which is less active (e.g., inactive) compared to the excited state cis-isomer.

Provided herein is a compound of Formula (I):

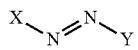

or a pharmaceutically acceptable salt thereof, wherein:
X and Y are independently a substituted or unsubstituted aryl or heteroaryl ring, wherein at least one of the rings is substituted with one or more HDAC targeting elements.

In some embodiments, Y is substituted with one or more HDAC targeting elements and X is substituted with one or more fluorescent moieties.

In some embodiments, a compound of Formula (I) is a compound of Formula (II):

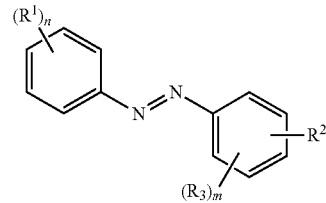

or a pharmaceutically acceptable salt thereof,
wherein:
each $R^1$ is independently selected from the group consisting of: hydrogen, $C_{1-6}$alkyl, $C_{2-6}$alkenyl, $C_{1-6}$alkynyl, halo, $C_{1-6}$ haloalkyl, CN, $NO_2$, $OR^4$, $SR^4$, $C(O)R^4$, $C(O)NR^4R^5$, $C(O)OR^4$, $OC(O)R^4$, $OC(O)NR^4R^5$, $C(=NR^4)NR^5R^6$, $NR^4C(=NR^5)NR^6R^7$, $NR^4R^5$, $NR^4C(O)R^5$, $NR^4C(O)OR^5$, $NR^4C(O)NR^5R^6$, $NR^4S(O)R^5$, $NR^4S(O)_2R^5$, $NR^4S(O)_2NR^5R^6$, $S(O)R^4$, $S(O)NR^4R^5$, $S(O)_2R^4$, $S(O)_2NR^4R^5$, $C_{1-6}$alkoxyalkyl, carbocyclyl, $C_{1-6}$carbocyclylalkyl, heterocyclyl, $C_{1-6}$heterocyclylalkyl, aryl, $C_{1-6}$aralkyl, heteroaryl, and $C_{1-6}$heteroaralkyl;
$R^2$ is an HDAC targeting element;
$R^3$ is independently selected from the group consisting of: $C_{1-6}$alkyl, $C_{2-6}$alkenyl, $C_{2-6}$alkynyl, halo, $C_{1-6}$ haloalkyl, CN, $NO_2$, $OR^4$, $SR^4$, $C(O)R^4$, $C(O)NR^4R^5$, $C(O)OR^4$, $OC(O)R^4$, $OC(O)NR^4R^5$, $C(=NR^4)NR^5R^6$, $NR^4C(=NR^5)NR^6R^7$, $NR^4R^5$, $NR^4C(O)R^5$, $NR^4C(O)OR^5$, $NR^4C(O)NR^5R^6$, $NR^4S(O)R^5$, $NR^4S(O)_2R^5$, $NR^4S(O)_2NR^5R^6$, $S(O)R^4$, $S(O)NR^4R^5$, $S(O)_2R^4$, $S(O)_2NR^4R^5$, $C_{1-6}$alkoxyalkyl, carbocyclyl, $C_{1-6}$carbocyclylalkyl, heterocyclyl, $C_{1-6}$heterocyclylalkyl, aryl, $C_{1-6}$aralkyl, heteroaryl, and $C_{1-6}$heteroaralkyl;
each $R^4$, $R^5$, and $R^6$ are independently selected from H and $C_{1-6}$alkyl;
m is an integer from 0 to 4; and
n is an integer from 1 to 5.

In some embodiments, $R^1$ is an electron withdrawing group. For example, $R^1$ can be independently selected from the group consisting of: $NR^5R^6$, $OR^5$, $SR^5$, $C_{1-6}$ alkyl, $CH=N-NR^5R^6$, $CH=C(NR^5R^6)_2$, $NR^5COR^6$, $NR^5C(O)NR^6R^7$, aryl, and heteroaryl; wherein each $R^5$, $R^6$, and $R^7$ is independently selected from H and $C_{1-6}$ alkyl. In some embodiments, n is 1 and $R^1$ is in the para position on the ring. In some embodiments, $R^1$ is $NR^5R^6$.

In some embodiments, m is 0 and $R^2$ is in the ortho position on the ring. In some embodiments, m is 1 and $R^2$ is in the ortho position and the $R^3$ is in the meta position across the ring from the first $R^2$.

In some embodiments, $R^1$ and/or $R^3$ can be independently selected from carbocyclyl, $C_{1-6}$carbocyclylalkyl, heterocyclyl, $C_{1-6}$heterocyclylalkyl, aryl, $C_{1-6}$aralkyl, heteroaryl, and $C_{1-6}$heteroaralkyl. For example, $R^1$ and/or $R^3$ can be independently selected from a substituted or unsubstituted tetrazine, a substituted or unsubstituted trans-cyclooctene, and a substituted or unsubstituted cyclopropene.

In some embodiments, the HDAC targeting element is selected from the group consisting of: a substituted or unsubstituted aminobenzamide, a substituted or unsubstituted hydroxybenzamide, and hydroxamic acids. For example, the HDAC targeting element is selected from the group consisting of: CI-994, Entinostat (MS-275), HDAC1/2 selective CI-994 analog, Mocetinostat (MGCD0103), and analogs thereof.

Also provided herein is a compound of Formula (IV):

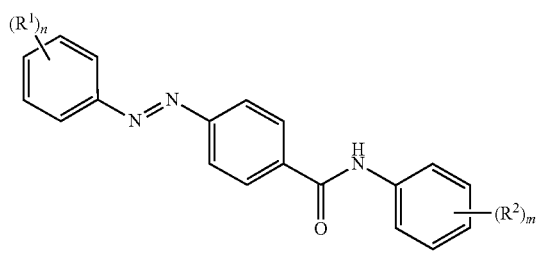

or a pharmaceutically acceptable salt thereof,
wherein:
each $R^1$ is independently an electron donating substituent;
each $R^2$ is independently selected from the group consisting of: halogen, $NR^3R^4$, $OR^3$, aryl, and heteroaryl;
each $R^3$ and $R^4$ is independently selected from the group consisting of: H, $C_{1-6}$ alkyl, and a nitrogen protecting group;
m is an integer from 1 to 5; and
n is an integer from 1 to 5.

This disclosure also provides a compound of Formula (V):

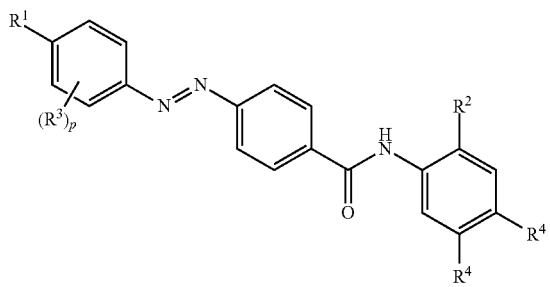

or a pharmaceutically acceptable salt thereof,
wherein:
$R^1$ is an electron donating substituent;
$R^2$ is selected from the group consisting of: $NR^{10}R^{11}$ and $OR^{10}$;
each $R^3$ is independently selected from the group consisting of: hydrogen, $C_{1-9}$alkyl, $C_{2-9}$alkenyl, $C_{2-9}$alkynyl, halo, $C_{1-9}$ haloalkyl, CN, $NO_2$, $OR^7$, $SR^7$, $C(O)R^7$, $C(O)NR^7R^8$, $C(O)OR^7$, $OC(O)R^7$, $OC(O)NR^7R^8$, $C(=NR^7)NR^8R^9$, $NR^7C(=NR^8)NR^9R^9$, $NR^7R^8$, $NR^7C(O)R^8$, $NR^7C(O)OR^8$, $NR^7C(O)NR^8R^9$, $NR^7S(O)R^8$, $NR^7S(O)_2R^8$, $NR^7S(O)_2NR^8R^9$, $S(O)R^7$, $S(O)NR^7R^8$, $S(O)_2R^7$, $S(O)_2NR^7R^8$, $C_{1-9}$alkoxyalkyl, carbocyclyl, $C_{1-9}$carbocyclylalkyl, heterocyclyl, $C_{1-9}$heterocyclylalkyl, aryl, $C_{1-9}$aralkyl, heteroaryl, and $C_{1-9}$heteroaralkyl;
each $R^4$ is independently selected from the group consisting of: H, halogen, aryl, and heteroaryl;
each $R^7$, $R^8$, and $R^9$ is independently selected from the group consisting of: H, $C_{1-6}$ alkyl;
$R^{10}$ and $R^{11}$ are independently selected from the group consisting of: H, $C_{1-6}$ alkyl, and a nitrogen protecting group; and
p is an integer from 0 to 4.

Non-limiting examples of a compound of Formula (I) include:

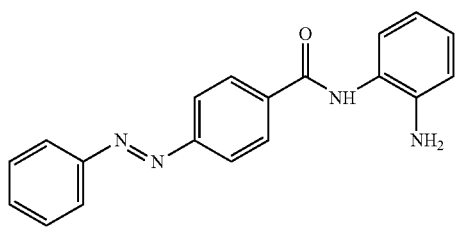

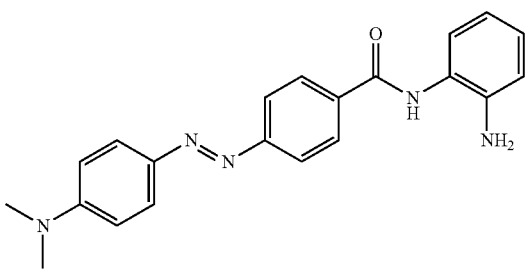

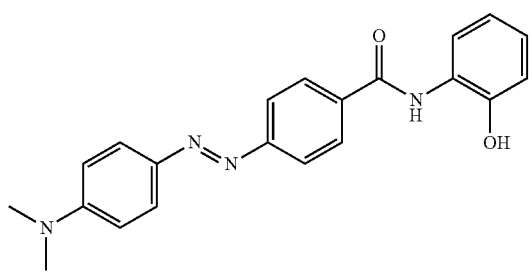

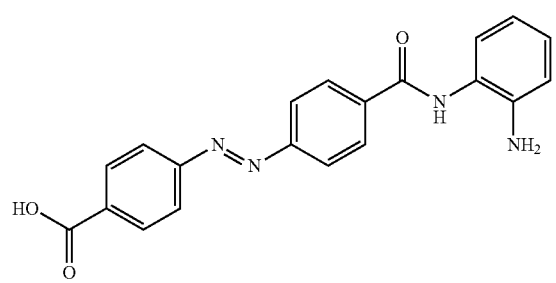

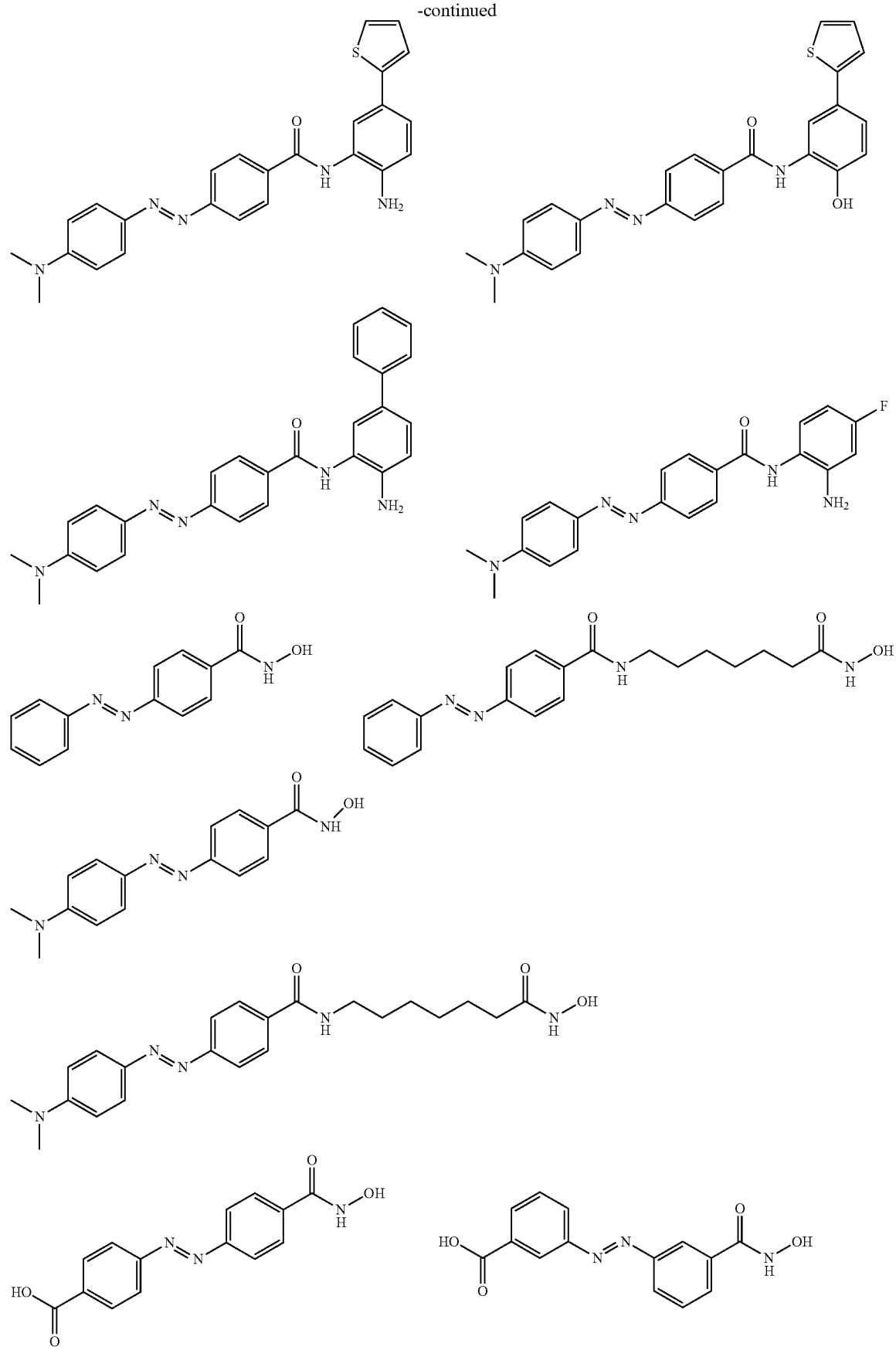

-continued
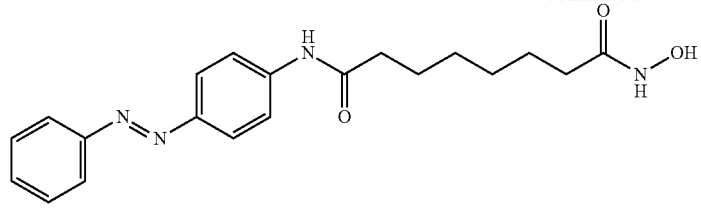
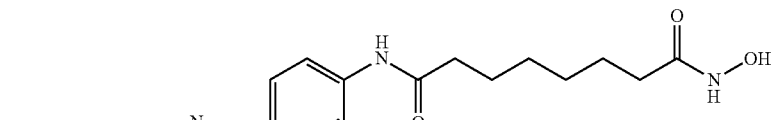
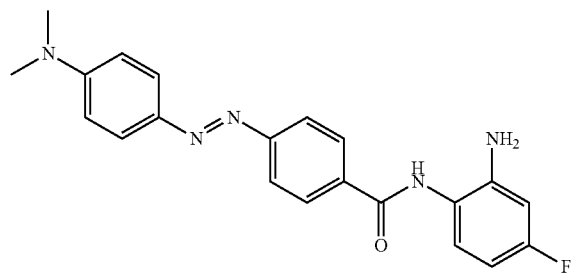
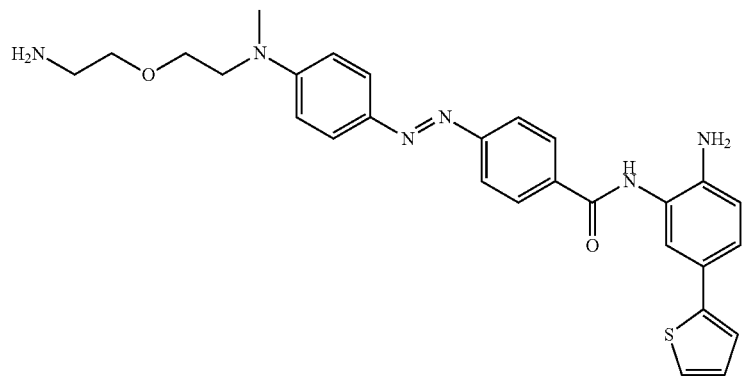
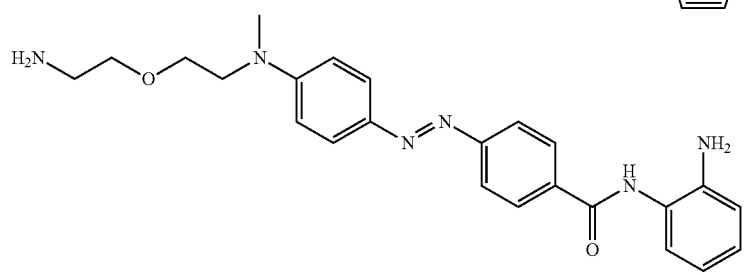
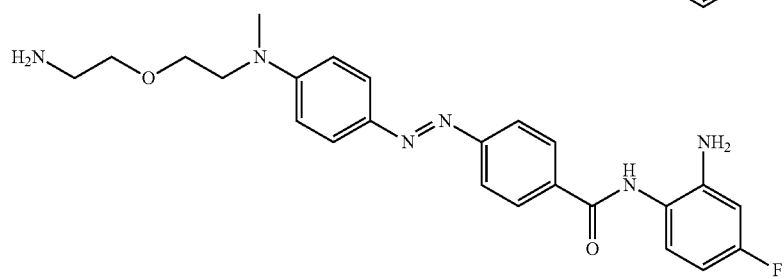

-continued

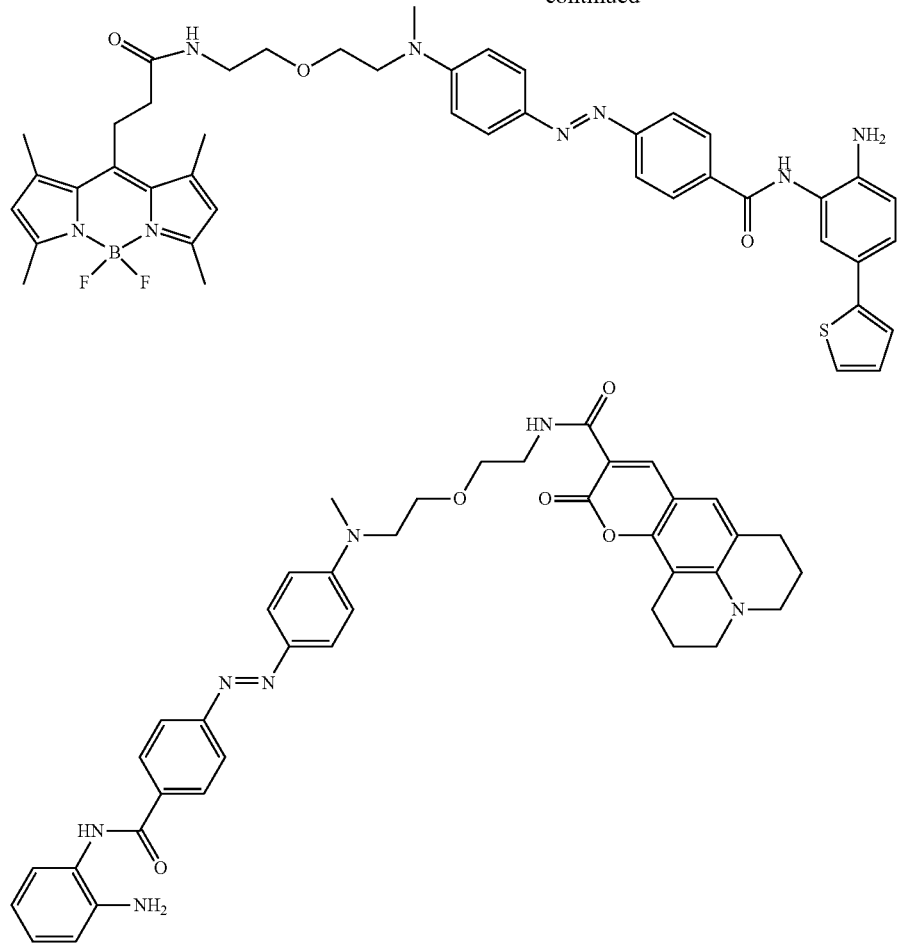

or a pharmaceutically acceptable salt form thereof.

The compounds and compositions provided herein are also useful for treating proliferative disorders (e.g., cancer, including skin cancer, and retinal disorders). Accordingly, a method is provided herein comprising administering a therapeutically effective amount of a compound of Formula (I) to the patient. For example, the method can include administering a therapeutically effective amount of a compound of Formula (I) to the patient; and exposing the patient to light suitable to convert the compound of Formula (I) to its cis confirmation. In some embodiments, the light exposure occurs at a location containing the cancer (e.g., the patient's skin).

In some embodiments, a compound provided herein can be used to inhibit an HDAC in a cell. The method can include contacting the cell with an effective amount of a compound of Formula (I). In some embodiments, the method can further include exposing the cell to light suitable to convert the compound of Formula (I) to its cis confirmation.

By virtue of their design, the compounds, compositions, and methods provided herein possess certain advantages and benefits. The compounds described herein can provide high spatiotemporal resolution in the treatment of various disease states (e.g., skin cancer and retinal disorders). Additionally, the compounds described herein can target treatment to specific areas of the body and therefore exhibit lower undesirable side effects.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 14A-14E provide (FIGS. 14A-14C) Western Blot analysis for acetylH3K9, (FIG. 14D) immunofluorescence staining, and (FIG. 14E) Quantification of the cell staining shown in FIG. 14D.

FIGS. 15A-15G provide a (FIG. 15A) representative example for light-dependent increase of gene transcription by BG14, (FIG. 15B) representative example for light-dependent decrease of gene transcription by BG14, (FIG. 15C) gene expression analysis demonstrates that transcriptional changes are light dependent. (FIG. 15D) Gene-Set-Enrichment-Analysis shows BG14 is highly similar to a standard HDAC inhibitor (CI-994) in the presence of light. (FIG. 15E) Venn-Diagram of genes regulated by CI-994 and BG14 with and without light. (FIG. 15F) Cellular networks regulated by BG14 in the presence of light. (FIG. 15G) BG14 regulates cell cycle network in the presence of light.

DETAILED DESCRIPTION

Definitions

Figure 1:
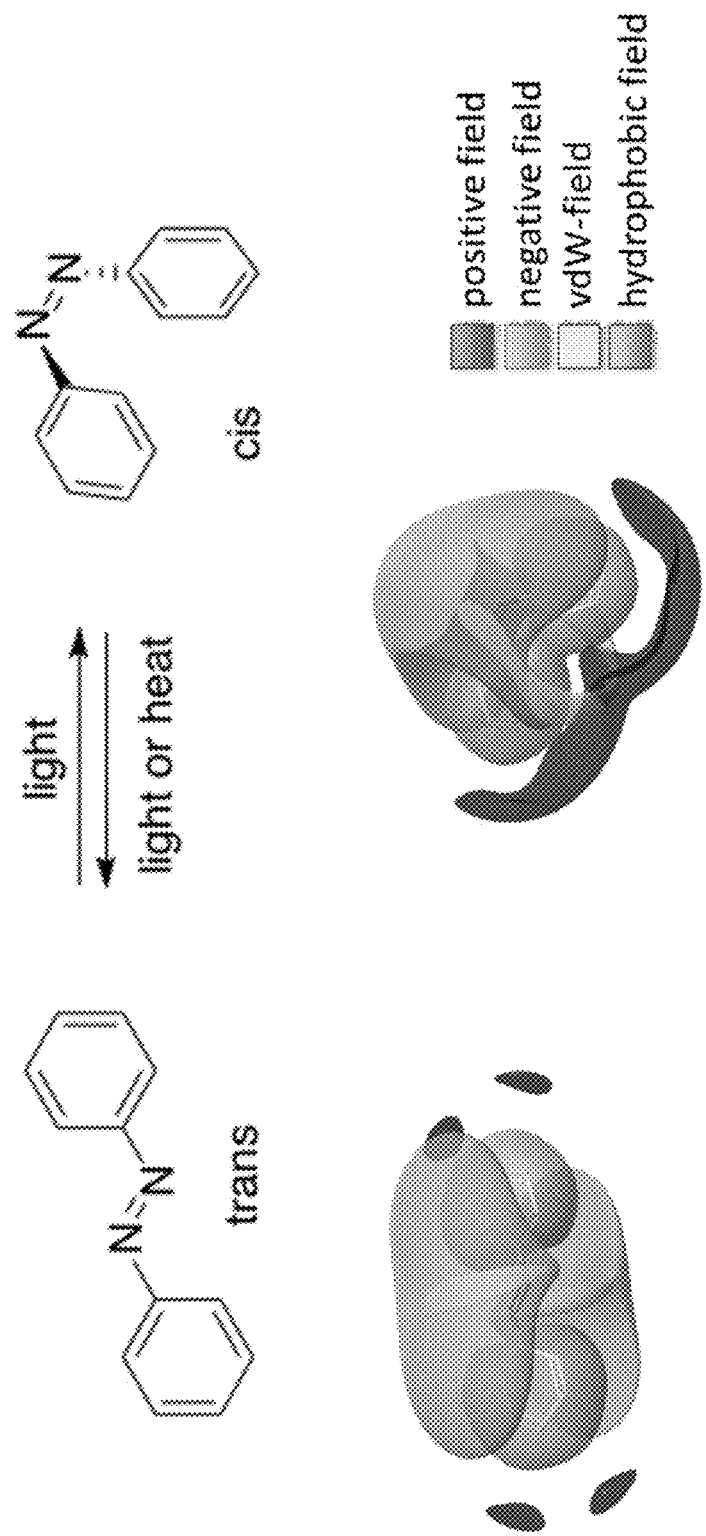
FIG. 1 illustrates differences between the trans and cis isomers of azobenzene.

For the terms "for example" and "such as," and grammatical equivalences thereof, the phrase "and without limitation" is understood to follow unless explicitly stated otherwise. All measurements reported herein are understood to be modified by the term "about", whether or not the term is explicitly used, unless explicitly stated otherwise. As used herein, the singular forms "a," "an," and "the" include plural referents unless the context clearly dictates otherwise.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents, e.g., halo, alkoxy, acyloxyl, amino, amido, cyano, nitro, hydroxyl, thiol, carboxyl, carbonyl, benzyloxy, aryl, heteroaryl, and with one or more fluorescent moieties. Alkyl groups can be saturated or unsaturated (e.g., containing —C═C— or —C≡C— sub- units), at one or several positions. Typically, alkyl groups will comprise 1 to 6 carbon atoms, for example, 1 to 4 or 1 to 2 carbon atoms.

As used herein, "aryl" means an aromatic radical having a single-ring (e.g., phenyl) or multiple condensed rings (e.g., naphthyl or anthryl) with only carbon atoms present in the ring backbone. Aryl groups can either be unsubstituted or substituted with one or more substituents, e.g., amino, cyano, hydroxyl, lower alkyl, haloalkyl, alkoxyl, nitro, halo, thiol, and other substituents. In some embodiments, an aryl is phenyl.

As used herein, the term "heteroaryl" means an aromatic radical having one or more heteroatom(s) (e.g., N, O, or S) in the ring backbone and may include a single ring (e.g., pyridine) or multiple condensed rings (e.g., quinoline). Heteroaryl groups can either be unsubstituted or substituted with one or more substituents, e.g., amino, cyano, hydroxyl, alkyl, haloalkyl, alkoxyl, nitro, halo, thiol, and other substituents (e.g., one or more fluorescent moieties). Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl.

As used herein, "halo", "halide" or "halogen" is a chloro, bromo, fluoro or iodo atom radical.

As used herein, "haloalkyl" means a hydrocarbon substituent, which is linear or branched or cyclic alkyl, alkenyl or alkynyl substituted with chloro, bromo, fluoro, or iodo atom(s).

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this invention, though such resonance forms or tautomers are not represented herein.

The compounds provided herein may encompass various stereochemical forms. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The term "administration" or "administering" refers to a method of giving a dosage of a compound or pharmaceutical composition to a vertebrate or invertebrate, including a mammal, a bird, a fish, or an amphibian, where the method is, e.g., orally, subcutaneously, intravenously, topically, transdermally, intraocularly, subconjuctivally, via anterior eye chamber injection, and intravitreally, inhalation. The method of administration can vary depending on various factors, for example, the components of the pharmaceutical composition, the site of the disease, the disease involved, and the severity of the disease.

The term "mammal" is used in its usual biological sense. Thus, it specifically includes humans, cattle, horses, dogs, and cats, but also includes many other species.

The term "pharmaceutically acceptable carrier" or "pharmaceutically acceptable excipient" includes any and all solvents, co-solvents, complexing agents, dispersion media, coatings, antibacterial and antifungal agents, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics.* 12th Ed., The McGraw-Hill Companies.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297.

"Patient" as used herein, means a human or a non-human mammal, for example, a dog, a cat, a mouse, a rat, a cow, a sheep, a pig, a goat, a non-human primate or a bird, for example, a chicken, as well as any other vertebrate or invertebrate.

A "therapeutically effective amount" or "pharmaceutically effective amount" is one the amount of a compound provided herein which is sufficient to achieve the desired effect and may vary according to the nature and severity of the disease condition, and the potency of the compound. "Therapeutically effective amount" is also intended to include one or more of the compounds in combination with one or more other agents that are effective to inhibit HDAC related diseases and/or conditions. The combination of compounds is preferably a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease, and includes curing a disease. "Curing" means that the symptoms of active disease are eliminated. However, certain long-term or permanent effects of the disease may exist even after a cure is obtained (such as extensive tissue damage).

"Treat," "treatment," or "treating," as used herein refers to administering a compound provided herein or a pharmaceutical composition comprising the same for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder and/or reducing the severity of symptoms that will or are expected to develop.

The term "contacting" means bringing at least two moieties together, whether in an in vitro system or an in vivo system.

Compounds

Light is a reagent that can be applied with unparalleled precision, and there have been various reports using light as an activator of small molecules (e.g. caged inhibitors) and proteins (e.g. rhodopsin) (Brieke, C. et al., *Angew. Chem. Int. Ed.* 2012, 2-34). More recently small molecules that feature unique chemical motifs, which can be switched reversibly between two distinct structural conformations (i.e. shapes or geometries) upon exposure to light of a specific wavelength, have attracted attention in protein engineering and small molecule inhibitor design (Brieke, C. et al., *Angew. Chem. Int. Ed.* 2012, 2-34; and Beharry, A. A. and Woolley, G. A., *Chem. Soc. Rev.* 2011, 40, 4422). Provided that the two structural confirmations exhibit distinct biological activity states (ideally active and inactive) and suitable photophysical properties, light can be used to modulate the activity of the respective compounds in physiological settings with high resolution enabling experiments probing biological events with sub-cellular precision and on millisecond timescales.

Many challenges are present in the development of such molecules. For example, the two molecular states (ground and excited) should exhibit a large difference in potency, ideally several orders of magnitude. In addition, switching between the two states should be efficient and switching to the low activity state (switch off) should be close to complete.

One well-studied photo-switchable compound class is based on azobenzene (see FIG. 1). The thermodynamic ground state of azobenzenes favors a trans geometry. Upon exposure to light of an appropriate wavelength, usually ultraviolet light, azobenzenes switch to an energetically higher cis geometry, a process referred to as photoisomerization (Beharry, A. A. and Woolley, G. A., *Chem. Soc. Rev.* 2011, 40, 4422). This process can be reverted by exposure to light of appropriate (generally longer) wavelength (Brieke, C. et al., *Angew. Chem. Int. Ed* 2012, 2-34; and Beharry, A. A. and Woolley, G. A., *Chem. Soc. Rev.* 2011, 40, 4422). Switching between cis- and trans-geometry has a profound impact on the overall shape, orientation of substituents and electronic properties of the molecule (see FIG. 1). The cis and trans isomers of biologically active azobenzenes that exploit any of these molecular characteristics for target binding are consequently expected to have significantly different potencies Beharry, A. A. and Woolley, G. A., *Chem. Soc. Rev.* 2011, 40, 4422; and Bandara, H. M. D.; Burdette, S. C., *Chem. Soc. Rev.* 2012, 41, 1809).

Figure 2:
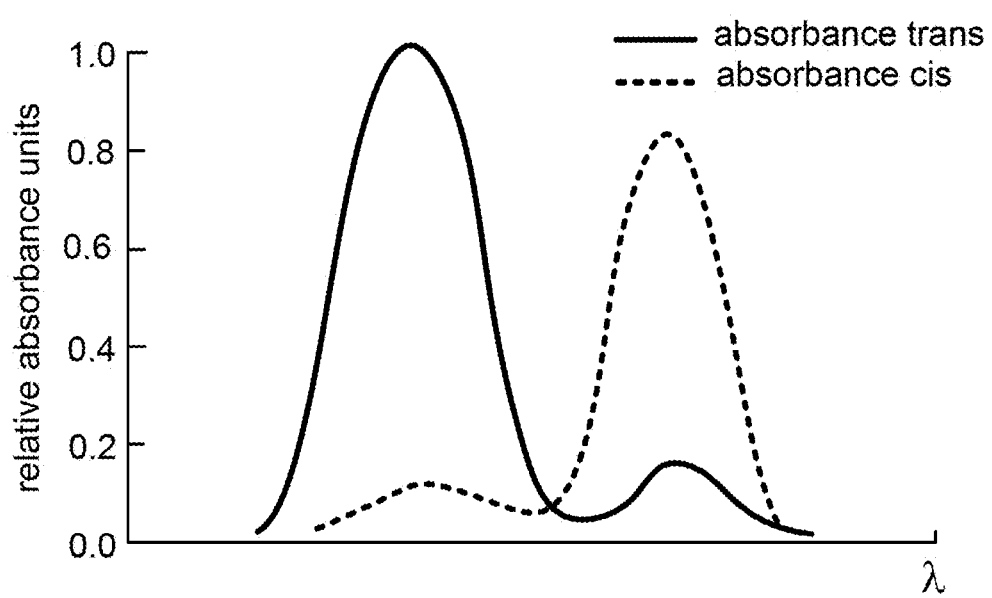
FIG. 2 illustrates the absorbance overlap between the trans and cis isomers of azobenzene.
Figure 3:
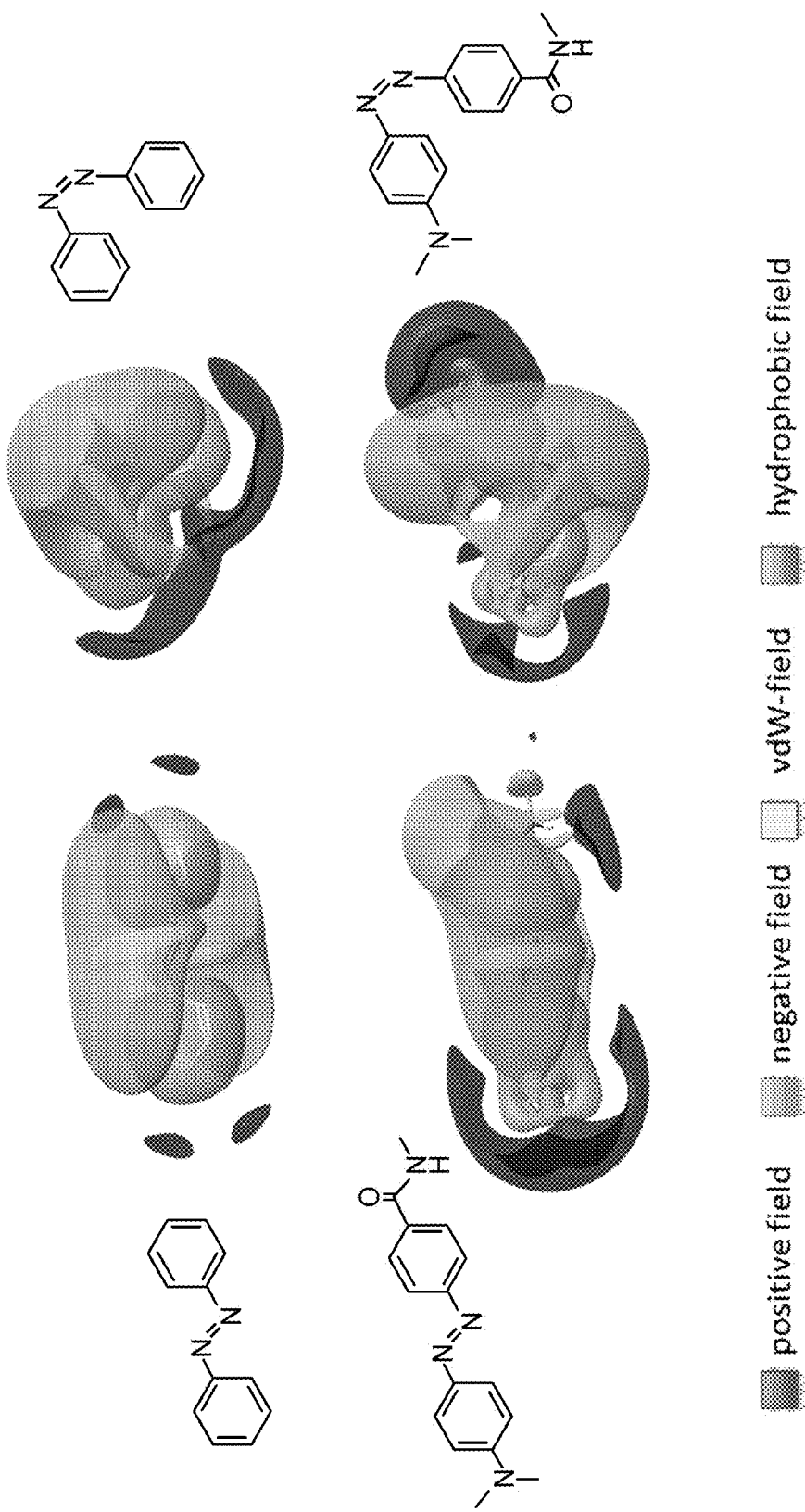
FIG. 3 illustrates differences between the trans and cis isomers of unsubstituted and substituted azobenzenes.

Unfortunately, photo-induced switching of azobenzenes between cis and trans geometry is not quantitative. The maximum ratio between the two geometries correlates with the inverse ratio of absorbance coefficients of both isomers at the wavelength that is used for switching (see FIG. 2). Because the absorbance spectra of the cis and trans isomers overlap it is generally only possible to change the cis/trans ratio within one order of magnitude (e.g., between 9:1 and 1:9, respectively) and therefore the ability to modulate the activity of such a compound by light is confined within this range. In contrast to photo-induced relaxation, thermal relaxation is quantitative. Generally, the cis-azobenzene is thermodynamically less favored and will thermally relax back to the more stable trans isomer. The rate constant of this process, amongst other factors such as solvent polarity and pH, is dependent on the electronic properties of the substituents attached to the azobenzene core and can range from microseconds to months (see FIG. 3) (Brieke, C. et al., *Angew. Chem. Int. Ed* 2012, 2-34; and Beharry, A. A. and Woolley, G. A., *Chem. Soc. Rev.* 2011, 40, 4422).

Much of the development to date has focused on the synthesis of diazobenzenes with medium to long thermal relaxation half-lives (seconds or longer), while compounds with short (milliseconds) and very short (sub-milliseconds) thermal relaxation half-lives are generally considered less attractive (Brieke, C. et al., *Angew. Chem. Int. Ed.* 2012, 2-34; and Beharry, A. A. and Woolley, G. A., *Chem. Soc. Rev.* 2011, 40, 4422). One reason for this is that maintaining a significant population of the cis-isomer of a photoswitchable compound with fast thermal relaxation requires very high light intensity (resulting in overheating of the biological specimen) and the concentration of cis-isomer could very rapidly decline immediately after termination of light exposure. This feature, however, can be an advantage when exploited properly. The rapid isomerization back to the ground (inactive state) limits the off target effects that can arise from active pharmacological agents circulating in the body and interacting with other biomacromolecules as is the case for bare therapeutics, prodrugs, and caged compounds.

Generally azobenzenes with short thermal relaxation half-lives are so called push-pull systems (type III). These are functionalized azobenzenes that carry an electron-donating substituent on one aryl group and an electron-withdrawing substituent on the other. Azobenzenes, push-push or pull-pull substitution patterns (type II) have longer thermal relaxation kinetics, while those azobenzenes with none or electroneutral substituents (type I) are most stable.

Azobenzenes with push-pull substitution patterns have a number of superior properties compared to the other classes of azobenzenes. They generally absorb longer wavelength light compared to the other classes, which tend to require tissue damaging violet to UV-light. Furthermore, type III azobenzenes absorb light more efficiently (i.e. they have the highest absorbance coefficient). Lastly, the disruption of the push-pull system, which is the consequence of adopting the cis-confirmation, causes the strongest relative change of the electronic property of the aromatic system and substituents (see FIG. 3). Therefore, if electronic effects are important for targeting and engagement of the compound, a large difference in affinity between the cis and trans isomer is expected. The affinity of a small molecule ligand is defined by the equilibrium dissociation constant $K_D$ that represents the fraction of the dissociation rate $(k_{off})$ over the association rate $(k_{on})$. Small molecule inhibitors generally exhibit relatively fast on- and off-rates. As a result the equilibrium of bound and unbound inhibitor is reached within seconds. There are many small molecule ligands derived from a wide variety of inhibitor classes, however, that are characterized by slow binding kinetics. The dissociation half-lives of such ligand-protein complexes can range from minutes to hours or even days. This critical feature is frequently not appreciated. In particular, in therapeutic settings long dissociative half-lives can be very desirable to help ensure long-term target inhibition for drugs having a short systemic exposure (Swinney, D. *PART VI: Topics in Biology-18 Molecular Mechanism of Action (MMoA) in Drug Discovery*; Annual Reports in Medicinal Chemistry, 2011; Swinney, D. C. *Pharmaceutical Medicine* 2008, 22, 23-34; and Copeland, R. A.; Pompliano, D. L.; Meek, T. D. *Nat Rev Drug Discov* 2006, 5, 730-739).

As provided herein, the terms "slow" and "fast" used to describe the thermal relaxation kinetics of azobenzenes and the binding kinetics of a small molecule ligand to its biological target, respectively, are relative descriptors for each process. The two processes occur on different time scales and "very fast" thermal relaxation is a "very slow" process ($t_{1/2}$=millisecond time scale) with respect to ligand binding kinetics of a ligand with "slow" on rates ($k_{on}=10^8$ $M^{-1}$ $s^{-1}$).

Comparing the events on an absolute time scale it is more likely for an activated cis-azobenzene ligand with fast relaxation kinetics to bind to its target (provided affinity) than to thermally relax to the inactive trans-isomer. The target proteins are acting similar to a sponge that scavenges the cis-isomers until the binding capacity is reached. Once bound, the cis-isomer is stabilized by ligand-target interaction and possibly sterically locked (similar to a jack-in-the-box), preventing relaxation to the inactive isomer while bound to the target protein. Thus, ligands with long target residence time will cause prolonged target inhibition following short term light exposure independent from the thermal relaxation kinetics of the respective cis-azobenzene. One advantage of fast relaxing azobenzenes in addition to favorable photophysical properties (benign wavelength, high absorbance coefficient) is the immediate self-deactivation of the respective ligands, which are not engaged with a target protein, once exposure to light is ceased or if the activated molecule diffuses outside the light-exposed area. Activity of corresponding ligands with longer thermal relaxation rates would fade off slowly, providing less control and potentially causing remote target effects.

Provided herein are a set of compounds that are structurally related to a specific class of histone deacetylases (HDAC) inhibitors, which feature a common amino-benzamide or hydroxy-benzamide pharmacophor. This HDAC inhibitor class includes, for example, CI-994 and MS-275.

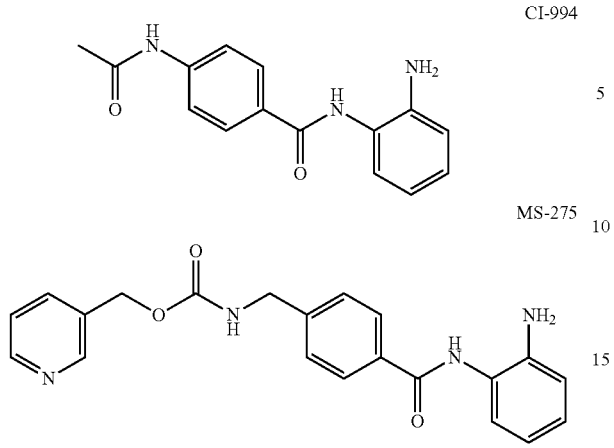

CI-994

MS-275

Benzamides generally show remarkable preference for HDACs1-3 over other HDAC isoforms. Further selectivity and increased potency for HDAC1/2 over HDAC3 can be attained by introduction of aryl substituents in the 4'-position (Moradei, O. M. et al., *J. Med. Chem.* 2007, 50, 5543-5546; and Witter, D. J. et al., *Bioorg. Med. Chem. Lett.* 2008, 18, 726-731). These modification exploit isoform specific features within an internal cavity that is adjacent to the catalytic zinc and proposed to serve as a release pathway for acetate following enzymatic hydrolysis (Wang, D.-F. et al., *J. Med. Chem.* 2004, 47, 3409-3417; Tessier, P. et al., *Bioorg. Med. Chem. Lett.* 2009, 19, 5684-5688; and Bressi, J. C. et al., *Bioorg. Med. Chem. Lett.* 2010, 20, 3142-3145). Phenyl-, 2-thienyl and 2-furyl-substituents have been identified by both groups as attractive pharmacophores. In contrast to other HDAC inhibitors, benzamides are characterized by long target residence time.

As shown below, the compounds provided herein are designed as hybrids between a generic benzamide HDAC inhibitor and the azobenzene motif, sharing a common electron-withdrawing (pull system) on one end.

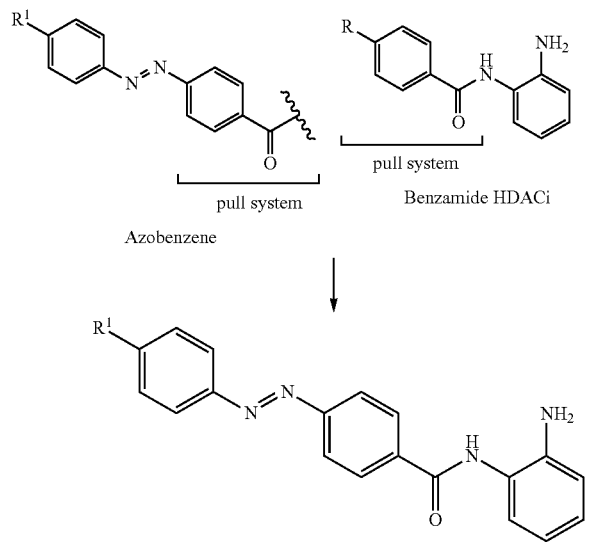

This design is advantageous for a number of reasons. The amino-benzamide is acting as a chelator that binds the catalytic zinc in the active site. The binding affinity of the chelator is strongly dependent on the electronic properties of the benzamide. Electron-rich benzamides are generally low affinity ligands, while electron neutral or electron-withdrawing ligands result in increased affinity. It is expected that the hybrid molecule is electron rich as a result of the conjugation of both aromatic systems. This effect is significantly increased by addition of an electron donating ligand (push system) onto the azobenzene aryl ring.

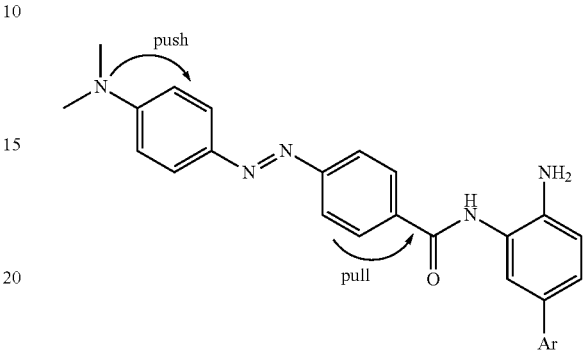

Transition to the cis-geometry upon light exposure will disrupt this effect, resulting in increased binding affinity.

In addition, it is important to appreciate that the azobenzene motif is predicted to bind within the catalytic pocket, which is spatially confined. It is therefore reasonable to expect that one geometry will provide a better fit compared to the other. Provided that the cis-configuration represents the preferred binding geometry, both electronic and spatial contributions will be additive and result in the largest differential activity between the trans and cis isomer. A set of compounds have been prepared which exhibit the benefits and structural properties described above.

Provided herein is a compound of Formula (I):

or a pharmaceutically acceptable salt thereof,
wherein:
X and Y are independently a substituted or unsubstituted aryl or heteroaryl ring, wherein at least one of the rings is substituted with one or more HDAC targeting elements. In some embodiments, the HDAC targeting element is selected from the group consisting of a substituted or unsubstituted aminobenzamide, a substituted or unsubstituted hydroxybenzamide, and hydroxamic acids. For example, the HDAC targeting element can include the terminal phenylformamide moiety of an benzamide histone deacetylase (HDAC) inhibitor.

In some embodiments, Y is substituted with one or more HDAC targeting elements and X is substituted with one or more fluorescent moieties. Non-limiting examples of suitable fluorescent moieties include boron-dipyrromethene (BODIPY®), 4,4-difluoro-5,7-dimethyl-4-bora-3a,4a-diaza-s-indacene-3-propionic acid (BODIPY® FL), 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY® TRM-X), Oregon Green 88, 6-(((4,4-difluoro-5-(2-pyrrolyl)-4-bora-3a,4a-diaza-s-indacene-3-yl)styryloxy)acetyl)aminohexanoic acid, succinimidyl ester (BODIPY® 650/665-X), a Coumarin, such as 7-N,N-diethylaminocoumarin and Coumarin 343, sulforhodamine 101 acid chloride (Texas Red), VIVOTAG 680 (an amine-reactive near-infra-red fluorochrome, from VisEn Medical), umbelliferone, fluorescein, fluorescein isothiocyanate, rhodamine, dichlorotriazinylamine fluorescein, and dansyl chloride or phycoerythrin. See, for example SAS130.

In some embodiments, a compound of Formula (I) is a compound of Formula (II):

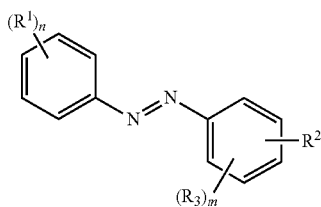

or a pharmaceutically acceptable salt thereof,
wherein:
each $R^1$ is independently selected from the group consisting of: hydrogen, $C_{1-6}$alkyl, $C_{2-6}$alkenyl, $C_{1-6}$alkynyl, halo, $C_{1-6}$ haloalkyl, CN, $NO_2$, $OR^4$, $SR^4$, $C(O)R^4$, $C(O)NR^4R^5$, $C(O)OR^4$, $OC(O)R^4$, $OC(O)NR^4R^5$, $C(=NR^4)NR^5R^6$, $NR^4C(=NR^5)NR^6R^7$, $NR^4R^5$, $NR^4C(O)R^5$, $NR^4C(O)OR^5$, $NR^4C(O)NR^5R^6$, $NR^4S(O)R^5$, $NR^4S(O)_2R^5$, $NR^4S(O)_2NR^5R^6$, $S(O)R^4$, $S(O)NR^4R^5$, $S(O)_2R^4$, $S(O)_2NR^4R^5$, $C_{1-6}$alkoxyalkyl, carbocyclyl, $C_{1-6}$carbocyclylalkyl, heterocyclyl, $C_{1-6}$heterocyclylalkyl, aryl, $C_{1-6}$aralkyl, heteroaryl, and $C_{1-6}$heteroaralkyl;
$R^2$ is an HDAC targeting element;
$R^3$ is independently selected from the group consisting of: $C_{1-6}$alkyl, $C_{2-6}$alkenyl, $C_{2-6}$alkynyl, halo, $C_{1-6}$ haloalkyl, CN, $NO_2$, $OR^4$, $SR^4$, $C(O)R^4$, $C(O)NR^4R^5$, $C(O)OR^4$, $OC(O)R^4$, $OC(O)NR^4R^5$, $C(=NR^4)NR^5R^6$, $NR^4C(=NR^5)NR^6R^7$, $NR^4R^5$, $NR^4C(O)R^5$, $NR^4C(O)OR^5$, $NR^4C(O)NR^5R^6$, $NR^4S(O)R^5$, $NR^4S(O)_2R^5$, $NR^4S(O)_2NR^5R^6$, $S(O)R^4$, $S(O)NR^4R^5$, $S(O)_2R^4$, $S(O)_2NR^4R^5$, $C_{1-6}$alkoxyalkyl, carbocyclyl, $C_{1-6}$carbocyclylalkyl, heterocyclyl, $C_{1-6}$heterocyclylalkyl, aryl, $C_{1-6}$aralkyl, heteroaryl, and $C_{1-6}$heteroaralkyl;
each $R^4$, $R^5$, and $R^6$ are independently selected from H and $C_{1-6}$alkyl;
m is an integer from 0 to 4; and
n is an integer from 1 to 5.

In some embodiments, a compound of Formula (I) is a compound of Formula (III):

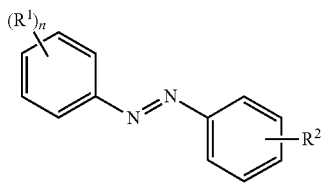

or a pharmaceutically acceptable salt form thereof;
wherein:
each $R^1$ is selected from the group consisting of: hydrogen, $C_{1-6}$alkyl, $C_{2-6}$alkenyl, $C_{2-6}$alkynyl, halo, $C_{1-6}$ haloalkyl, CN, $NO_2$, $OR^4$, $SR^4$, $C(O)R^4$, $C(O)NR^4R^5$, $C(O)OR^4$, $OC(O)R^4$, $OC(O)NR^4R^5$, $C(=NR^4)NR^5R^6$, $NR^4C(=NR^5)NR^6R^7$, $NR^4R^5$, $NR^4C(O)R^5$, $NR^4C(O)OR^5$, $NR^4C(O)NR^5R^6$, $NR^4S(O)R^5$, $NR^4S(O)_2R^5$, $NR^4S(O)_2NR^5R^6$, $S(O)R^4$, $S(O)NR^4R^5$, $S(O)_2R^4$, $S(O)_2NR^4R^5$, $C_{1-6}$alkoxyalkyl, carbocyclyl, $C_{1-6}$carbocyclylalkyl, heterocyclyl, $C_{1-6}$heterocyclylalkyl, aryl, $C_{1-6}$aralkyl, heteroaryl, and $C_{1-6}$heteroaralkyl;

each $R^4$, $R^5$, and $R^6$ are independently selected from H and $C_{1-6}$alkyl;
$R^2$ is an HDAC targeting element; and
n is an integer from 1 to 5.

In some embodiments, $R^1$ is an electron donating substituent. Essentially any functional group capable of releasing electrons into the pi-electron system of an aromatic ring system is suitable for use as an electron donating group, provided that the group is also capable of being covalently attached to the aryl ring. An electron donating substituent can include, for example, a substituent having a Hammett $\sigma_p$ value of less than zero (see, for example, "A survey of Hammett substituent constants and resonance and field parameters", Corwin. Hansch, A. Leo, R. W. Taft *Chem. Rev.*, 1991, 91 (2), pp 165-195).

Examples of suitable electron donating groups known in the art include $NR^5R^6$, $OR^5$, $SR^5$, $C_{1-6}$ alkyl, $CH=N-NR^5R^6$, $CH=C(NR^5R^6)_2$, $NR^5COR^6$, $NR^5C(O)NR^6R^7$, aryl, and heteroaryl; wherein each $R^5$, $R^6$ and $R^7$ are independently selected from H and $C_{1-6}$ alkyl. For example, $R^1$ can be $NR^5R^6$. In some embodiments, $R^1$ is $N(CH_3)_2$.

HDAC targeting elements include any small molecule compound capable of binding to HDAC. In some embodiments, the HDAC targeting element is selected from the group consisting of a substituted or unsubstituted aminobenzamide, a substituted or unsubstituted hydroxybenzamide, and hydroxamic acids. For example, the HDAC targeting element can include the terminal phenylformamide moiety of an benzamide histone deacetylase (HDAC) inhibitor.

In some embodiments, an HDAC targeting element includes an HDAC inhibitor. In some embodiments, suitable histone deacetylase (HDAC) inhibitors can include those compounds having a phenyl benzamide moiety. For example, CI-994, Entinostat (MS-275),

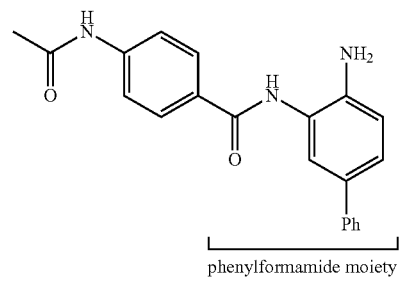 [SMILES: CC(=O)Nc1ccc(C(=O)Nc2cc(-c3ccccc3)ccc2N)cc1]

phenylformamide moiety

HDAC1/2 Selective CI-994 Analog (see, e.g., Methot, J. L. et al., *Bioorg. Med Chem. Lett.*, 18(3), 973-8 (2008)),

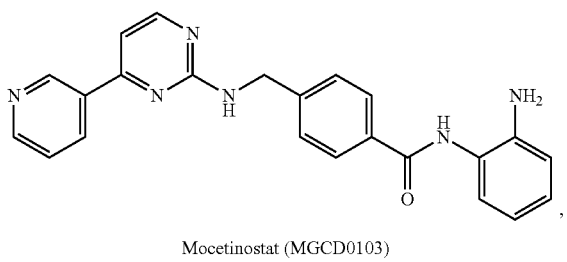 [SMILES: Nc1ccccc1NC(=O)c1ccc(CNc2nccc(-c3cccnc3)n2)cc1]

Mocetinostat (MGCD0103)

and analogs thereof. See also WO 2004/058234; Methot, J. L. et al., *Bioorg. Med Chem. Lett.*, 18(3), 973-8 (2008); Witter, D. J. et al., *Bioorg. Med. Chem. Lett.*, 18(2), 726-31 (2008); and Haggarty, S. J. et al., *Neurobiol Learn Mem*, 96(1), 41-52 (2011), all of which are incorporated by reference in their entirety herein. Analogs of benzamide HDAC inhibitors can include compounds having an additional substituent on the terminal phenyl ring of the phenyl benzamide moiety. Substituents can include aryl and heteroaryl rings. For example, the phenyl ring can be substituted with a phenyl or thienyl moiety in addition to the substituents present on the parent HDAC inhibitor. See, for example, the HDAC1/2 selective CI-994 analog shown above.

In some embodiments, the HDAC inhibitor is a HDAC3 selective inhibitors (see, e.g., Haggarty, S. J. et al., *Neurobiol Learn Mem*, 96(1), 41-52 (2011)). HDAC3 selective compounds are characterized by a 4-fluoro substitutent, such as:

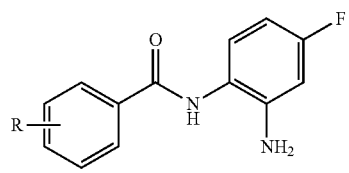

In some embodiments, m is 0. In some embodiments, n is an integer from 1 to 2. For example, n can be 1.

Also provided herein is a compound of Formula (IV):

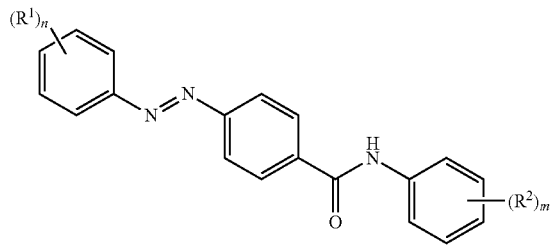

or a pharmaceutically acceptable salt thereof,
wherein:
each $R^1$ is independently an electron donating substituent;
each $R^2$ is independently selected from the group consisting of: halogen, $NR^3R^4$, $OR^3$, aryl, and heteroaryl;
each $R^3$ and $R^4$ is independently selected from the group consisting of: H, $C_{1-6}$ alkyl, and a nitrogen protecting group;
m is an integer from 1 to 5; and
n is an integer from 1 to 5.

In some embodiments, $R^1$ is an electron donating substituent as described above. For example, $R^1$ can include: $NR^5R^6$, $OR^5$, $SR^5$, $C_{1-6}$ alkyl, $CH=N-NR^5R^6$, $CH=C(NR^5R^6)_2$, $NR^5C(O)NR^6R^7$, aryl, and heteroaryl; wherein each $R^5$, $R^6$ and $R^7$ are independently selected from H and $C_{1-6}$ alkyl. For example, $R^1$ can be $NR^5R^6$. In some embodiments, $R^1$ is $N(CH_3)_2$. In some embodiments, n is 1 and $R^1$ is in the para position on the ring.

In some embodiments, $R^2$ is $NR^3R^4$. For example $R^2$ can be $NH_2$. In some embodiments, $R^2$ is selected from the group consisting of $NH_2$, OH, phenyl, and thiophenyl. In some embodiments, m is 1 and $R^2$ is in the ortho position on the ring. In some embodiments, m is 2 and the first $R^2$ is in the ortho position and the second $R^2$ is in the meta position across the ring from the first $R^2$.

As indicated, certain amino groups of the Formula (II) structure may be protected with an nitrogen protecting group. For this purpose, the protecting group may include any suitable functional group chosen by a person skilled in the chemical arts. For example, amino protecting groups within the scope of the present disclosure include, but are not limited to, carbamate, amide, A-alkyl, or A-aryl-derived protecting groups. Each protecting group may be the same or different.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzo[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)] methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (7-Bumeoc), N-2-pivaloylamino)-1,1-dimethylethyl carbamate, 2-[(2-nitrophenyl)dithio]-1-phenylethyl carbamate (NpSSPeoc), 2-(N,N-dicyclohexylcarboxamido)ethyl carbamate, 1-adamantyl carbamate (1-Adoc), vinyl carbamate (Voc), 1-isopropylallyl carbamate (Ipaoc), 4-nitrocinnamyl carbamate (Noc), 3-(3'pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In particular, 9-fluorenylmethyl carbamate (Fmoc), t-butyl carbamate (Boc), and carboxybenzyl carbamate (cbz) protecting groups may be used.

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide.

In some embodiments, the nitrogen protecting group is t-butyl carbamate (Boc).

In some embodiments, m is an integer from 1 to 3 (e.g., 1, 2 or 3). In some embodiments, m is 1 or 2. For example, m can be 1. In some embodiments, n is an integer from 1 to 3 (e.g., 1, 2 or 3). In some embodiments, n is 1 or 2. For example, n can be 1.

Further provided herein are compounds of Formula (V):

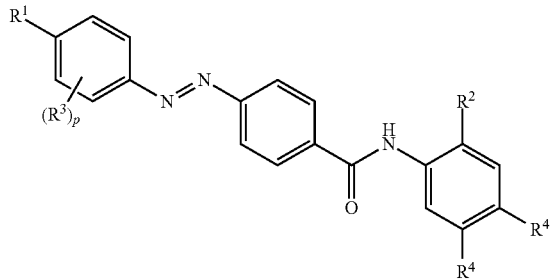

or a pharmaceutically acceptable salt thereof,
wherein:
$R^1$ is an electron donating substituent;
$R^2$ is selected from the group consisting of: $NR^{10}R^{11}$ and $OR^{10}$;
each $R^3$ is independently selected from the group consisting of: hydrogen, $C_{1-9}$alkyl, $C_{2-9}$alkenyl, $C_{2-9}$alkynyl, halo, $C_{1-9}$ haloalkyl, CN, $NO_2$, $OR^7$, $SR^7$, $C(O)R^7$, $C(O)NR^7R^8$, $C(O)OR^7$, $OC(O)R^7$, $OC(O)NR^7R^8$, $C(=NR^7)NR^8R^9$, $NR^7C(=NR^8)NR^9R^9$, $NR^7R^8$, $NR^7C(O)R^8$, $NR^7C(O)OR^8$, $NR^7C(O)NR^8R^9$, $NR^7S(O)R^8$, $NR^7S(O)_2R^8$, $NR^7S(O)_2NR^8R^9$, $S(O)R^7$, $S(O)NR^7R^8$, $S(O)_2R^7$, $S(O)_2NR^7R^8$, $C_{1-9}$alkoxyalkyl, carbocyclyl, $C_{1-9}$carbocyclylalkyl, heterocyclyl, $C_{1-9}$heterocyclylalkyl, aryl, $C_{1-9}$aralkyl, heteroaryl, and $C_{1-9}$heteroaralkyl;

each $R^4$ is independently selected from the group consisting of: H, halogen, aryl, and heteroaryl;
each $R^7$, $R^8$, and $R^9$ is independently selected from the group consisting of: H, $C_{1-6}$ alkyl;
$R^{10}$ and $R^{11}$ are independently selected from the group consisting of: H, $C_{1-6}$ alkyl, and a nitrogen protecting group; and
p is an integer from 0 to 4.

The electron donating substituent and nitrogen protecting group are as defined above.

In some embodiments, $R^1$ can be $NR^5R^6$. For example, $R^1$ can be $N(CH_3)_2$. In some such embodiments, p is 0.

In some embodiments, $R^2$ is $NR^{10}R^{11}$. For example $R^2$ can be $NH_2$. In some such embodiments, $R^4$ is selected from the group consisting of phenyl, and thiophenyl.

Non-limiting examples of the compounds provided herein include:

BG-12

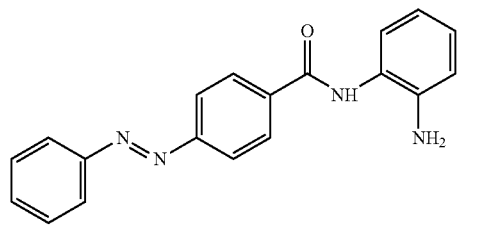

BG-14

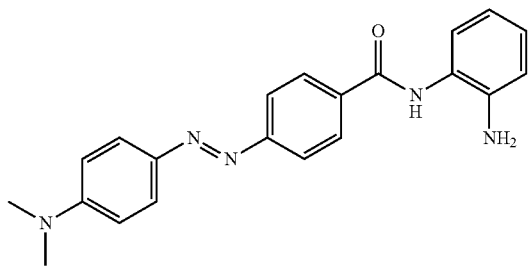

BG-18

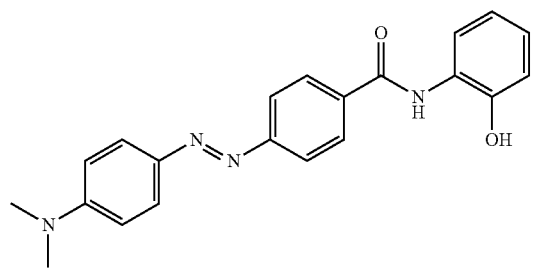

BG-19

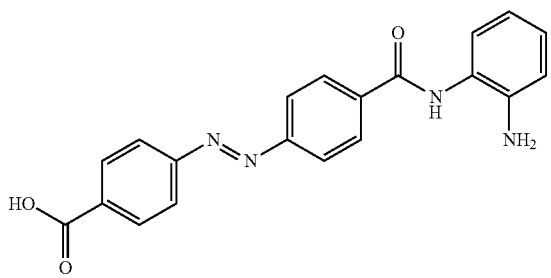

BG-48

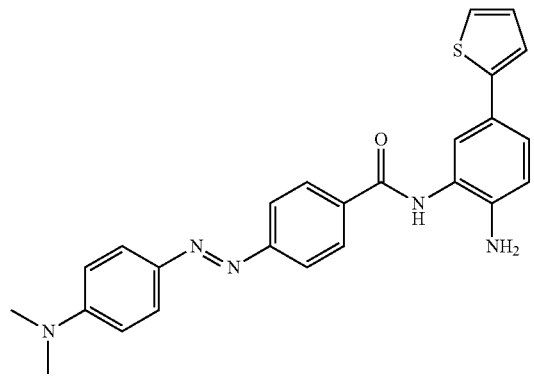

BG-47

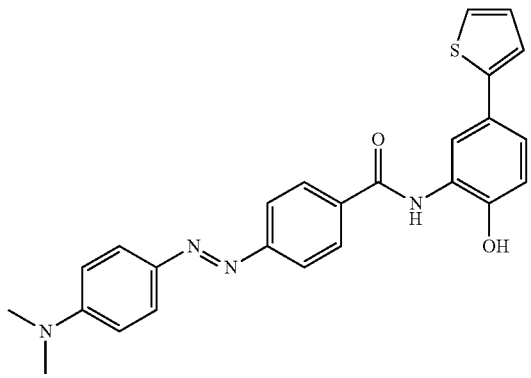

BG-49
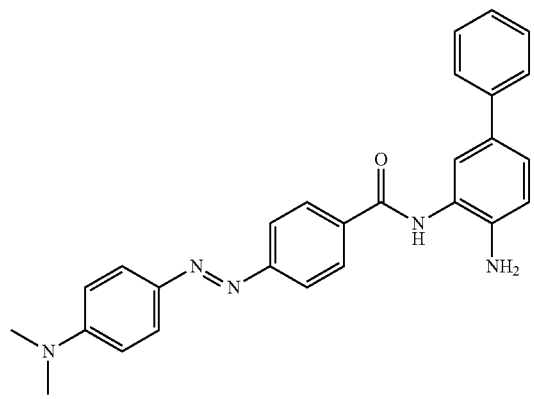
BG-66
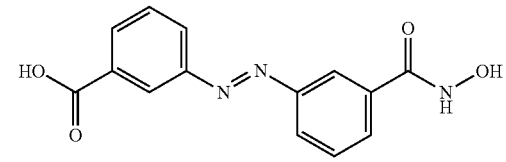
BG-20
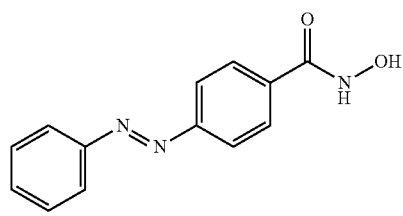
BG-13
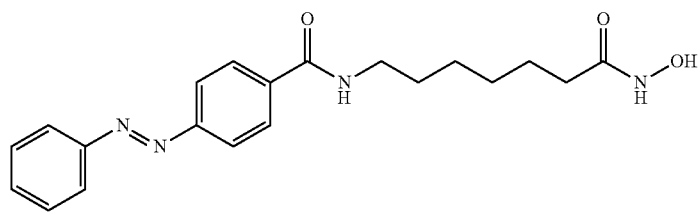
BG-46
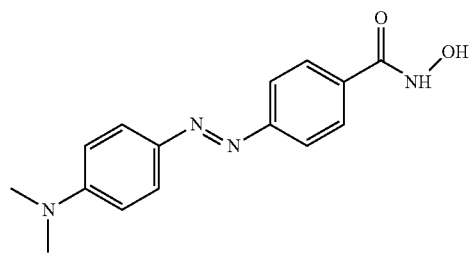
BG-15
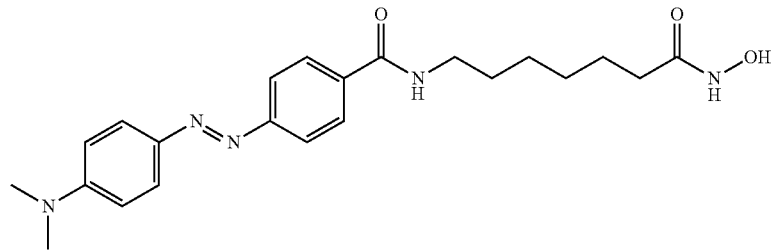
BG-22
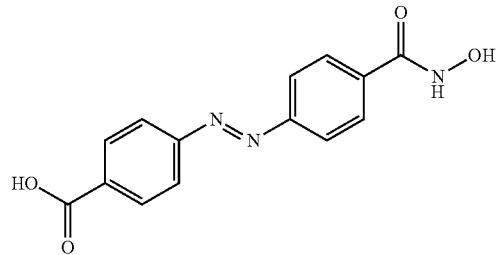
BG-21

-continued
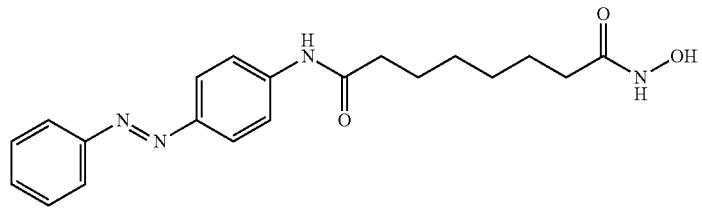
BG-16
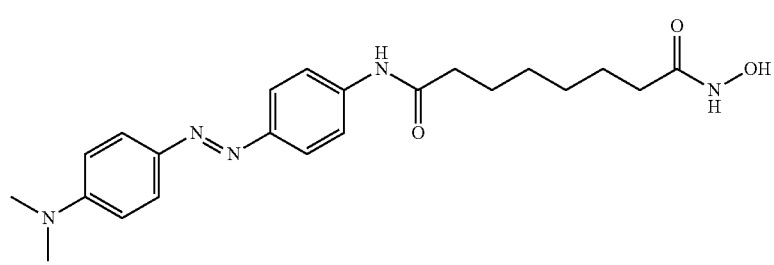
BG-17
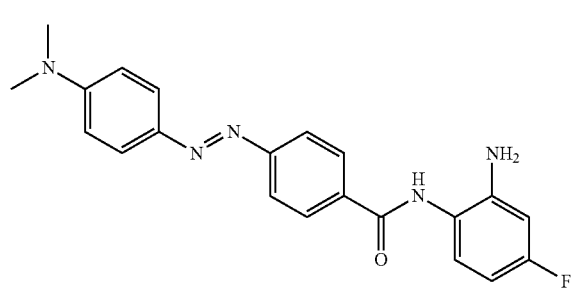
BG-66
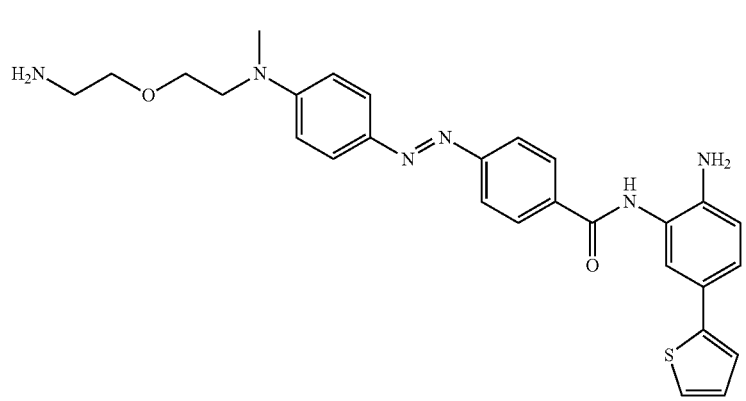
BG-67
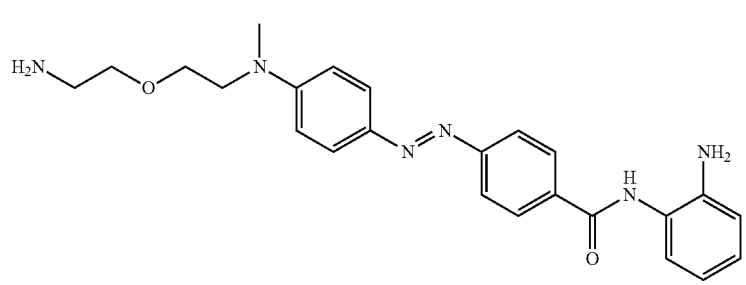
BG-68

BG-69

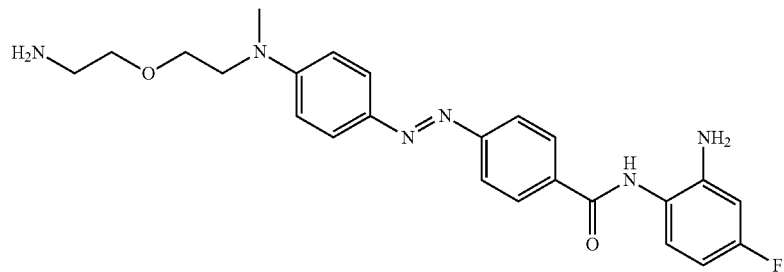

BG-70

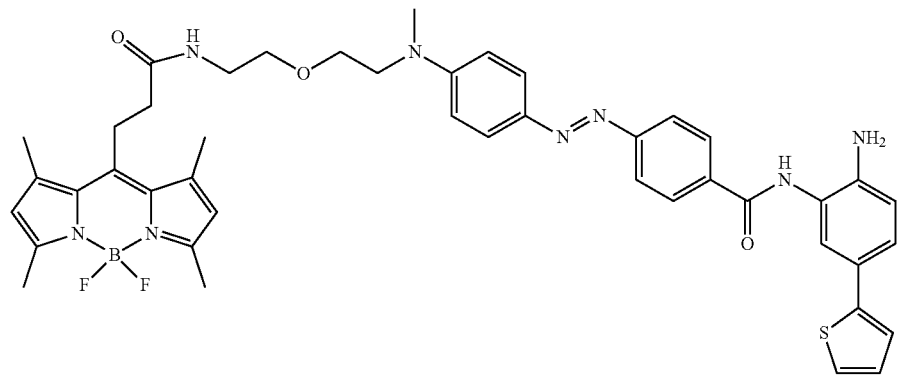

SAS130

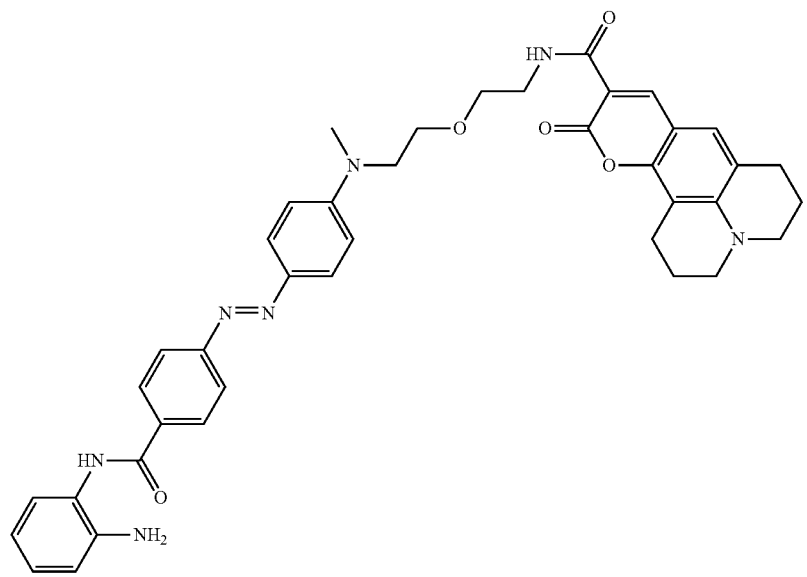

and pharmaceutically acceptable salt forms thereof.

Also provided herein are the cis-isomers of the compounds provided above. Such compounds can be prepared by irradiating the corresponding trans-isomer with a suitable wavelength of light to induce the conformational change. Accordingly, provided herein are compounds of formula (VI):

or a pharmaceutically acceptable salt thereof, wherein:

X and Y are independently a substituted or unsubstituted aryl or heteroaryl ring, wherein at least one of the rings is substituted with one or more HDAC targeting elements. In some embodiments, the HDAC targeting element is selected from the group consisting of a substituted or unsubstituted aminobenzamide, a substituted or unsubstituted hydroxybenzamide, and hydroxamic acids. For example, the HDAC targeting element can include the terminal phenylformamide moiety of an benzamide histone deacetylase (HDAC) inhibitor.

Also provided herein is a compound of Formula (VII):

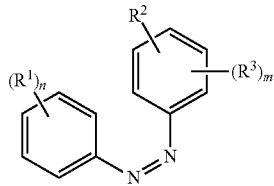

or a pharmaceutically acceptable salt thereof,
wherein:
each $R^1$ is independently selected from the group consisting of: hydrogen, $C_{1-6}$alkyl, $C_{2-6}$alkenyl, $C_{2-6}$alkynyl, halo, $C_{1-6}$ haloalkyl, CN, $NO_2$, $OR^4$, $SR^4$, $C(O)R^4$, $C(O)NR^4R^5$, $C(O)OR^4$, $OC(O)R^4$, $OC(O)NR^4R^5$, $C(=NR^4)NR^5R^6$, $NR^4C(=NR^5)NR^6R^7$, $NR^4R^5$, $NR^4C(O)R^5$, $NR^4C(O)OR^5$, $NR^4C(O)NR^5R^6$, $NR^4S(O)R^5$, $NR^4S(O)_2R^5$, $NR^4S(O)_2NR^5R^6$, $S(O)R^4$, $S(O)NR^4R^5$, $S(O)_2R^4$, $S(O)_2NR^4R^5$, $C_{1-6}$alkoxyalkyl, carbocyclyl, $C_{1-6}$carbocyclylalkyl, heterocyclyl, $C_{1-6}$heterocyclylalkyl, aryl, $C_{1-6}$aralkyl, heteroaryl, and $C_{1-6}$heteroaralkyl;
$R^2$ is an HDAC targeting element;
$R^3$ is independently selected from the group consisting of: $C_{1-6}$alkyl, $C_{2-6}$alkenyl, $C_{2-6}$alkynyl, halo, $C_{1-6}$ haloalkyl, CN, $NO_2$, $OR^4$, $SR^4$, $C(O)R^4$, $C(O)NR^4R^5$, $C(O)OR^4$, $OC(O)R^4$, $OC(O)NR^4R^5$, $C(=NR^4)NR^5R^6$, $NR^4C(=NR^5)NR^6R^7$, $NR^4R^5$, $NR^4C(O)R^5$, $NR^4C(O)OR^5$, $NR^4C(O)NR^5R^6$, $NR^4S(O)R^5$, $NR^4S(O)_2R^5$, $NR^4S(O)_2NR^5R^6$, $S(O)R^4$, $S(O)NR^4R^5$, $S(O)_2R^4$, $S(O)_2NR^4R^5$, $C_{1-6}$alkoxyalkyl, carbocyclyl, $C_{1-6}$carbocyclylalkyl, heterocyclyl, $C_{1-6}$heterocyclylalkyl, aryl, $C_{1-6}$aralkyl, heteroaryl, and $C_{1-6}$heteroaralkyl;
each $R^4$, $R^5$, and $R^6$ are independently selected from H and $C_{1-6}$alkyl;
m is an integer from 0 to 4; and
n is an integer from 1 to 5.

In some embodiments, a compound of Formula (VI) is a compound of Formula (VIII):

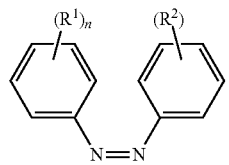

or a pharmaceutically acceptable salt thereof,
wherein:
each $R^1$ is selected from the group consisting of: hydrogen, $C_{1-6}$alkyl, $C_{2-6}$alkenyl, $C_{2-6}$alkynyl, halo, $C_{1-6}$ haloalkyl, CN, $NO_2$, $OR^4$, $SR^4$, $C(O)R^4$, $C(O)NR^4R^5$, $C(O)OR^4$, $OC(O)R^4$, $OC(O)NR^4R^5$, $C(=NR^4)NR^5R^6$, $NR^4C(=NR^5)NR^6R^7$, $NR^4R^5$, $NR^4C(O)R^5$, $NR^4C(O)OR^5$, $NR^4C(O)NR^5R^6$, $NR^4S(O)R^5$, $NR^4S(O)_2R^5$, $NR^4S(O)_2NR^5R^6$, $S(O)R^4$, $S(O)NR^4R^5$, $S(O)_2R^4$, $S(O)_2NR^4R^5$, $C_{1-6}$alkoxyalkyl, carbocyclyl, $C_{1-6}$carbocyclylalkyl, heterocyclyl, $C_{1-6}$heterocyclylalkyl, aryl, $C_{1-6}$aralkyl, heteroaryl, and $C_{1-6}$heteroaralkyl;
each $R^4$, $R^5$, and $R^6$ are independently selected from H and $C_{1-6}$alkyl;
$R^2$ is an HDAC targeting element; and
n is an integer from 1 to 5.

Further provided herein are compounds of Formula (IX):

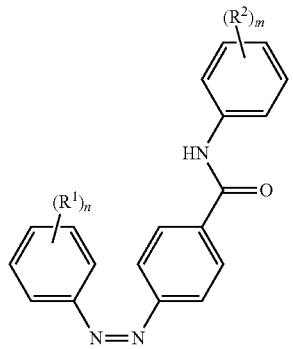

or a pharmaceutically acceptable salt thereof, wherein each $R^1$ is independently an electron donating substituent; each $R^2$ is independently selected from the group consisting of: halogen, $NR^3R^4$, $OR^3$, aryl, and heteroaryl; each $R^3$ and $R^4$ is independently selected from the group consisting of: H, $C_{1-6}$ alkyl, and a nitrogen protecting group; m is an integer from 1 to 5; and n is an integer from 1 to 5 as defined above for the compounds of Formula (II).

Finally, provided herein are compounds of Formula (X):

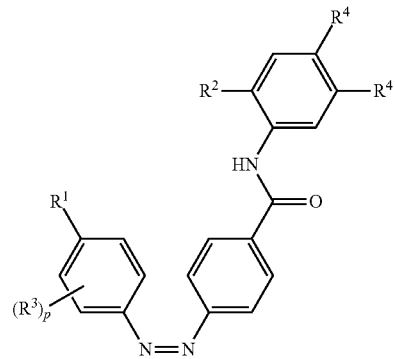

or a pharmaceutically acceptable salt thereof, wherein:
wherein:
$R^1$ is an electron donating substituent;
$R^2$ is selected from the group consisting of: $NR^{10}R^{11}$ and $OR^{10}$;
each $R^3$ is independently selected from the group consisting of: hydrogen, $C_{1-9}$alkyl, $C_{2-9}$alkenyl, $C_{2-9}$alkynyl, halo, $C_{1-9}$ haloalkyl, CN, $NO_2$, $OR^7$, $SR^7$, $C(O)R^7$, $C(O)NR^7R^8$, $C(O)OR^7$, $OC(O)R^7$, $OC(O)NR^7R^8$, $C(=NR^7)NR^8R^9$, $NR^7C(=NR^8)NR^9R^9$, $NR^7R^8$, $NR^7C(O)R^8$, $NR^7C(O)OR^8$, $NR^7C(O)NR^8R^9$, $NR^7S(O)R^8$, $NR^7S(O)_2R^8$, $NR^7S(O)_2NR^8R^9$, $S(O)R^7$, $S(O)NR^7R^8$, $S(O)_2R^7$, $S(O)_2NR^7R^8$, $C_{1-9}$alkoxyalkyl, carbocyclyl, $C_{1-9}$carbocyclylalkyl, heterocyclyl, $C_{1-9}$heterocyclylalkyl, aryl, $C_{1-9}$heteroaryl, and $C_{1-9}$heteroaralkyl;
each $R^4$ is independently selected from the group consisting of: H, halogen, aryl, and heteroaryl;
each $R^7$, $R^8$, and $R^9$ is independently selected from the group consisting of: H, $C_{1-6}$ alkyl;
$R^{10}$ and $R^{11}$ are independently selected from the group consisting of: H, $C_{1-6}$ alkyl, and a nitrogen protecting group; and
p is an integer from 0 to 4.

Pharmaceutical Compositions and Methods of Administration

The methods described herein include the manufacture and use of pharmaceutical compositions, which include the compounds provided herein as active ingredients. Also included are the pharmaceutical compositions themselves.

Pharmaceutical compositions typically include a pharmaceutically acceptable carrier. A pharmaceutically acceptable carrier includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

The term "ophthalmic composition" as used herein will be understood to refer to any composition for direct or local administration to an eye of a patient. The composition may be administered topically to the eye or may be injected into the eye (e.g., intravitreal injection, subconjunctival injection, sub-tenon injection, retrobulbar injection, subretinal injection, suprachoroidal injection, and the like). The ophthalmic composition may be provided in any form that allows local or direct administration thereof to the eye, including but not limited to, a solution, drops, mist/spray, plasters and pressure sensitive adhesives, ointment, lotion, cream, gel, lyophilized/spray-dried forms, rods, beads, emulsions, lenses, patch, plug, elixir, and the like. The ophthalmic compositions provided herein typically vary according to the particular active agent (i.e., a compound provided herein) used, the preferred drug release profile, the condition being treated, and the medical history of the patient. In addition, the ophthalmic compositions of the present disclosure may be designed to provide delayed, controlled or sustained release using formulation techniques which are well known in the art.

Any of the ophthalmic compositions described and claimed herein may further comprise at least one delivery agent that assists in the penetration of a surface of an eye; in certain embodiments, the delivery agent may assist in delivery to the cornea and/or retina of the eye. For example, in order for a topical application to be effective, the composition may need to be able to penetrate the surface of the eye so that it can travel to the desired tissue. This may include penetrating the conjunctiva and/or the cornea. Also, the penetration rate must be sufficient to impart an effective dose. Many drugs do not possess a requisite penetration ability with regard to the tissues of the eye. It should be noted that the external layers of the eye are quite different from the tissues encountered in the stomach and intestinal tract. Thus, while a certain drug may be readily absorbed in the intestines and introduced into the blood supply for systemic administration, the same drug may be incapable of being absorbed by or passing through the substantially avascular outer layers of the conjunctiva or cornea at a minimally acceptable therapeutic concentration. The mechanism of transport or uptake of the drug is entirely different for topical administration than for oral administration.

In one embodiment, the compounds provided herein are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

An "effective amount" is an amount sufficient to effect beneficial or desired results. For example, a therapeutically effective amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the compounds selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a compound provided herein can include a single treatment or a series of treatments.

Dosage, toxicity and therapeutic efficacy of the compounds provided herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Methods of Treatment

The methods described herein include methods for the treatment of disorders associated with aberrant histone deacetylase activity. In some embodiments, the disorder is cancer. Generally, the methods include administering a therapeutically effective amount of a compound as described herein, to a patient who is in need thereof, or who has been determined to be in need of, such treatment. Following administration of the compound to the patient, the compound can be activated by exposure of the patient to a suitable wavelength of light to convert the compound from its inactive or relatively inactive trans isomer to the active or more active cis isomer.

The compounds and compositions provided herein can be used as inhibitors and/or modulators of histone deacetylases, and thus can be used to treat a variety of disorders and diseases in which histone deacetylase activity is implicated, such as proliferative diseases (e.g., cancers, benign neoplasms, angiogenesis, inflammatory diseases, and autoimmune diseases, genetic diseases).

In certain embodiments, the disease can be proliferative diseases, such as cancer; autoimmune diseases; allergic and inflammatory diseases; diseases of the central nervous system (CNS), such as neurodegenerative diseases (e.g., Huntington's disease, amyotrophic lateral sclerosis (ALS)); vascular diseases, such as restenosis; musculoskeletal diseases; cardiovascular diseases, such as stroke; pulmonary diseases; gastric diseases; genetic diseases, such as spinal muscle atrophy; infectious diseases; diseases associated with an HPV infection; and Alzheimer's disease.

Histone deacetylase is known to play an essential role in the transcriptional machinery for regulating gene expression, induce histone hyperacetylation and to affect the gene expression. Therefore, it is useful as a therapeutic or prophylactic agent for diseases caused by abnormal gene expression such as inflammatory disorders, diabetes, diabetic complications, homozygous thalassemia, fibrosis, cirrhosis, acute promyelocytic leukaemia (APL), organ transplant rejections, autoimmune diseases, protozoal infections, and tumors.

In some embodiments, a compound or composition provided herein can be used to treat cancer (e.g., skin cancer) and/or retinal disorders. Accordingly, the compounds and compositions provided herein can be used to treat cancer and/or retinal disorders. Examples of diseases which can be treated with the compounds and compositions provided herein include a variety of cancers, including skin cancer, and retinal disorders including, for example, ischemic retinal injury, and retinal degeneration (e.g., retinitis pigmentosa).

With respect to cancer, histone deacetylase is thought to be involved in the regulation of cellular proliferation in a variety of cancers including, for example, skin cancer. Non-limiting examples of skin cancers include malignant melanoma, basal cell carcinoma, squamous cell carcinoma, Kaposi's sarcoma, moles dysplastic nevi, lipoma, angioma, dermatofibroma, keloids, and scleroderma.

Other cancers can also be treated with the compounds and compositions described herein.

A method of treating cancer using a compound or composition as described herein may be combined with existing methods of treating cancers, for example by chemotherapy, irradiation, or surgery (e.g., removal of skin). In some embodiments, a compound or composition can be administered before, during, or after another anticancer agent or treatment.

A method of inhibiting an HDAC in a cell is also provided herein, the method comprising contacting the cell with an effective amount of a compound of Formula (I). In some embodiments, the method further comprising exposing the cell to a light suitable to convert the compound of Formula (I) to its cis confirmation. The method of inhibiting an HDAC in a cell may be performed by contacting the cell with a compound according to Formula (I), or a pharmaceutically acceptable salt form thereof, in vitro, thereby inducing inhibition of an HDAC of a cell in vitro. Uses of such an in vitro method of inhibiting an HDAC include, but are not limited to use in a screening assay (for example, wherein a compound according to Formula (I) is used as a positive control or standard compared to compounds of unknown activity or potency in inhibiting HDAC). In some embodiments thereof, HDAC is inhibited in a cancer cell (e.g., a skin cancer cell).

The method of inhibiting an HDAC in a cell may be performed, for example, by contacting a cell with a compound according to Formula (I), in vivo, thereby inhibiting an HDAC in a subject in vivo. The contacting is achieved by causing a compound according to Formula (I), or a pharmaceutically acceptable salt form thereof, to be present in the subject in an amount effective to achieve inhibition of the HDAC. This may be achieved, for example, by administering an effective amount of a compound according to Formula (I), or a pharmaceutically acceptable salt form thereof, to a patient. In some embodiments, the method further comprising exposing the cell to a light suitable to convert the compound of Formula (I) to its cis confirmation. Such exposure can occur, for example, by exposing the patient to the light (e.g., exposing the portion of the patient wherein the cell of interest is located). Uses of such an in vivo method of inhibiting HDAC include, but are not limited to, use in methods of treating a disease or condition, wherein inhibiting HDAC is beneficial. In some embodiments thereof, the HDAC is inhibited in a cancer cell, for example in a patient suffering from cancer. The method can be performed by administering an effective amount of a compound according to Formula (I), or a pharmaceutically acceptable salt form thereof, to a patient who is suffering from cancer.

Without being bound by theory, when Y is substituted with an HDAC targeting element and X is substituted with a fluorescent moiety, it is believed that the portion of the compound of Formula (I) including the HDAC targeting element can function as a fluorescent quencher while the compound of Formula (I) is in its unbound or trans configuration, thus quenching the fluorescent signal produced by the compound. The portion of the compound including the HDAC targeting element functions similarly to DABCYL. Upon conversion to the cis configuration and subsequent binding of the compound to the active site of HDAC, the DABCYL-like moiety has a decreased ability to quench the fluorescence of the fluorescent moiety and the fluorescent signal produced by the compound can increase significantly. Accordingly, in some embodiments, a compound provided herein can be used in a method to detectably label an HDAC (e.g., the active site of an HDAC) in a cell or in a patient. The fluorescent signal produced by the bound compound can be detected by methods known by those of skill in the art.

As is discussed above, the compounds provided herein are administered in the inactive or less active trans configuration. Following administration of the compound to the patient, the compound can be activated by exposure of the patient to light, thus converting the compound from the inactive trans to the active cis configuration. In some embodiments, the light can be targeted specifically at the area of the patient to be treated. For example, light can be focused onto the cancerous portions of the skin or into the retina of the eye. In this way, the activated drug is able to bind and inhibit HDAC at the location of need while much of the remaining inactive drug is removed from the patient through normal excretion pathways. In some embodiments, the thermal relaxation of the compound from the active or more active cis configuration to the trans configuration is fast and upon removal of the patient from the light source, any unbound compound thermally relaxes back into the inactive or less active state.

Any suitable light source may be used to activate the compounds provided herein. For example, topical and intraocular application of visible light; a laser can be used to provide light to the patient; for exposure of the blood to light, the light can be administered from outside of the body or intravenously. In some embodiments, after the location of cancer cells is determined, laser energy of a desired wavelength, intensity, duration and modulation is delivered to the cancer cells. In some embodiments, after the location of the area to be treated is determined (e.g., the eye), laser energy of a desired wavelength, intensity, duration and modulation is delivered to the targeted location.

Delivery of light may be by, for example, light bulb, LED, fluorescent light tube, sunlight, and/or direct laser application to the affected region of the body. An example of wavelengths of light effective to convert the compounds provided herein from the trans to cis configuration are from about 200 nm to about 800 nm. In some embodiments, the wavelength of light ranges from about 350 nm to about 550 nm. For example, the light can be in the blue region of the visible spectrum (i.e., about 450 nm to about 495 nm). The energy level of the light may be from 0.1 watt to 15 watts. In some embodiments, the energy level of the light is less than 0.1 watt. An example treatment time for exposing the patient to light can be from less than 1 minute to more than 1 hour.

In some embodiments, direct laser application of light is made to the affected region of the body. Alternatively, a fiber needle or fiber can be used to deliver laser light/laser energy to the patient. For example, a fiber needle assembly to delivery laser energy to targeted location can be one or multiple fibers depending on the size of the location (e.g., depending on the size of the tumor to be treated). Multiple fiber needles can be inserted inside the body in different directions so that the targeted location can be surrounded or covered completely by laser energy coming at the location from different directions.

Lasers can be solid state lasers, gas lasers, semiconductor lasers and others. An example of wavelengths of laser light effective to convert the compounds provided herein from the trans to cis configuration are from about 200 nm to about 800 nm. In some embodiments, the wavelength of light ranged from about 350 nm to about 550 nm. For example, the light can be in the blue region of the visible spectrum (i.e., about 450 nm to about 495 nm). The energy level of a laser may be from 0.1 watt to 15 watts. In some embodiments, the energy level of the laser is less than 0.1 watt. An example treatment time for exposing the patient to laser energy can be from less than 1 minute to more than 1 hour. The laser energy applied to the patient may also be modulated. Laser energy may be applied to the targeted location by continuous wave (constant level), pulsing (on/off), ramping (from low to high power levels, or from high to low power levels), or other waveform (such as sine wave, square wave, triangular wave, etc.). Modulation of laser energy may be achieved by modulating power to the laser light source, or by blocking or reducing light output from the laser light source according to a desired modulation pattern.

EXAMPLES

The invention is further described in the following examples, which do not limit the scope of the invention described in the claims.

Example 1—Preparation of Compound Intermediates

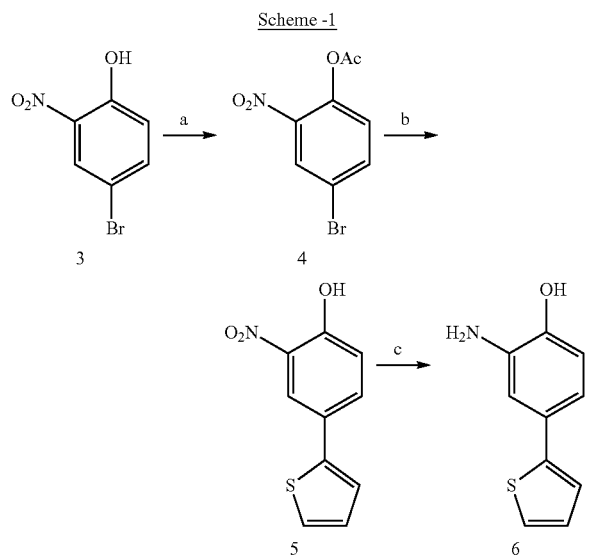

Reagents & conditions: (a) Ac$_2$O, microwave at 160° C., 10 min. (b) Ar-B(OH)$_2$, K$_3$PO$_4$, Pd$_2$dba$_3$, ligand, n-butanol, 130° C., 20 min. (c) H$_2$, Pd/C, MeOH

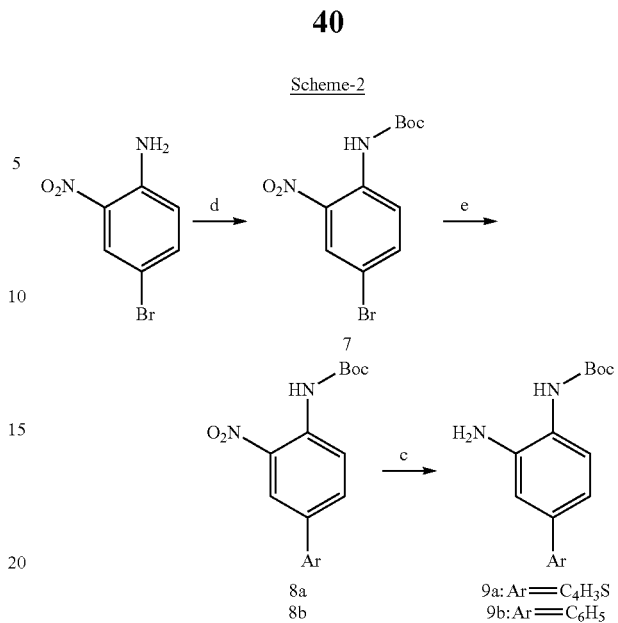

Reagents & conditions: (d) i.Boc$_2$O, 4-DMAP, THF, 18 h, ii. NaOH, H$_2$O, THF, 4 h, rt-70° C.; 18 h. (e) Ar-B(OH)$_2$, tri-o-tolyl-phosphine, K$_2$CO$_3$, Pd(PPh$_3$)$_4$(0), DME, H$_2$O, 80° C., 20 min.

Synthesis of 4-bromo-2-nitrophenyl acetate (4)

4-bromo-2-nitrophenyl acetate was made following the reported procedure with little modification (WO 2005/030705). A solution of 4-bromo-2-nitrophenol (0.25 g, 1.147 mmol) in acetic anhydride (2.5 mL) was exposed to microwave reaction at 160° C. for 10 minutes. Most of the solvent was evaporated in vacuo and the resulting oil was kept in the freezer for 3 days. Crystallization occurred while thawing the sample at room temperature. The yellowish crystals were suspended in a mixture of EtOAc/hexane (9:1) and collected by filtration to afford the title compound 4 (0.24 g, 81.1% yield). $^1$H NMR: (400 MHz, CDCl3) δ (ppm): 8.22 (d, J=2 Hz, 1H), 7.76 (dd, J=5.4 Hz, 2.4 Hz, 1H), 7.13 (d, J=8.4 Hz, 1H), 2.358 (s, 3H).

Synthesis of 2-nitro-4-(thiophen-2-yl)phenol (5)

In a microwave vessel, 4-bromo-2-nitrophenyl acetate (1.3 g, 5 mmol), thiophen-2-ylboronic acid (1.14 g, 8.9 mmol), tribasic potassium phosphate (2.52 g, 11.9 mmol), tris-(dibenzylideneacetone)dipalladium(O) (0.0563 g, 0.061 mmol), and 2-dicyclohexyl-phosphino-2',4',6'-triisopropyl biphenyl (0.114 bg, 0.239 mmol) were added in w-butanol (18 mL) and after degassing with argon exposed to microwave reaction for 20 min. After cooling, the mixture was diluted with EtOAc and extracted from water. The organic layer was rinsed with brine, dried over sodium sulphate and concentrated to give a crude mixture which was then purified by column chromatography using EtOAc/hexane (20: 80) to give the title compound (0.024 g, 22% yield). $^1$H NMR: (400 MHz, CDCl$_3$) δ (ppm): 7.75 (d, J=16 Hz, 1H), 7.6 (m, 2H), 7.4 (m, 2H), 7.1 (d, J=16 Hz, 1H).

Synthesis of 2-amino-4-(thiophen-2-yl)phenol (6)

The nitro compound (0.075 g, 0.34 mmol) was hydrogenated via balloon in the presence of 10% palladium on charcoal (catalytic amount) in methanol (2 mL) at room temperature for 2 hours. The crude product was filtered through a pad of Celite, and the filtrate was evaporated to give the desired compound sufficiently pure to use for the next reaction (0.065 g, 100% yield). $^1$H NMR: (400 MHz, DMSO-$d_6$) δ (ppm): 7.34 (d, J=6 Hz, 1H), 7.16 (d, J=4.8, 1H), 7.03 (t, J=4.2, 1H), 6.86 (s, 1H), 6.67 (m, 2H).

Synthesis of tert-butyl (4-bromo-2-nitrophenyl)carbamate (7)

This intermediate compound was made following the reported procedure (WO 2009/055917). To a stirred solution of 4-bromo-2-nitroanile (10.0 g, 46.1 mmol) and di-tert-butyl dicarbonate (Boc anhydride) (20.11 g, 92.2 mmol) in 100 mL THF was added a catalytic amount of 4-(dimethylamino)pyridine (DMAP). The reaction mixture was allowed to stir for 90 minutes, and then the solvent was evaporated in vacuo to yield a thick oil. The oil was dissolved in THF (46 mL) and heated to 65° C. for 18 hours. Solid sodium hydroxide (1.8 g, 46.1 mmol) was added to the reaction mixture and heating was continued for 4 hours; then the THF was evaporated. The yellow colored solid was dissolved in EtOAc, washed with water, and the organic layer was evaporated and purified by column chromatography using EtOAc/hexane (10:90) to yield the desired product (11 g, 75% yield). $^1$H NMR: (400 MHz, DMSO-$d_6$) δ (ppm): 9.62 (s, 1H), 7.98 (d, J=2.2 Hz, 1H), 7.76 (dd, J=8.6, 2.2 Hz, 1H), 7.55 (d, J=8.8 Hz, 1H), 1.44 (s, 9H).

Synthesis of tert-butyl (2-nitro-4-(thiophen-2-yl) phenyl)carbamate (8a)

This compound was synthesized following the reported procedure with little modification (WO 2009/055917). A suspension of 2-thiophene boronic acid (0.22 g, 0.694 mmol), bromoarene 7 (0.118 g, 0.922 mmol), tri-o-tolylphosphine (0.069 g, 0.22 mmol), and potassium carbonate (0.288 g, 2.082 mmol) in degassed dimethoxyethane (DME) (1.8 mL) and water (0.6 mL) was treated with tetrakis(triphenylphosphine)(0) (0.052 g, 0.045 mmol). The reaction mixture was exposed to microwave at 80° C. for 30 minutes. After cooling, the reaction mixture was diluted with ethyl acetate, washed with brine, dried over MgSO$_4$ and concentrated. The crude material was purified with column chromatography (10% EtOAc in hexane) to give the title compound (0.18 g, 81% yield). $^1$H NMR: (400 MHz, DMSO-$d_6$) δ (ppm): 9.59 (s, 1H), 8.10 (d, J=2.2 Hz, 1H), 7.91 (dd, J=8.4, 2.2 Hz, 1H), 7.61-7.58 (m, 2H), 7.57-7.53 (m, 1H), 7.13 (dd, J=4.8, 3.2 Hz, 1H), 1.43 (s, 9H).

Synthesis of tert-butyl (3-nitro-[1,1'-biphenyl]-4-yl) carbamate (8b)

That compound was synthesized following the same procedure as described for 8a. The suspension of phenyl boronic acid (0.865 g, 7.1 mmol), bromoarene 7 (1.5 g, 4.7 mmol), tri-o-tolyl-phosphine (0.446 g, 1.5 mmol), and potassium carbonate (1.96 g, 142 mmol) in degassed dimethoxyethane (DME) (9 mL) and water (3 mL) was treated with tetrakis(triphenylphosphine)(0) (0.410 g, 0.36 mol). The reaction mixture was exposed to microwave at 80° C. for 30 minutes. After cooling, the reaction mixture was diluted with ethyl acetate, washed with brine, dried over MgSO$_4$, and concentrated. The crude material was purified with column chromatography (5% EtOAc in hexane) to give the title compound (1.085 g, 72.4% yield). $^1$H NMR (400 MHz, Chloroform-d) δ 9.67 (s, 1H), 8.63 (d, J=8.9 Hz, 1H), 8.42 (s, 1H), 7.87-7.82 (m, 1H), 7.62-7.57 (m, 2H), 7.50-7.44 (m, 2H), 7.42-7.37 (m, 1H), 1.56 (s, 9H).

Synthesis of tert-butyl (2-amino-4-(thiophen-2-yl) phenyl)carbamate (9a)

Compound 9a was made following the procedure reported in the patent literature (WO 2009/055917). Compound 8a (0.24 g, 0.75 mmol) was placed in a round bottom flask and 10% palladium on carbon (catalytic amount, 20 mg) was added into it. The reaction mixture was exposed to a H$_2$ balloon. After purging with H$_2$, the reaction mixture was stirred under H$_2$ balloon for 2 hours at room temperature. It was then filtered through Celite and concentrated under vacuum to give the desired amine (0.217 g, 100% yield). $^1$H NMR (400 MHz, Chloroform-d) δ 7.33-7.27 (m, 1H), 7.25-7.21 (m, 2H), 7.08-7.03 (m, 2H), 7.02 (d, J=2.0 Hz, 1H), 1.52 (s, 9H).

Synthesis of tert-butyl (3-amino-[1,1'-biphenyl]-4-yl)carbamate (9b)

Compound 9b was made following the same procedure described for 9a. Synthesized intermediate 8a (0.27 g, 0.86 mmol) was used to give a quantitative yield (0.244 g) of title compound 9b. $^1$H NMR: (400 MHz, CDCl$_3$) δ (ppm): $^1$H NMR (400 MHz, Chloroform-d) δ 7.55-7.51 (m, 2H), 7.40 (dd, J=8.2, 6.7 Hz, 2H), 7.34-7.31 (m, 2H), 7.04 (m, 1H), 6.99 (d, J=2.0 Hz, 1H), 1.53 (s, 9H).

Example 2—Preparation of Compounds

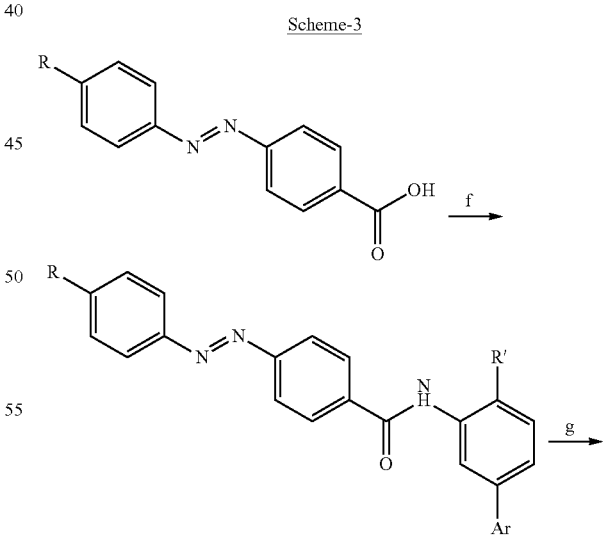

Scheme-3

10a: R═H; R'═NH$_2$; Ar═H
10b: R═N(CH$_3$)$_2$; R'═NH$_2$; Ar═H
10c: R═N(CH$_3$)$_2$; R'═OH; Ar═H
10d: R═COOH; R'═NH$_2$; Ar═H
10e: R═N(CH$_3$)$_2$; R'═OH; Ar═C$_4$H$_3$S
10f: R═N(CH$_3$)$_2$; R'═NHBoc; Ar═C$_4$H$_3$S
10g: R═N(CH$_3$)$_2$; R'═NHBoc; Ar═C$_6$H$_5$

-continued

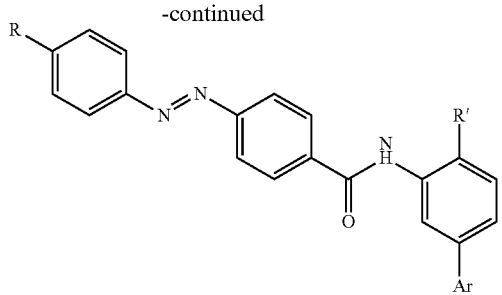

11a: R=N(CH₃)₂; R'=NH₂; Ar=C₄H₃S
11b: R=N(CH₃)₂; R'=NH₂; Ar=C₆H₅

Reagents & conditions: (f) i. aryl-amines, ii. EDCl, iii. DMAP (cat. amt), iv. dichloromethane/pyridine (1:1), 2 h, RT, (g) i. TFA/DCM (30:70), RT, 30 min, ii. aq NaHCO3

Scheme-4

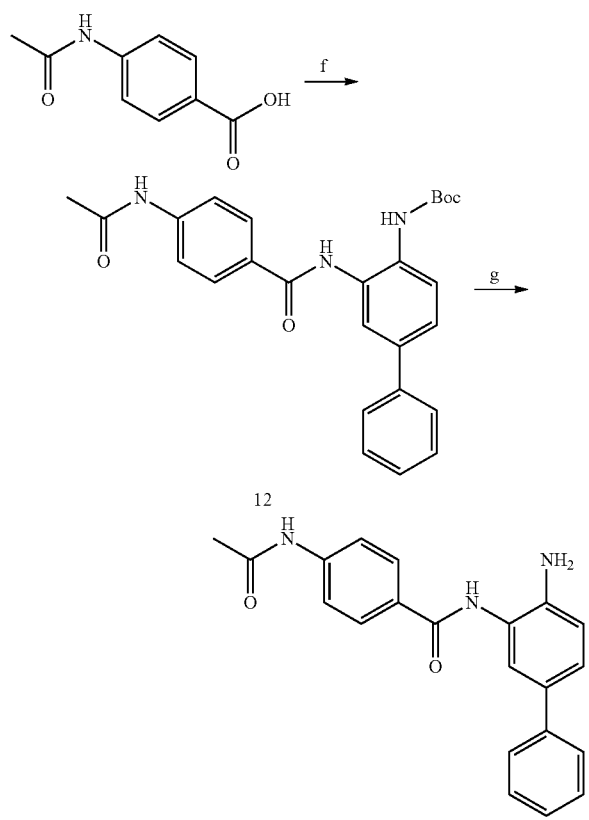

General Procedure Followed for the Aromatic Acid and Amine Coupling Reactions (A);

This procedure was followed for aromatic acid and aromatic amine coupling reactions where the aromatic acids containing unsubstituted or 4' substituted diphenyl-diazene moiety were suspended in dichloromethane/pyridine (1:1) mixture and 1-ethyl-3-(3-dimethylaminopropyl)carbodiimide) (EDCI) was added into it and stirred for 10 minutes. To this stirring solution, amines and a catalytic amount of 4-DMAP were added at room temperature and stirring was continued to 2 hours. The reaction mixture was evaporated and the crude mixture was resuspended into ethyl acetate and extracted from an aqueous NaHCO₃ solution. After evaporating the EtOAc layer, the title compounds were purified by column chromatography using ethyl acetate hexane mixture that ratio was determined from analytical silica gel-coated TLC plates (Silica Gel 60 $F_{254}$).

Synthesis of N-(2-aminophenyl)-4-(phenyldiazenyl)benzamide (10a)

Compound 10a was synthesized following the general acid-amine coupling reaction (A) described above where 4-(phenylazo)benzoic acid (0.2 g, 0.884 mmol) was treated with o-phenylenediamine (0.287 g, 2.65 mmol) to yield final compound 10a (0.23 g, 82% yield). $^1$H NMR: (400 MHz, DMSO-$d_6$) δ (ppm): 9.83 (s, 1H), 8.19 (d, J=7.2 Hz, 2H), 7.98 (d, J=7.2 Hz, 2H), 7.93 (d, J=6 Hz, 2H), 7.59 (m, 3H), 7.17 (d, J=7.2 Hz, 1H), 6.98 (t, J=6.8 Hz, 1H), 6.78 (d, J=7.6, 1H), 6.6 (t, J=6.8 Hz, 1H). $^{13}$C NMR (101 MHz, dmso) δ 164.99, 153.79, 152.35, 143.74, 137.30, 132.50, 130.02, 129.59, 127.26, 127.12, 123.44, 123.22, 122.75, 116.62, 116.51.

Synthesis of N-(2-aminophenyl)-4-((4-(dimethylamino)phenyl)diazenyl)benzamide (10b)

Compound 10b was made following the same procedure described for 10a. 4-Dimethylamino azobenzene-4'-carboxylic acid (0.25 g, 0.93 mmol) was treated with o-phenylenediamine (0.301 g, 2.78 mmol) to give the final compound 10b (0.247 g, 74% yield). $^1$H NMR: (400 MHz, DMSO-$d_6$) δ (ppm): 9.8 (s, 1H), 8.12 (d, J=8 Hz, 2H), 7.86 (t, J=9 Hz, 4H), 7.17 (d, J=7.6 Hz, 1H), 6.99 (t, J=7.2 Hz, 1H), 6.85 (d, J=9.2 Hz, 2H), 6.79 (d, J=8 Hz, 1H), 6.62 (t, J=7.6 Hz, 1H), 4.91 (s, 2H), 3.06 (s, 6H). $^{13}$C NMR (101 MHz, dmso) δ 165.15, 154.54, 153.30, 143.68, 143.07, 135.28, 129.41, 127.20, 127.00, 125.59, 123.66, 121.92, 116.66, 116.54, 112.02.

Synthesis of 4-((4-(dimethylamino)phenyl)diazenyl)-N-(2-hydroxyphenyl)benzamides (10c)

Compound 10c was also made following the general procedure A. To a suspension of 4-dimethylamino-azobenzene-4'-carboxylic acid (0.308 g, 1.145 mmol), 2-aminophenol (0.05 g, 0.458 mmol) was added. After the completion of the reaction, the solution was evaporated and resuspended in dichloromethane and then washed with water and neutralized with 0.1 (N) aqueous NaOH. The organic layer was evaporated and the crude mixture was purified by column chromatography using 5% methanol in ethyl acetate to yield the desired compound 10c (0.142 g, 86% yield). $^1$H NMR (400 MHz, DMSO-d6) δ 9.73 (s, 1H), 9.61 (s, 1H), 8.10 (d, J=8.6 Hz, 2H), 7.89-7.73 (m, 4H), 7.71-7.62 (m, 1H), 6.93 (d, J=1.4 Hz, 1H), 6.84 (dd, J=9.4, 2.2 Hz, 3H), 3.07 (s, 6H). $^{13}$C NMR (101 MHz, dmso) δ 165.09, 154.69, 153.34, 150.00, 143.08, 134.95, 129.20, 126.28, 126.21, 125.63, 124.86, 122.11, 119.46, 116.46, 112.03.

Synthesis of 4-((4-((2-aminophenyl)carbamoyl)phenyl)diazenyl)benzoic Acid (10d)

This compound was made following the procedure A where o-phenylenediamine (0.04 g, 0.37 mmol) and azobenzene-4,4'-dicarboxylic acid (0.10 g, 0.37 mmol) were used to get the title compound 10d (0.025 g, 19% yield). $^1$H NMR: (400 MHz, DMSO-$d_6$) δ (ppm): 8.21-8.19 (d, J=8 Hz, 1H), 8.14-8.12 (m, 2H), 8.02-8.00 (d, J=8 Hz, 1H), 7.97-7.93 (m, 3H), 7.82-7.80 (d, J=8 Hz, 1H), 7.19-7.17 (d, J=8 Hz, 1H), 6.99-6.92 (m, 2H), 6.79-6.76 (d, J=12 Hz, 1H), 6.09-6.00 (m, 1H). $^{13}$C NMR (101 MHz, dmso) δ 172.48, 167.51, 164.98, 154.06, 153.79, 143.74, 137.64, 130.92, 130.54, 129.63, 127.97, 127.27, 123.41, 122.96, 122.93, 120.11, 116.59, 116.49.

Synthesis of 4-((4-(dimethylamino)phenyl)diazenyl)-N-(2-hydroxyphenyl)benzamides (10e)

This compound was synthesized following the same procedure used to make compound 10c. 4-Dimethylaminoazobenzene-4'-carboxylic acid (0.211 g, 0.784 mmol) and 2-amino-4-(thiophen-2-yl)phenol were exposed to the coupling reaction to yield the desired final compound 10e (0.73 g, 65% yield). $^1$H NMR (400 MHz, DMSO-d6) δ 8.16-8.04 (m, 2H), 8.00 (d, J=2.3 Hz, 1H), 7.90-7.77 (m, 4H), 7.43 (dd, J=5.1, 1.2 Hz, 1H), 7.39-7.28 (m, 2H), 7.08 (dd, J=5.1, 3.5 Hz, 1H), 6.96 (d, J=8.3 Hz, 1H), 6.83 (dd, J=9.2, 4.0 Hz, 2H), 3.06 (d, J=1.2 Hz, 6H). $^{13}$C NMR (101 MHz, dmso) δ 165.21, 154.76, 153.35, 149.88, 144.06, 143.10, 134.80, 130.84, 129.26, 128.79, 126.68, 125.79, 125.65, 125.51, 124.74, 122.60, 122.31, 122.13, 121.98, 116.94, 112.03.

Synthesis of N-(2-amino-5-(thiophen-2-yl)phenyl)-4-((4-(dimethylamino)phenyl)diazenyl)benzamide (11a)

Compound 10f was prepared following the procedure A where 4-dimethylamino-azobenzene-4'-carboxylic acid (0.110 g, 0.408 mmol) was treated with tert-butyl (2-amino-4-(thiophen-2-yl)phenyl)carbamate (9a) (0.13 g, 0.449 mmol) to prepare the anilinic amine Boc protected intermediate 10f which was purified by column chromatography using 25% EtOAc in hexane solvent system. Boc deprotection of 10f was carried out using trifluoroacetic acid and dichloromethane mixture (30:70) to get desired final compound 11a (0.096 g, 53% yield). $^1$H NMR (400 MHz, DMSO-d6) δ 8.16-8.04 (m, 2H), 8.00 (d, J=2.3 Hz, 1H), 7.90-7.77 (m, 4H), 7.43 (dd, J=5.1, 1.2 Hz, 1H), 7.39-7.28 (m, 2H), 7.08 (dd, J=5.1, 3.5 Hz, 1H), 6.96 (d, J=8.3 Hz, 1H), 6.83 (dd, J=9.2, 4.0 Hz, 2H), 3.06 (d, J=1.2 Hz, 6H). $^{13}$C NMR (101 MHz, dmso) δ 165.33, 154.60, 153.31, 144.67, 143.60, 143.08, 135.14, 129.49, 128.67, 125.61, 124.47, 123.71, 123.65, 122.64, 121.92, 121.45, 116.78, 112.03.

Synthesis of N-(4-amino-[1,1'-biphenyl]-3-yl)-4-((4-(dimethylamino)phenyl)diazenyl)benzamide (11b)

This compound was made using the same synthetic protocol used to make compound 11a. 4-Dimethylaminoazobenzene-4'-carboxylic acid (0.18 g, 0.67 mmol) acid and tert-butyl (3-amino-[1,1'-biphenyl]-4-yl)carbamate (9b) (0.256 g, 1.34 mmol) were used to make the intermediate compound 10g and Boc deprotection of this compound gave the final compound 11b (0.134 g, 46% overall yield). $^3$H NMR (400 MHz, DMSO-d6) δ 9.85 (s, 1H), 8.15 (d, J=8.2 Hz, 2H), 7.90-7.79 (m, 4H), 7.59-7.50 (m, 3H), 7.42-7.29 (m, 3H), 7.23 (d, J=7.3 Hz, 1H), 6.86 (t, J=9.3 Hz, 3H), 5.13 (s, 2H), 3.07 (s, 6H). $^{13}$C NMR (101 MHz, dmso) δ 165.31, 154.58, 153.31, 143.36, 143.08, 140.61, 135.25, 129.47, 129.24, 128.51, 126.45, 125.93, 125.60, 125.32, 125.23, 123.91, 121.93, 116.93, 112.03.

Synthesis of 4-acetamido-N-(4-amino-[1,1'-biphenyl]-3-yl)benzamides (13)

To make the compound 13, the above described general acid-amine coupling reaction conditions (A) had been followed. 4-acetamidobenzoic acid (0.044 g, 0.25 mmol) was treated with tert-butyl (3-amino-[1,1'-biphenyl]-4-yl)carbamate (9b) (0.07 g, 0.25 mmol) to make compound 12 which was the exposed to Boc deprotection conditions and purified by column chromatography using 30% ethylacetate in hexane get final compound 13 (0.063 g, 74% overall yield). $^1$H NMR (400 MHz, DMSO-d6) δ 10.19 (s, 1H), 9.62 (s, 1H), 7.95 (d, J=8.3 Hz, 2H), 7.69 (d, J=8.4 Hz, 2H), 7.52 (dd, J=15.1, 4.9 Hz, 3H), 7.41-7.17 (m, 4H), 6.85 (d, J=8.3 Hz, 1H), 5.06 (s, 2H), 2.07 (s, 3H). $^{13}$C NMR (101 MHz, dmso) δ 169.18, 165.32, 143.21, 142.58, 140.63, 129.23, 129.16, 128.56, 126.43, 125.93, 125.19, 125.01, 124.17, 118.45, 116.95.

Example 3—Compound Activity

IC$_{50}$ Assay

The inhibitory effect on deacetylase activity for the compounds provided herein was determined using the conditions from a published optimized biochemical assay (see, e.g., Bradner, J. E. et al., *Nature Chemical Biology*, 2010, 6, 238-243; and Bowers, A. et al., *J Am Chem Soc* 2008, 130, 11219-11222). Compounds were added to white 96-well plates containing 40 μL of HDAC assay buffer (50 mM HEPES, 100 mM KCl, 0.05% BSA, 0.001% Tween-20 at pH 7.4) by pin transfer. To the assay plate was added 40 μL of a stock solution of full-length HDAC protein at three times the desired final concentration. After addition the plate was centrifuged to mix the solution while removing air bubbles. Our 470 nm (22.9V/0.2 A) LED 96-well excitation device (FIG. 4) was fitted atop of the assay plate inducing photoisomerization to the cis isomer of the compounds while preincubating with the enzyme for 1 hour. After which 40 μL of an HDAC buffer solution containing 3× trypsin and 3× the Km concentration of substrate was added. The plate was centrifuged and immediately read on a Tecan Satire II plate reader (ex. 345 nm, em 440 nm, Gain 60) representing the initial read for start of the assay. After which, reads were taken every 15 minutes to follow the fluorogenic release of 7-amino-4-methylcoumarin from the substrate resulting from deacetylase and trypsin enzymatic activity. In between reads the LED excitation device was reaffixed on top of the plate ensuring maximum cis-isomer population. In parallel to this, a second plate was prepared identically and measured for activity but this plate was not excited by our device but rather was covered to prevent any ambient light from shining on the plate. Replicate pairs of plates were performed.

Half-Life Experiment

To directly compare the residence time versus isoform relaxation time BG47 and BG48 were incubated with HDAC1 in alternating columns of a white 96-well plate. Columns 1 and 2 were exposed to 470 nm light (22.9V/0.2 A; 0.1 A per column) from LEDs using our excitation device 17 hours before the assay for 1 hour, resulting in 16 hours of relaxation time before the assay. Columns 3 and 4 were exposed to light 9 hours before the assay for 1 hour providing an 8 hour relaxation period and columns 5 and 6 were exposed 5 hours before the assay providing a 4 hour relaxation time point while columns 11 and 12 were used as controls with no pre-exposure. After the completion of the pre-exposure and relaxation time points a stock solution of trypsin and substrate was added to the plate. The plate was centrifuged and read using a Tecan Safire II every 2 minutes while keeping the plate inside the instrument, eliminating exposure to ambient light.

Figure 4:
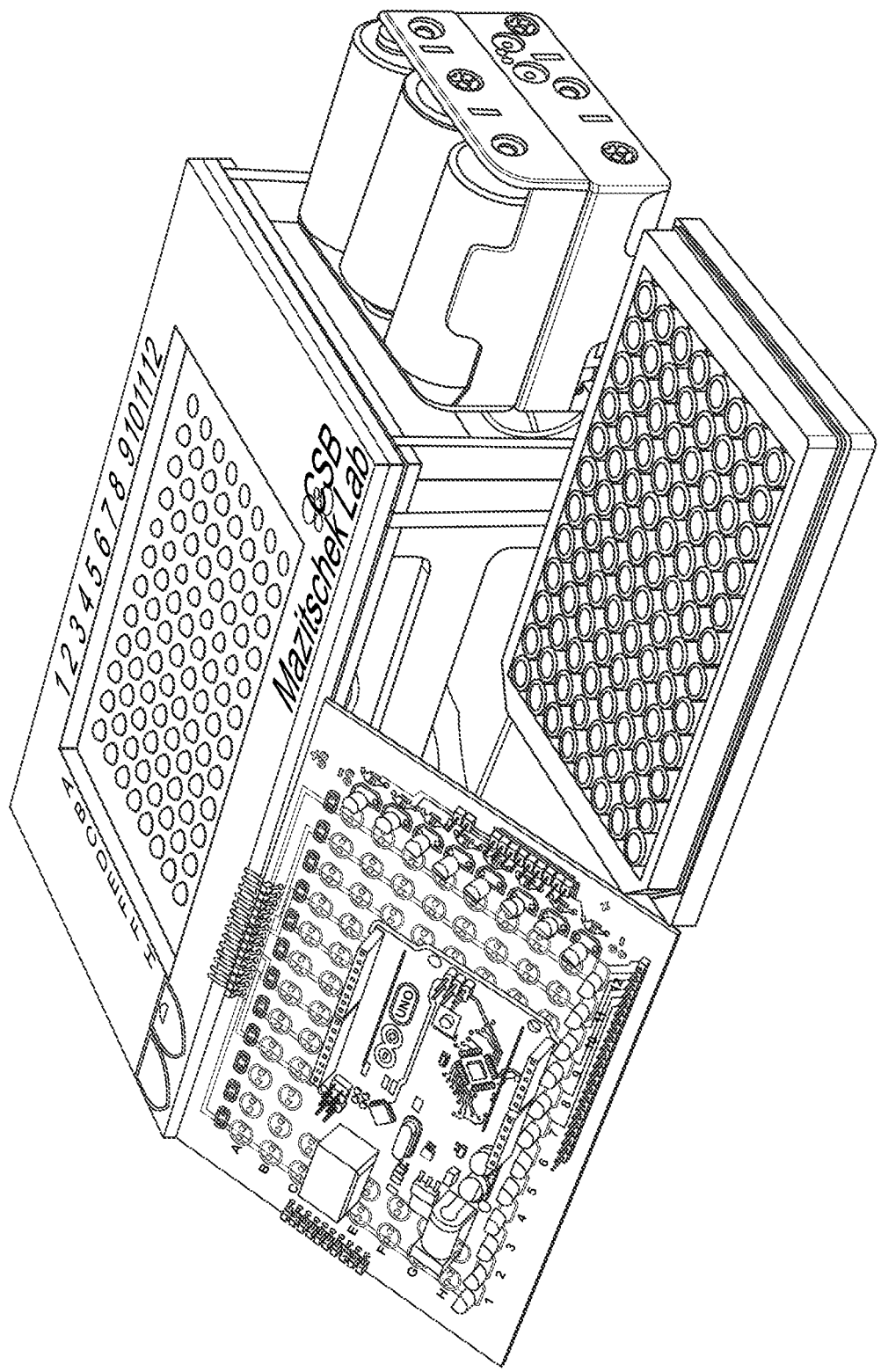
FIG. 4 shows a 12×8 LED array developed to match standardized microtiter plate layouts.

To allow for high throughput profiling in 96-well microtiter plate format a 12×8 LED array was developed to match the standardized microtiter plate layout (FIG. 4). The LED arrays were connected to a micro controller that was programmed to control individual LEDs, LED rows, or LED columns within the array. The controller allowed for modulation of LED intensity by controlling the on/off timing (PWM) or by directly controlling the supplied voltage. The temporal control was <10 ms. The LEDs and microcontroller were powered optionally by a power supply unit connected to a standard 110 V outlet or by a battery-pack, which allowed for use in a cell culture incubator. The LED array was used as lid to illuminate plates from the top and as a stage to illuminate the plates from the bottom, as required by the experimental setup.

Compounds were profiled physically to determine absorbance spectra, solubility and kinetics of photo-isomerization kinetics and thermal relaxation (where applicable). The compounds were then profiled biochemically to determine the HDAC inhibitory profile as a function of light exposure. Finally, selected compounds were profiled in cellular assays for the ability to induce hyperacetylation of histone proteins, which represents a biomarker readout for HDAC inhibition.

Figure 5:
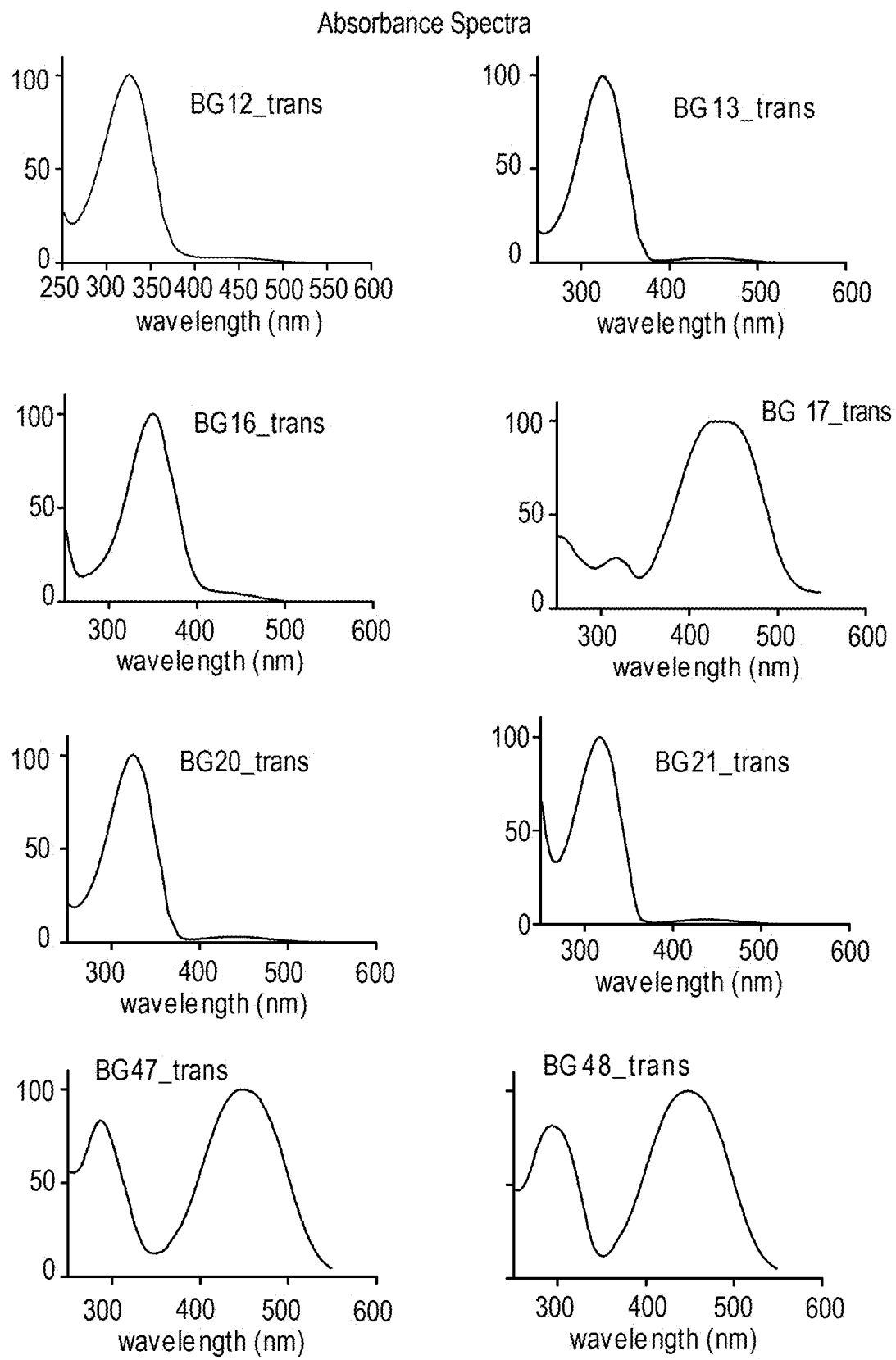
FIG. 5 illustrates the absorbance spectra of selected compounds described herein (BG14, BG18, BG12, and BG19).
Figure 5:
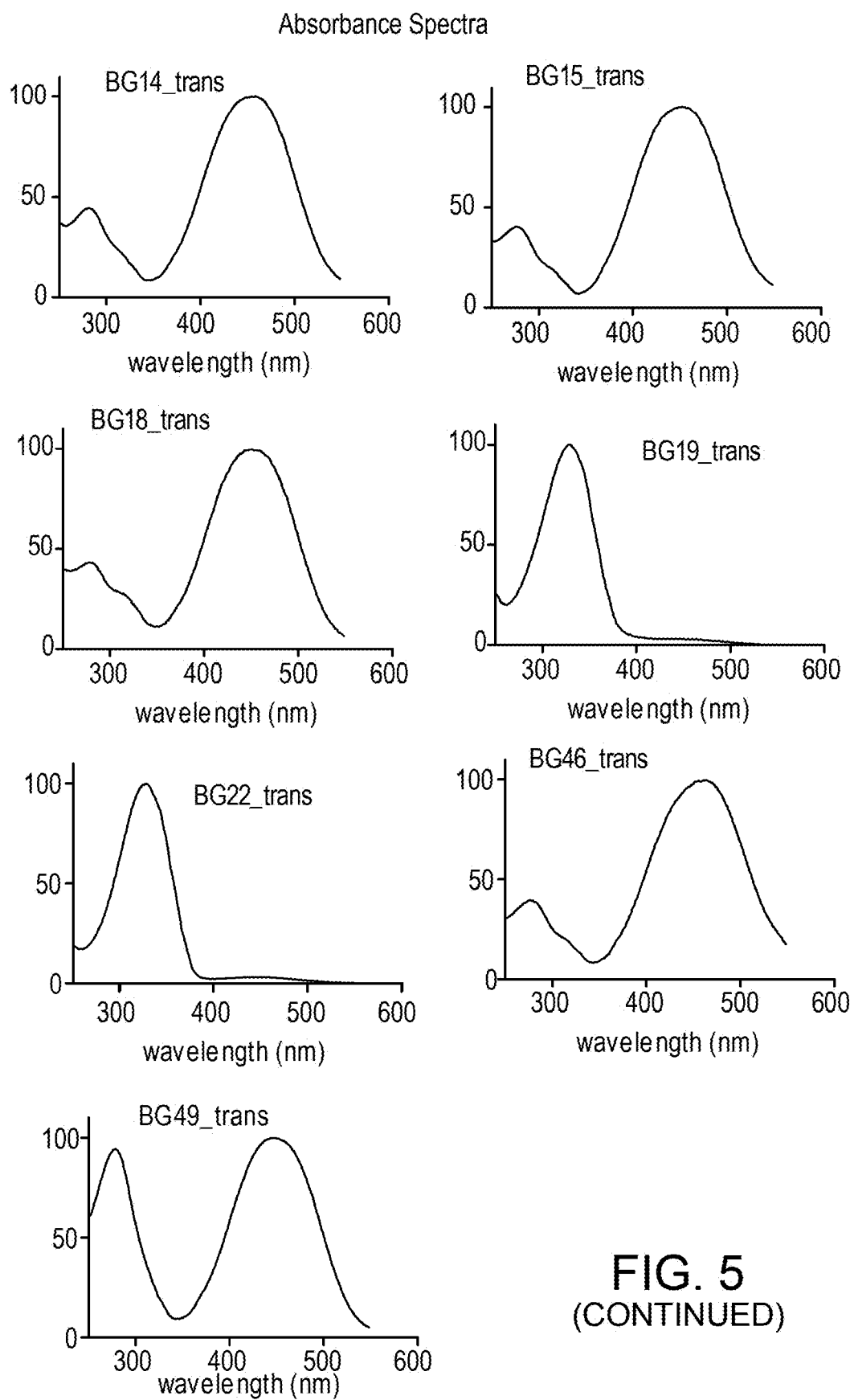

Compounds studied include those analogs with a push-pull azobenzene system (BG14, BG18, BG47, BG48 and BG49). These compounds absorbed in the blue range of the visible spectrum, shown in FIG. 5 for BG14 and BG18. In contrast BG12 and BG19, which do not feature a push-pull system, maximally absorbs in the UV range (FIG. 5).

Figure 6:
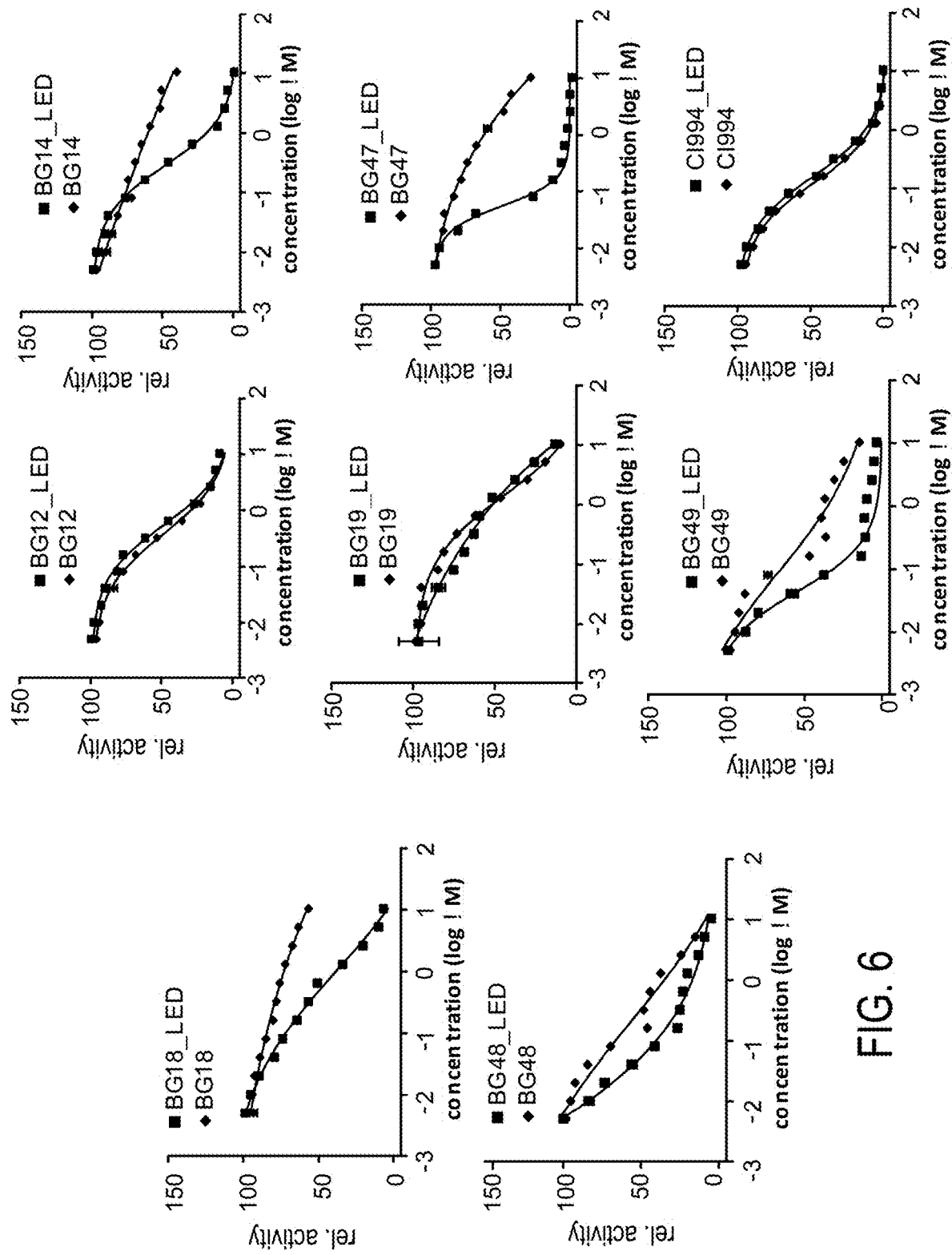
FIG. 6 shows the inhibitory activity of selected compounds against HDAC1 with and without exposure (including 1 hr pre-exposure) to 470 nm light.
Figure 7:
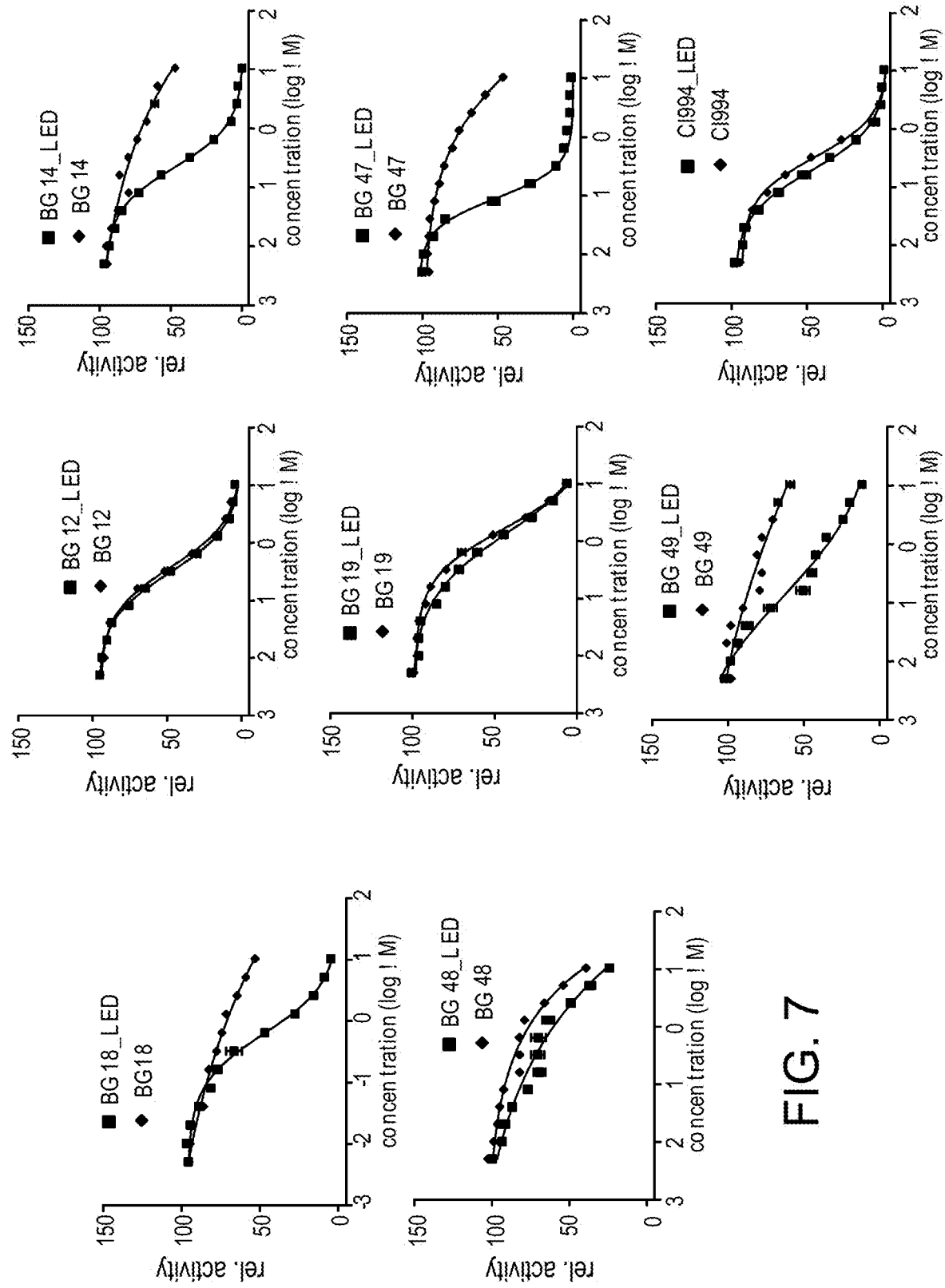
FIG. 7 shows the inhibitory activity of selected compounds against HDAC2 with and without exposure (including 1 hr pre-exposure) to 470 nm light.
Figure 8:
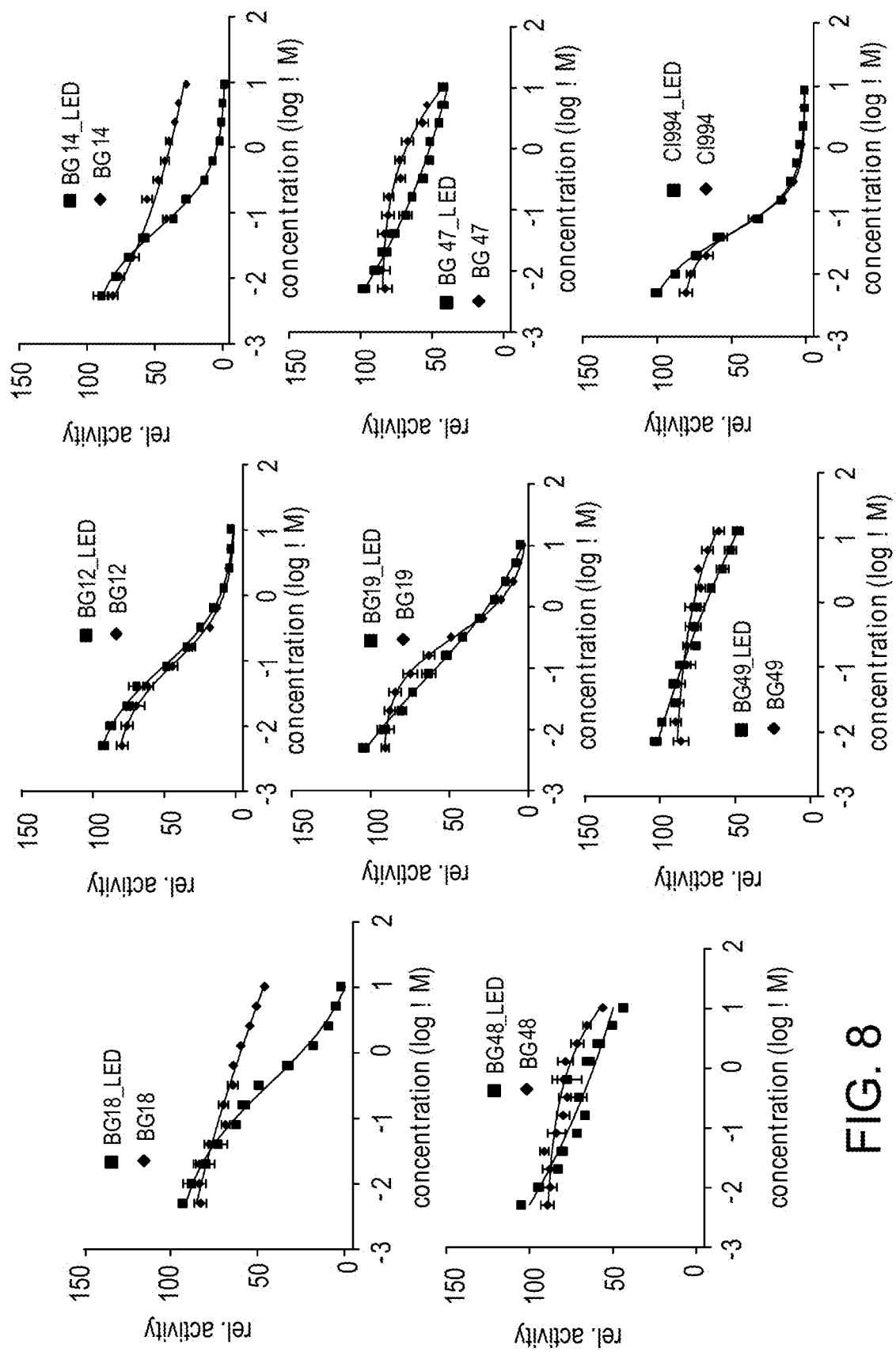
FIG. 8 shows the inhibitory activity of selected compounds against HDAC3 with and without exposure (including 1 hr pre-exposure) to 470 nm light.

The compound panel was also profiled for inhibitory activity against HDAC1-3 with and without exposure (including 1 hr pre-exposure) to 470 nm light (FIGS. 6-8). Significantly increased activity was observed for BG14, BG18, BG47, BG48 and BG49 in samples exposed to light, while no differential activity was seen for the control compound CI-994.

Figure 9:
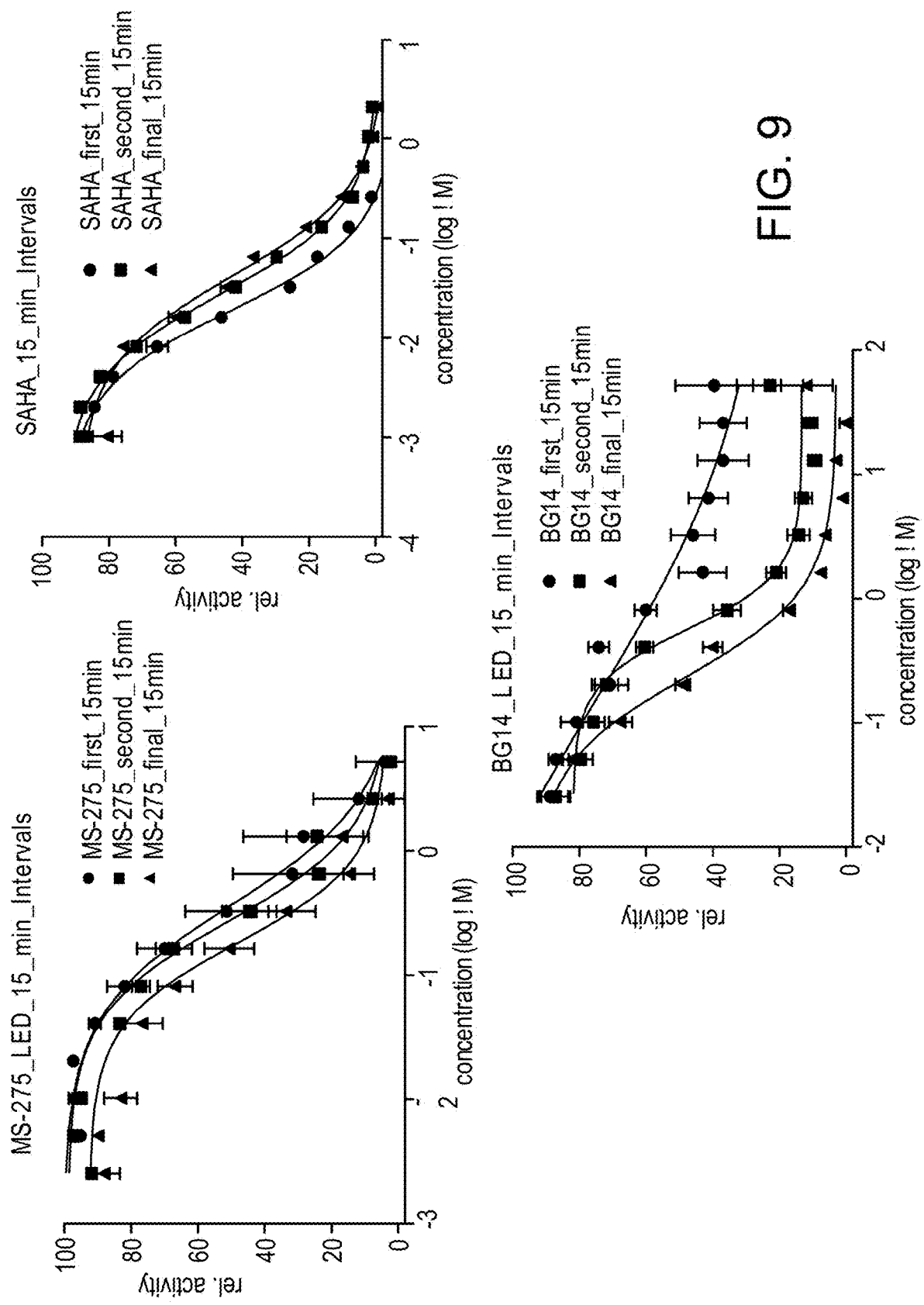
FIG. 9 compares the activity change of BG14 and the reference HDAC inhibitors MS-275 and SAHA as a function of light exposure time.

The activation of the photoswitchable inhibitors depends on the light energy and the exposure time (as predicted by our model). FIG. 9 compares the activity change of BG14 and the reference HDAC inhibitors MS-275 and SAHA as a function of exposure time. Following pre-incubation of the HDAC enzyme and respective small molecule inhibitor, the enzyme substrate was added and the assay plate was continuously exposed to light (470 nm). Inhibitory activities were measured in 15 min intervals. Only compound BG14 shows increased activity with increased exposure time.

Figure 10:
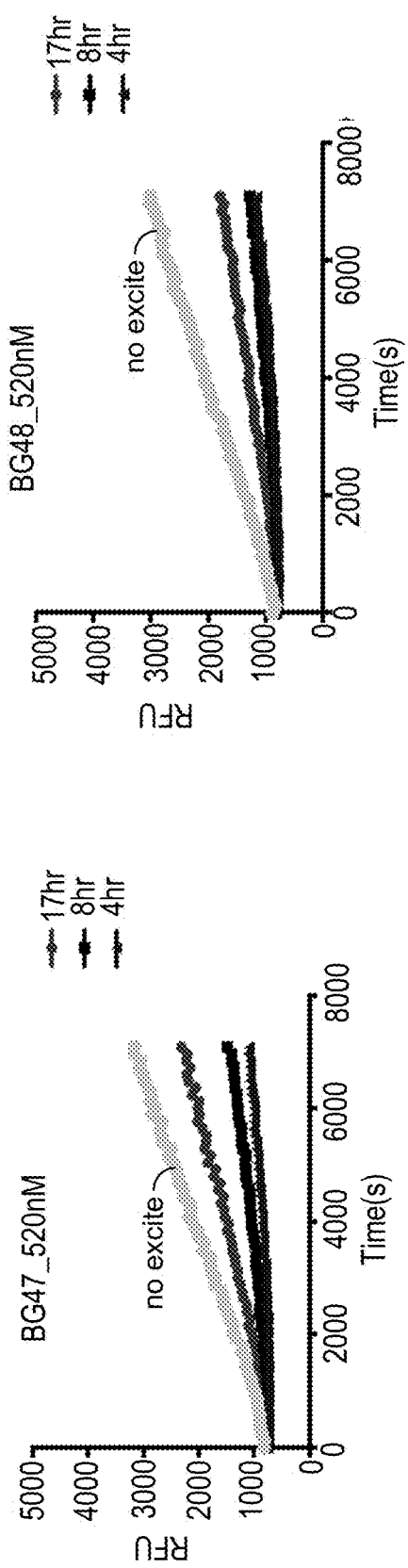
FIG. 10 illustrates the long residence time of the compounds once engaged with an HDAC enzyme as shown for BG47 and BG48.

The benzamide inhibitors exhibit long residence time once engaged with the respective HDAC enzyme as shown for BG47 and BG48 (FIG. 10). Both compounds were incubated at 520 nM with HDAC1, exposed for 1 hour of 470 nM light and stored in the dark for 4, 8 and 17 hours, respectively, followed by addition of enzyme substrate. The activity was monitored in reference to unexposed compound with continuous readout measured over 2 hours, estimating a residence half-live of 12-24 hours.

Figure 11:
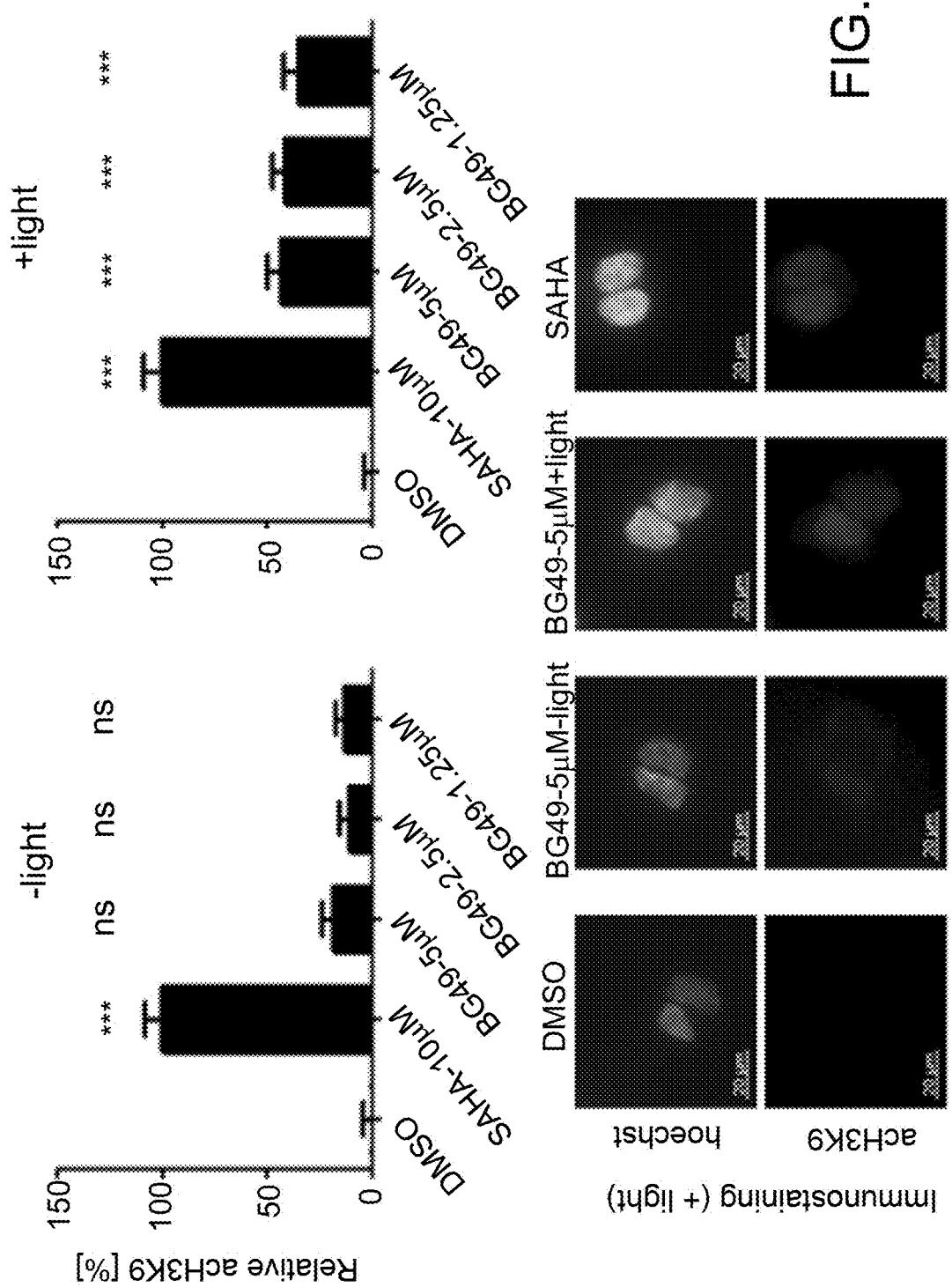
FIG. 11 shows the activity of the compounds in live cells using acetylation of histone H3 Lysine 9 as a biomarker for HDAC inhibition (immunofluorescent staining).
Figure 12:
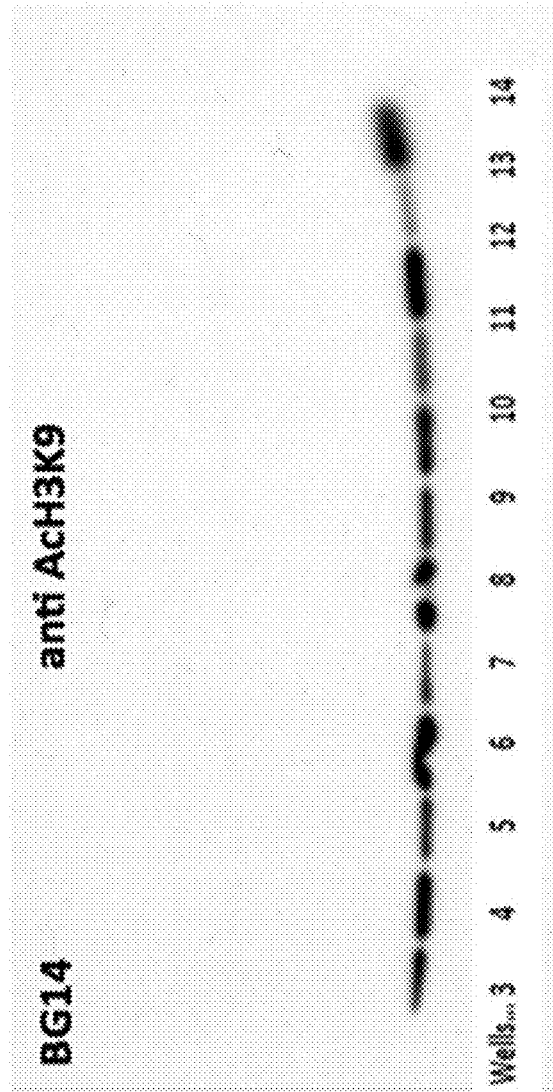
FIG. 12 shows the activity of the compounds in live cells using acetylation of histone H3 Lysine 9 as a biomarker for HDAC inhibition. (western blotting)
Figure 12:
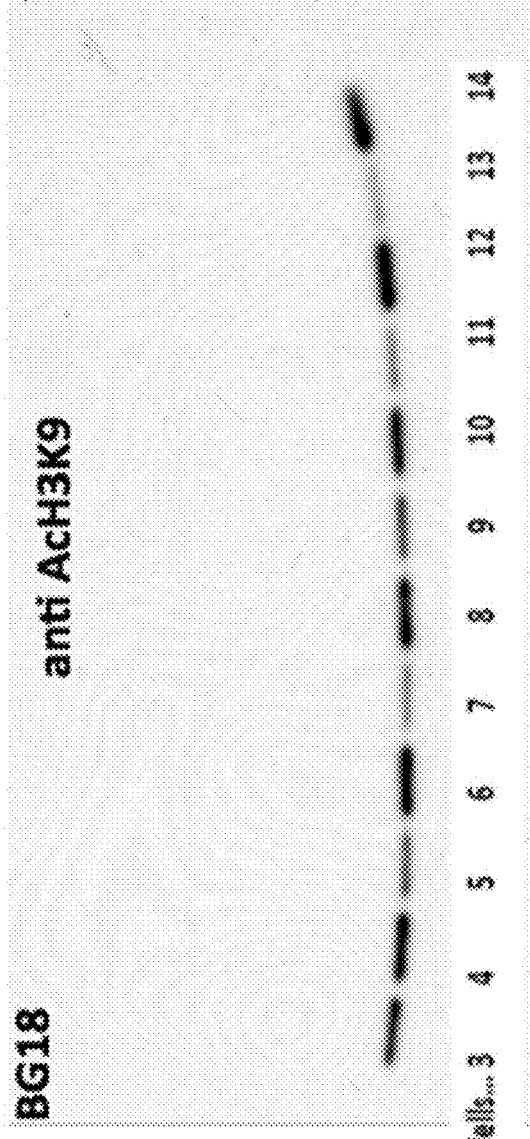
Figure 12:
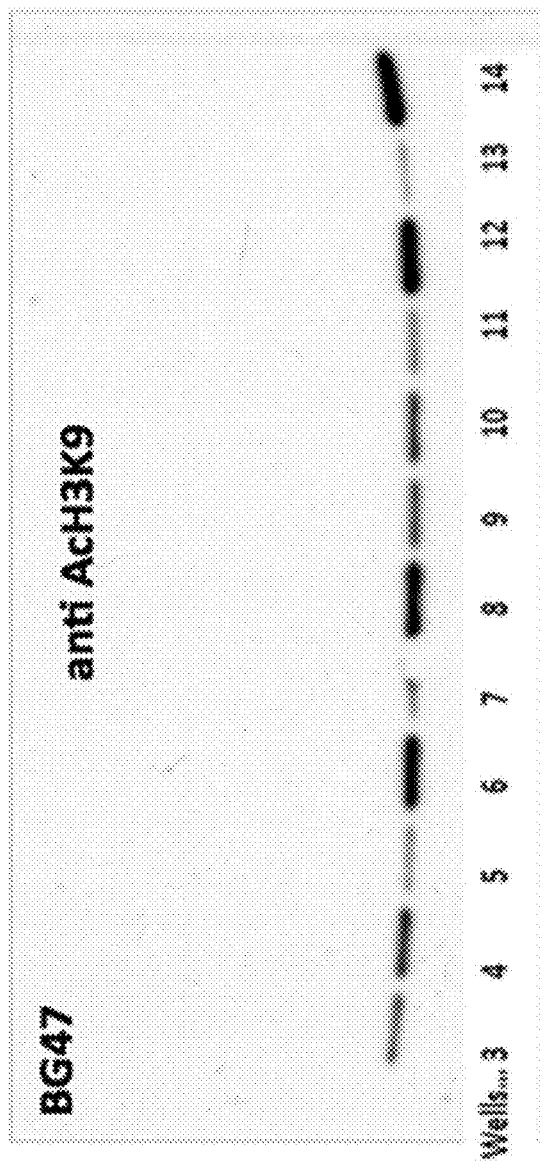
Figure 12:
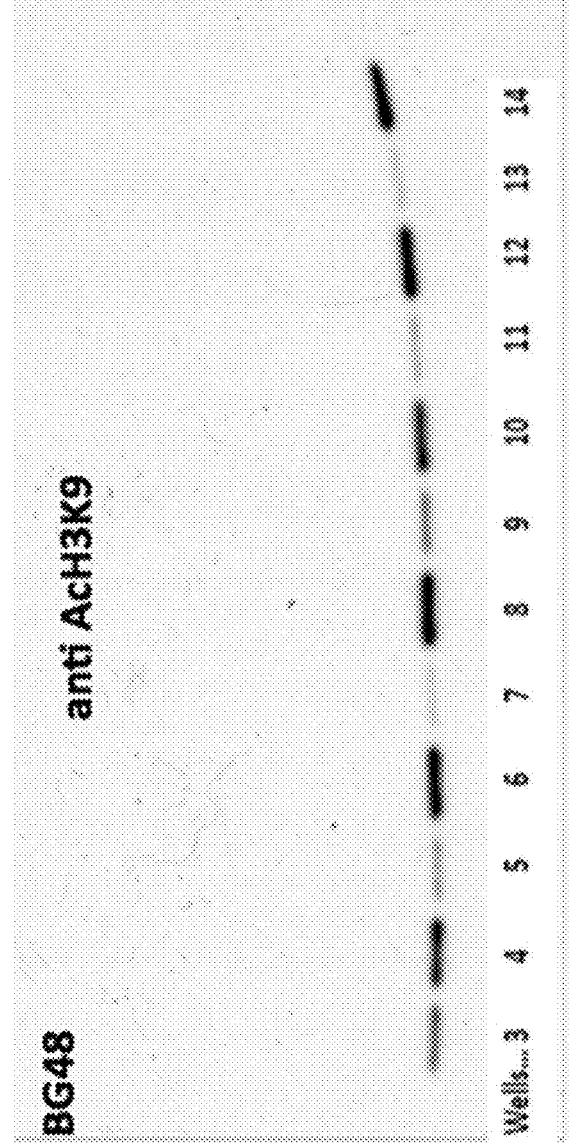

The activity of the compounds in live cells was validated using acetylation of histone H3 Lysine 9 as a biomarker for HDAC inhibition. As shown in FIG. 11, using BG49 as a model compound, statistically significant induced hyperacetylation of H3K9 relative to DMSO control was observed only following light exposure. The stronger induction by SAHA is the consequence of additional inhibition of HDAC3, which is not targeted by BG49.

Example 4—Preparation of Compounds

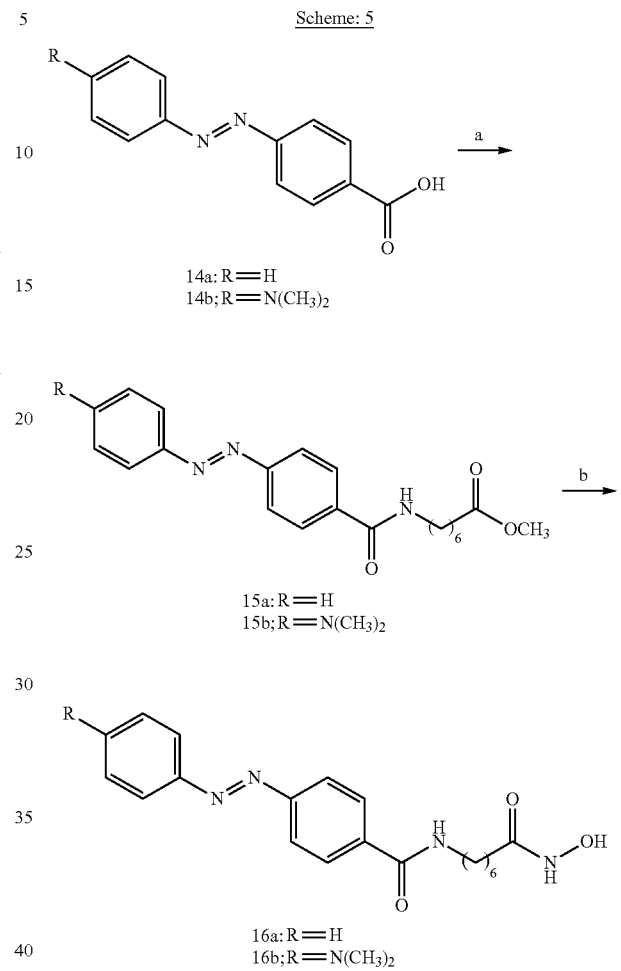

Reagents and conditions: (a). Methyl 7-aminoheptanoate, PyBOP, DIPEA (N,N′–diisopropylethyldiamine), CH$_2$Cl$_2$, 1 h, RT. (b). 50% NH$_2$OH (aq), 1 (N) NaOH (MeOH), room temp, 30 min

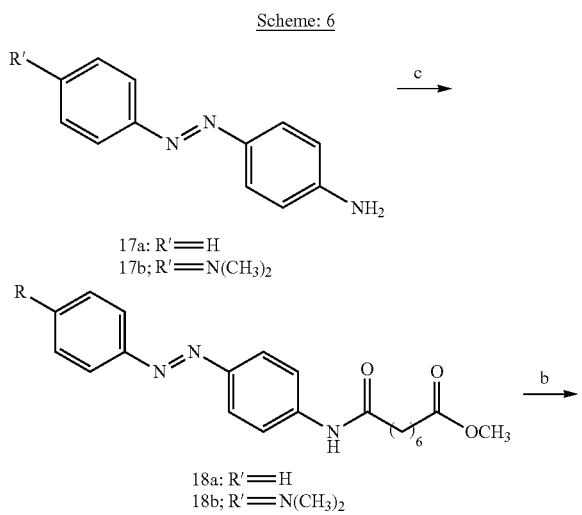

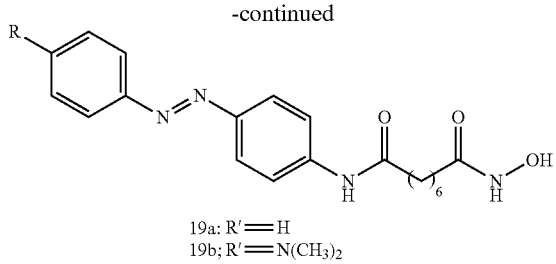

19a: R' = H
19b; R' = N(CH₃)₂

Reagents and conditions: (a). methyl 8-chloro-8-oxooctanoate, Et₃N, CH₂Cl₂, room temo, 1 h. (b). 50% NH₂OH (aq), 1 (N) NaOH (MeOH), room temp, 30 min

Synthesis of Methyl 7-(4-(phenyldiazenyl)benzamido)heptanoate (15a)

Compound 15a was synthesized by acid amine coupling reaction using PyBOP as a coupling reagent. In a 50 mL round bottom flask, commercially available 4-(phenyldiazenyl)benzoic acid (0.10 g, 0.442 mmol) was suspended in 20 mL of dry dichloromethane and methyl 7-aminoheptanoate (0.07 g, 0.442 mmol) was added into it. In the reaction vessel PyBOP (benzotriazol-1-yl-oxytripyrrolidinophosphonium hexafluorophosphate) (0.28 g, 0.53 mmol) and DIPEA (N,N'-diisopropylethyldiamine) (0.085 mL, d=0.742 g/mL, 0.47 mmol) were added and the reaction mixture was stirred at room temperature in the dark for 2 hours. The reaction mixture was diluted with 200 mL dichloromethane and washed with 3×100 mL water. The organic layer was evaporated under vacuum and purified by column chromatography using hexane:ethyl acetate solvent mixture to yield desired product (92 mg, 57%).

Synthesis of Methyl 7-(4-((4-(dimethylamino)phenyl)diazenyl)benzamido)heptanoate (15b)

Compound 15b was synthesized following the above mentioned procedure where 4-((4-(dimethylamino)phenyl)diazenyl)benzoic acid (0.12 g, 0.45 mmol) and methyl 7-aminoheptanoate (0.071 g, 0.446 mmol) were used to the desired product (0.10 g, 55%).

Synthesis of N-(7-(hydroxyamino)-7-oxoheptyl)-4-(phenyldiazenyl)benzamide (16a)

Methyl ester 15a (0.092 g, 0.25 mmol) was suspended in a 4 mL of 1:1 (v/v) mixture of methanol and 50% hydroxylamine (aq). To this suspension was added 2 N NaOH(aq) (1.0 mL). After 2 hours the mixture had become homogeneous. Then 2 N HCl was added, bringing the solution back to a neutral pH, upon which the product precipitated from solution. Filtration of the solid afforded the product 16a (0.071 g, 77%).

Synthesis of 4-((4-(dimethylamino)phenyl)diazenyl)-N-(7-(hydroxyamino)-7-oxoheptyl)benzamide (16b)

Intermediate compound 15b (0.10 g, 0.24 mmol) was used to make the final compound 16b (0.073 g, 72.8%) using the same procedure followed to make 16a.

Synthesis of methyl 8-oxo-8-((4-(phenyldiazenyl)phenyl)amino)octanoate (18a)

4-(phenyldiazenyl)aniline hydrochloride 17a (0.15 g, 0.64 mmol) and triethylamine (268 μL, 1.93 mmol) were dissolved in DCM (10 mL) and cooled to 0° C. To this solution was added methyl 8-chloro-8-oxooctanoate (109 μL, 0.77 mmol). After 1 hour the mixture was diluted with DCM (50 mL) and then washed with H₂O (50 mL), brine (50 mL) and then dried with magnesium sulfate. Purification by column chromatography (silica gel, DCM/EtOAc 50%) gave product 18a (0.199 g, 84%).

Synthesis of $N^1$-hydroxy-$N^8$-(4-(phenyldiazenyl)phenyl)octanediamide (19a)

Compound 19a was synthesized using the same procedure that was followed to make 16a where methyl 8-oxo-8-((4-(phenyldiazenyl)phenyl)amino)octanoate (18a, 0.192 g, 0.522 mmol) was used to get the final compound 19a (0.112 g, 58.2%).

Synthesis of Methyl 8-((4-((4-(dimethylamino)phenyl)diazenyl)phenyl)amino)-8-oxooctanoate (18b)

Compound 18b was made following the amidation reaction that was followed to make 18a. 4-((4-aminophenyl)diazenyl)-N,N-dimethylaniline 17b (0.15 g, 0.624 mmol) and triethylamine (174 μL, 1.24 mmol) were dissolved in DCM (10 mL) and cooled to 0° C. To this solution was added methyl 8-chloro-8-oxooctanoate (133 μL, 0.93 mmol). After 1 hour the mixture was diluted with DCM (50 mL) and then washed with H₂O (50 mL), brine (50 mL) and then dried with magnesium sulfate. Purification by column chromatography (silica gel, DCM/EtOAc 50%) gave product 18b (0.235 gm, 92%).

Synthesis of $N^1$-(4-((4-(dimethylamino)phenyl)diazenyl)phenyl)-$N^8$-hydroxyoctanediamide (19b)

The final compound 19b was synthesized by using the same procedure that described to make 18a where 18b (0.227 g, 0.553 mmol) was used as starting material to make the final desired compound (0.17 g, 74.5%).

Example 5—Preparation of Compounds

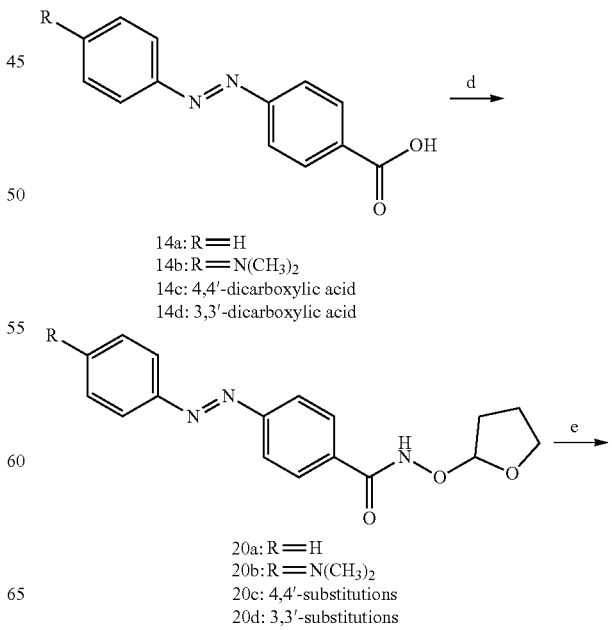

Scheme: 7

14a: R = H
14b: R = N(CH₃)₂
14c: 4,4'-dicarboxylic acid
14d: 3,3'-dicarboxylic acid 20a: R = H
20b: R = N(CH₃)₂
20c: 4,4'-substitutions
20d: 3,3'-substitutions

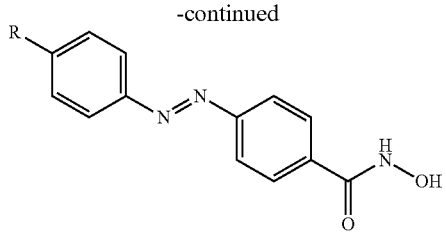

21a: R═H
21b: R═N(CH$_3$)$_2$
21c: 4,4'-substitutions
21d: 3,3'-substitutions

Reagents and conditions: (d). o-THP-hydroxyl amine, PyBOP, DIPEA (N, N'-diisopropylethyldiamine), CH$_2$Cl$_2$, 1 h, RT. (e), TFA:CH$_2$Cl$_2$ (1:1), room temp, 30 min General Procedure: Amide Coupling of Azophenyl-Benzoic Acid and THP Protected Hydroxyl Amine (A) and Deprotection to Get the Corresponding Final Compounds (B):

Phenyl azobenzoic acid (1 eq) and O-(tetrahydro-2H-pyran-2-yl)hydroxylamine (1.2 eq) were suspended in dichloromethane. PyBOP (benzotriazol-1-yl-oxytripyrrolidinophosphonium hexafluorophosphate) and DIPEA (N,N'-diisopropylethyldiamine) (1.2 eq each) were added into the reaction mixture. The reaction was continued with stirring at room temperature for overnight. Dichloromethane 4× volume was added to the reaction vessel to dilute and washed with water. All organic fractions were combined and evaporated under vacuum. The concentrate was purified by column chromatography with dichloromethane:methanol:triethyl amine (95:4:1) solvent system to purify the compounds. The intermediate synthesized compounds were subjected to deprotection in a 50:50 mixture of dichloromethane (DCM) and trifluoroacetic acid (TFA). The deprotection reaction was carried out by stirring the purified protected hydroxyl compounds in DCM/TFA (10 mL for 100 mg compound) at room temperature for 30 minutes. The reaction mixture was evaporated under vacuum and sticky brown mass was suspended in ethyl acetate, washed with saturated sodium bicarbonate solution. Evaporation of organic layer gave the sufficiently pure final compounds.

Synthesis of N-hydroxy-4-(phenyldiazenyl)benzamide (21a)

Compound 20a was synthesized following the general procedure (A) described above. In that procedure 4-(phenyldiazenyl)benzoic acid (0.10 g, 0.442 mmol) was treated with O-(tetrahydro-2H-pyran-2-yl)hydroxylamine (0.062 g, 0.53 mmol) to get the desired compound 20a (0.098 g, 68%) which was then exposed to THP-deprotection reaction (B) described above to get the final compound 21a (0.068 g, 93.6%).

Synthesis of 4-((4-(dimethylamino)phenyl)diazenyl)-N-hydroxybenzamide (21b)

The intermediate compound 20b was synthesized following the described procedure (A). 4-((4-(dimethylamino)phenyl)diazenyl)benzoic acid (0.15 g, 0.557 mmol) was treated with O-(tetrahydro-2H-pyran-2-yl)hydroxylamine (0.065 g, 0.557 mmol) to get the desired product 20b (0131 g, 64%) and deprotection of which gave the desired final compound 21b (0.016 g, 16%).

Synthesis of 4-((4-(hydroxycarbamoyl)phenyl)diazenyl)benzoic Acid (21c)

Compound 20c was made using the general procedure (A) described above. There 4,4'-(diazene-1,2-diyl)dibenzoic acid (0.15 g, 0.555 mmol) and O-(tetrahydro-2H-pyran-2-yl)hydroxylamine (0.065 g, 0.555 mmol) were used to get 20c (0.063 g, 31%) and that was exposed to the deprotection condition to get the final compound 21c (0.0305 g, 62.7%).

Synthesis of 3-((3-(hydroxycarbamoyl)phenyl)diazenyl)benzoic Acid (21d)

Compound 20d was made using the general procedure (A) described above. There 3,3'-(diazene-1,2-diyl)dibenzoic acid (0.15 g, 0.555 mmol) and O-(tetrahydro-2H-pyran-2-yl)hydroxylamine (0.065 g, 0.555 mmol) were used to get 20d (0.077 g, 37.5%) and that was exposed to the deprotection condition to get the final compound 21d (0.023 g, 38.7%).

Example 6—Preparation of (E)-N-(2-(2-((4-((4-((2-aminophenyl)carbamoyl)phenyl)diazenyl)phenyl)(methyl)amino)ethoxy)ethyl)-11-oxo-2,3,5,6,7,11-hexahydro-1H-pyrano[2,3-f]pyrido[3,2,1-ij]quinoline-10-carboxamide (SAS130)

To a solution of BG68 (0.0115 mmol, 1 eq.)

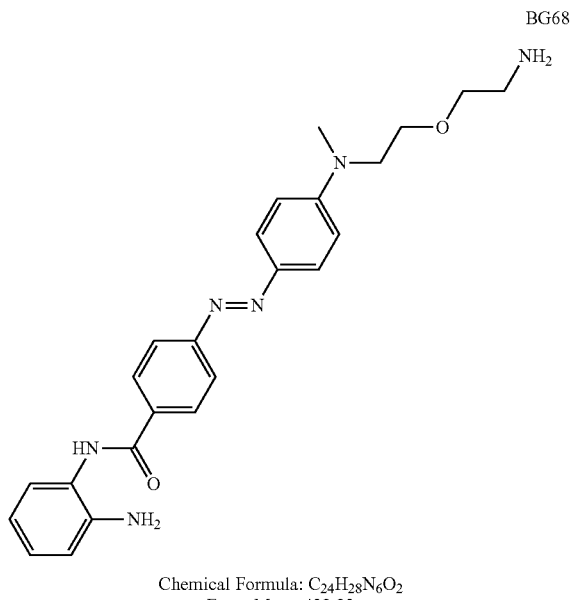

BG68

Chemical Formula: C$_{24}$H$_{28}$N$_6$O$_2$
Exact Mass: 432.23
Molecular Weight: 432.52 in DCM (2 mL), DIPEA (3 eq.) was added, followed by Coumarin 343 (1 eq.) and PYBOP (1.1 eq.). The reaction mixture was stirred for 30 minutes at room temperature. After completion of the reaction, as monitored by LC/MS, the solvent was removed. The crude product was purified via flash chromatography (100% DCM→10:1 DCM: MeOH) yielding a dark orange solid (3.2 mg, 0.0045 mmol, 39%). $^1$H NMR (400 MHz, Chloroform-d) δ 8.57 (s, 1H), 8.0 (d, J=8.29 Hz, 2H), 7.89 (d, J=8.55 Hz, 2H), 7.86 (d, J=9.13 Hz, 2H), 7.38 (d, J=7.95 Hz, 1H), 7.14-7.08 (m, 1H), 6.98 (s, 1H), 6.90-6.94 (m, 2H), 6.78 (d, J=9.18 Hz, 2H), 3.90 (brs, 1H-NH), 3.70 (dd, J=4.37; 10.76 Hz, 4H), 3.63 (d, J=2.44 Hz, 4H), 3.34-3.29 (m, 4H), 3.16 (s, 3H), 2.89 (t, J=6.42 Hz, 2H), 2.75 (t, J=6.14 Hz, 2H), 2.01-1.92 (m, 4H). LC/MS: $C_{40}H_{41}N_7O_5$ Exact mass: 699.32; ES−[M]⁻ Found: 698.02; ES+[M]⁺ Found: 700.18.

Example 7—Inhibitor Characterization and Biochemical Profiling

Physical characterization of the prototype inhibitors in PBS confirmed that all compounds strongly absorb light in the blue spectrum with maximum absorbance around 470 nm.

Figure 13A:
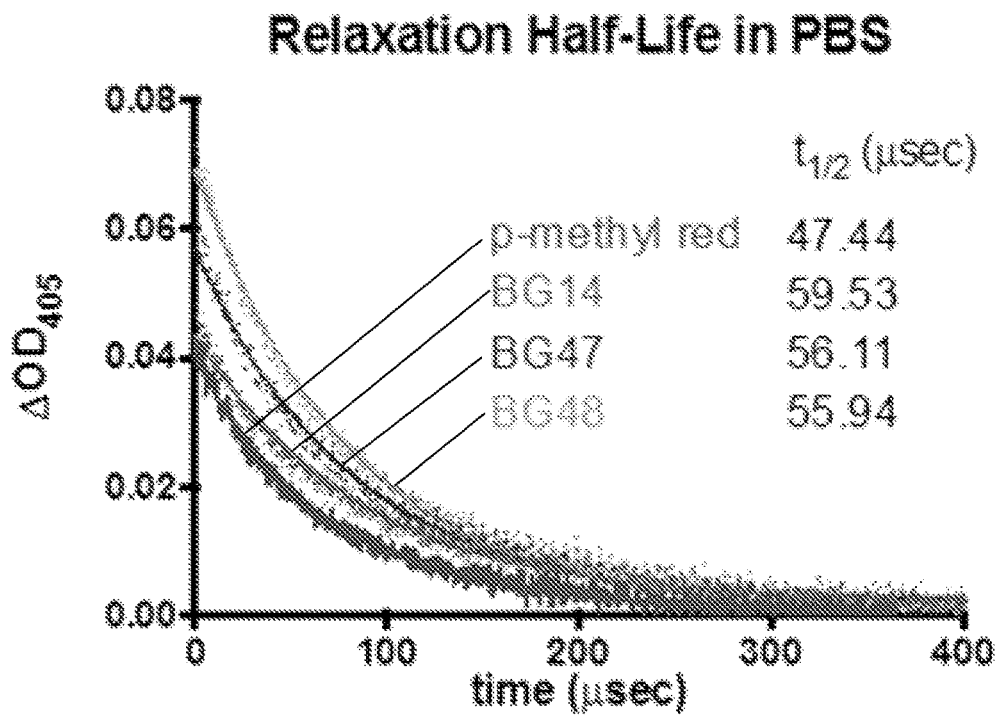
FIGS. 13A-13F provide (FIG. 13A) measurement of thermal relaxation half-life, (FIG. 13B) the LED array, (FIG. 13C) light intensity and concentration dependent inhibition of HDAC3 by BG14, and (FIGS. 13D-13F) light-dependent activity profiles of the tested compounds against HDAC1-3.

Thermal relaxation half-lives of push-pull azobenzene analogs similar to the presented compounds in aqueous solution at physiological pH have not been reported. Previous approaches to study fast cis-to-trans isomerization are based on laser flash photolysis to measure the transient absorbance change following excitation with a short laser pulse. Such experimental setups offer picosecond resolution, however, are very expensive and not commonly accessible. A readily adaptable instrumentation setup was designed to measure relaxation kinetics with microsecond resolution. Using this approach the thermal relaxation half-lives of the studied HDAC ligands were found to range from 55-60 μs, relative to 47 μs for 4-((4-(dimethylamino)phenyl)azo)benzoic acid (DABCYL), which is approximately 120× faster than previous measurements for DABCYL in chloroform (FIG. 13A). The estimate distance of diffusion of small molecules (diffusion coefficient D=10-6-10-7 cm²/s) at 10×T1/2 (500 μs) in water is 0.1-0.3 μm, limiting diffusion of "activated" inhibitors well within subcellular dimensions.

Figure 13B:
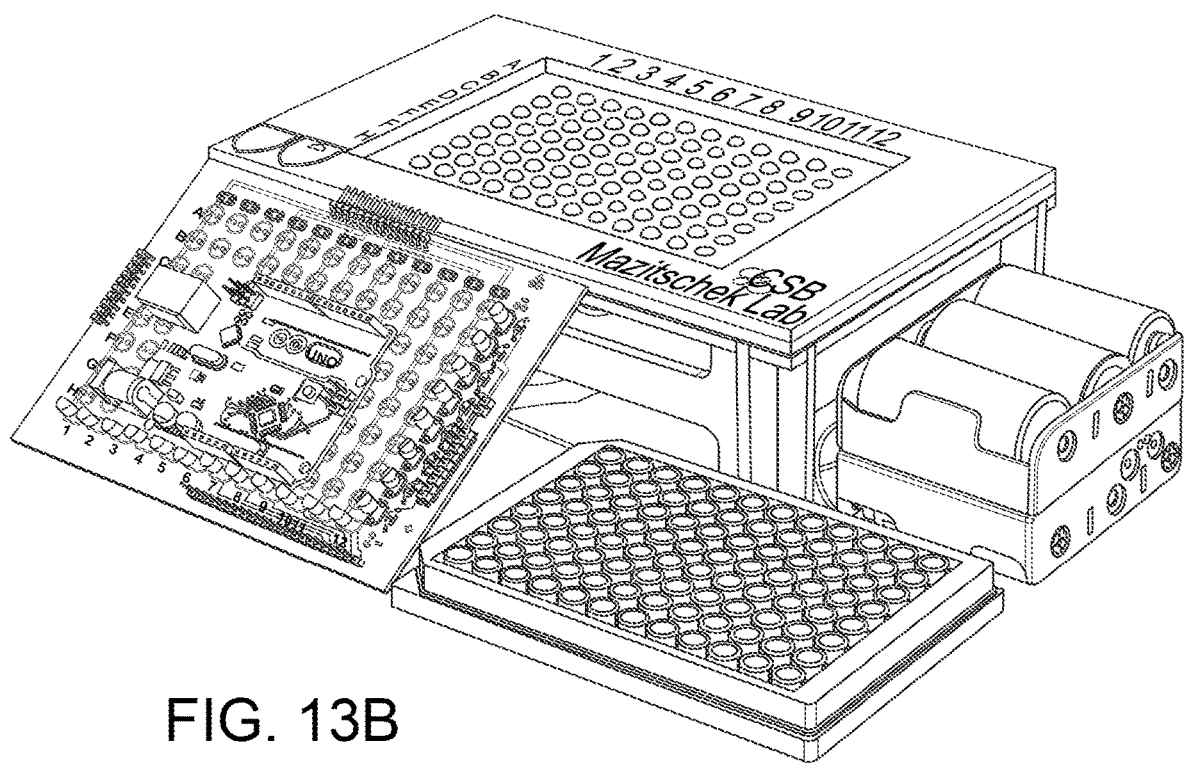
Figure 13C:
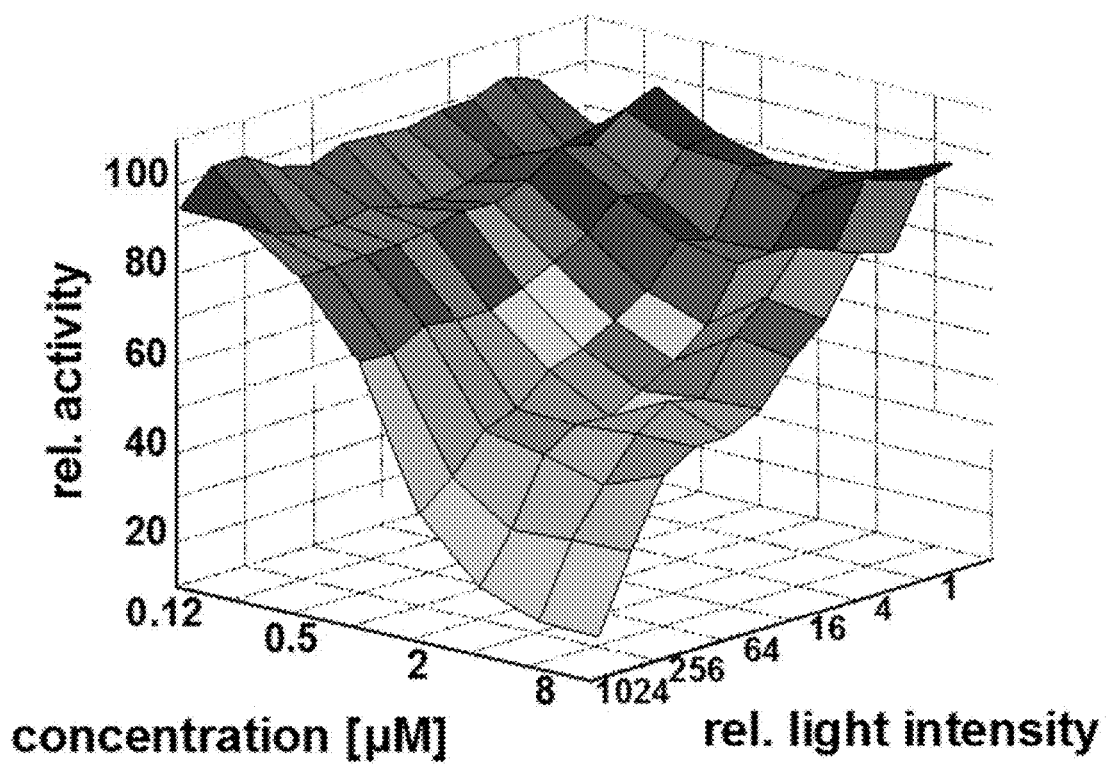
Figure 13D:
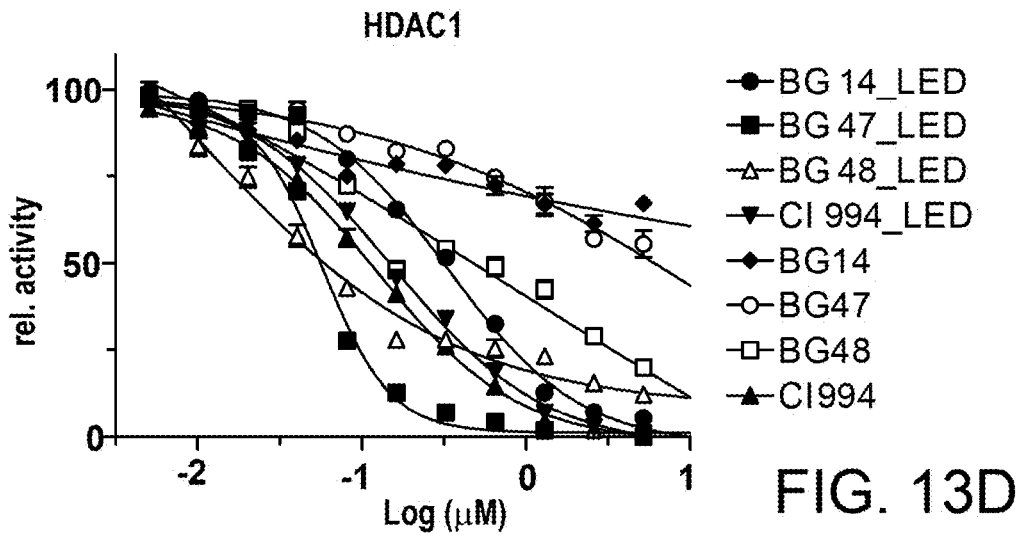
Figure 13E:
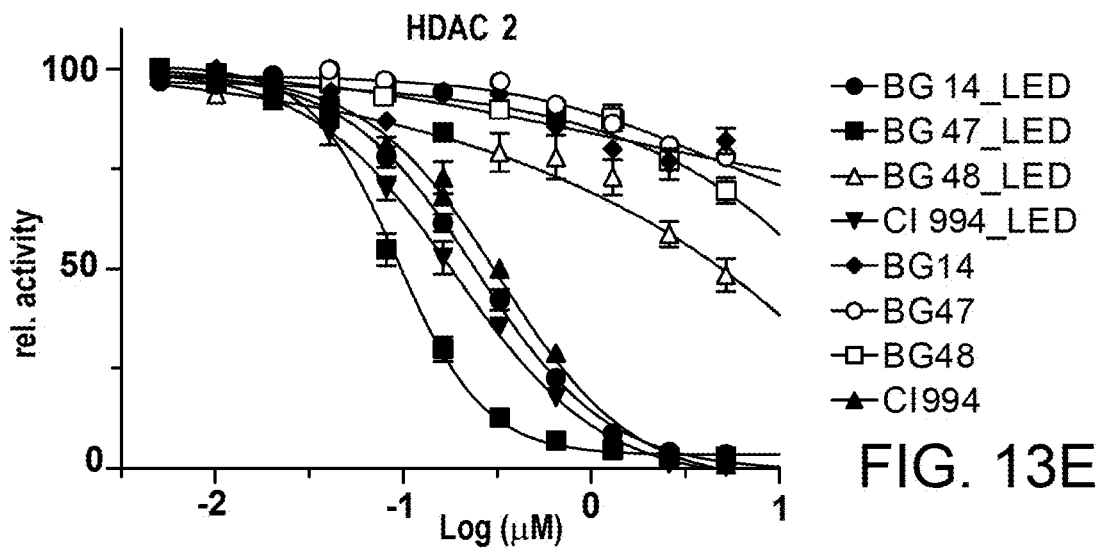
Figure 13F:
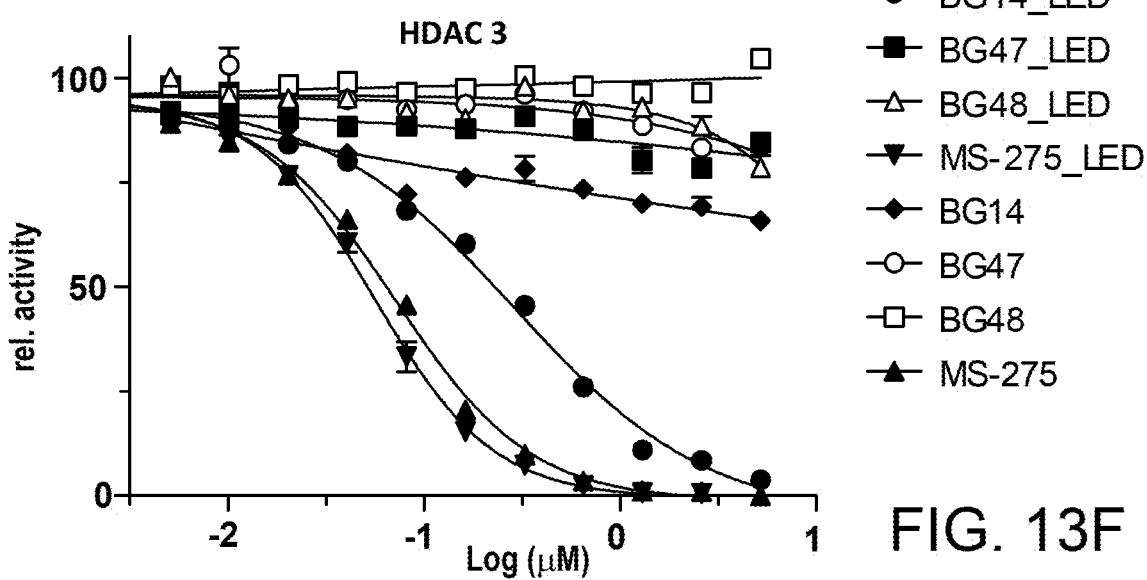

To allow for high-throughput profiling of biochemical and cellular activity a microprocessor-controlled (using the open-source Arduino platform) 12×8 LED-arrays that are compatible with 96-well microtiter plates was developed (As described above and further detailed in FIG. 13B).

Using the LEDs array the light dependent HADC inhibitory activity of the reported compounds was accurately profiled. As shown in FIG. 13C-F, following light exposure all compounds strongly inhibited HDAC3 enzymatic activity in a biochemical assay using an artificial acetyl-lysine tripeptide based on acH4K12, while no differential activity was observed for the reference HDAC inhibitor CI-994. Profiling of the inhibitor set against HDAC3 revealed that only BG14 showed potent light-dependent inhibitory activity. In contrast, and as predicted for 4-aryl substituted benzamide HDAC inhibitors, BG47 and BG48 did not inhibit HDAC3 in the presence and absence of light, which validates that the inhibitory activity is not the result non-specific inhibition. Furthermore, as shown for BG14 and HDAC3, the inhibitory activity is directly proportional to the average light exposure, demonstrating that the inhibitory potency can be directly controlled by light exposure.

Example 8—Inhibitor In Vitro Profiling

Figure 14D:
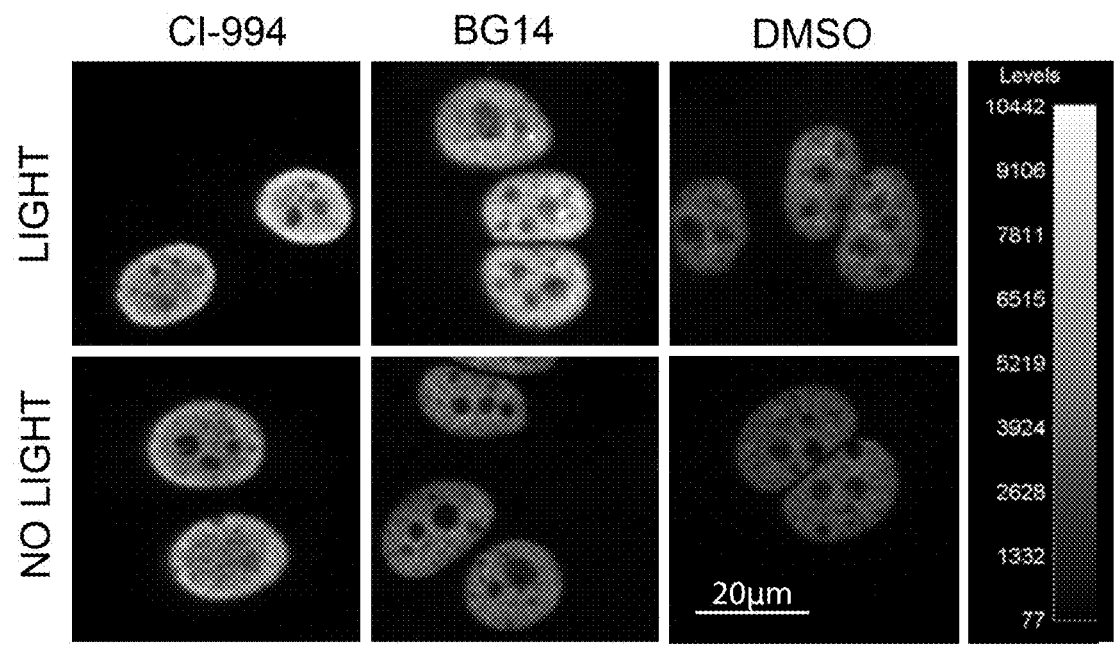
Figure 14E:
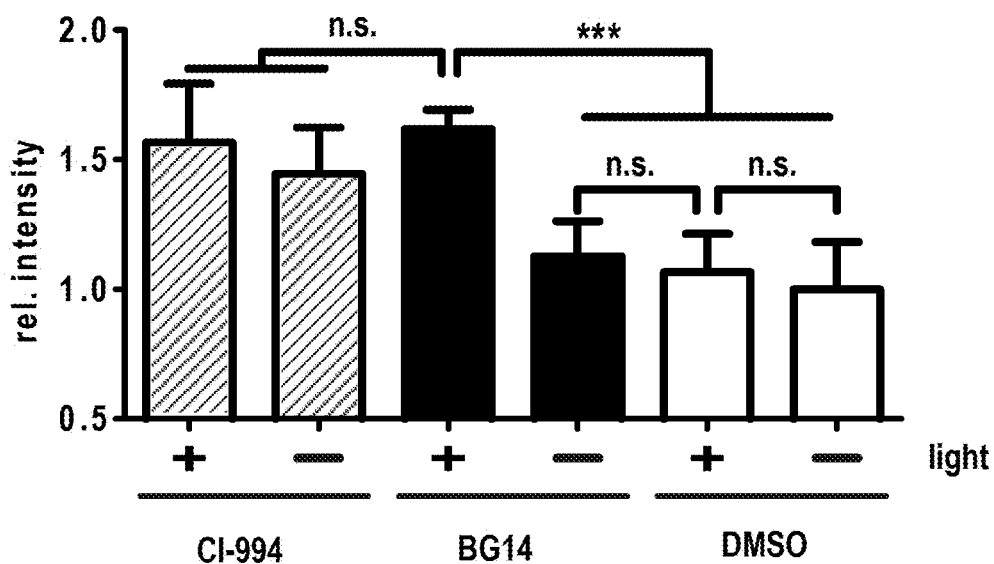

BG14, BG47 and BG48 were profiled in cell culture to assess cellular activity using acetylation of histone H3 Lysine 9 (H3K9Ac) as a pharmacodynamic marker for HDAC inhibition. As shown in FIG. 14, compound treatment of MCF7 cells in the presence of light strongly induced acetylation of H3K9 relative to the vehicle control. H3K9 acetylation levels directly correlated with light exposure. No significant histone acetylation above background was observed in the absence of light. As expected, BG14, which also inhibits HDAC3, induced the strongest increase of H3K9 acetylation compared to the HDAC1/2-selective inhibitors BG47 and BG48.

Example 9—Expression Profiling

In order to gain more quantitative insights into the specific genes regulated by the presented inhibitors, and to provide further evidence that the BG inhibitors elicit biological responses similar to the closely related, but light-independent HDAC inhibitors a high-throughput gene expression analysis was performed. Expression profiling was performed in quadruplicate using the L1000™ platform (Genometry, Inc.). Specifically MCF7 cells were treated with various compounds and the transcriptional changes were measured as a function of compound concentration, light exposure intensity, and treatment duration relative to the reference HDAC inhibitors CI994 and "Merck60".

Gene Set Enrichment Analysis (GSEA) comparing the expression patterns of the BG inhibitors with the reference inhibitors demonstrated a high correlation between the respective expression profiles under light treatment conditions, establishing strong support for similar biological activity (FIG. 4B for BG14 and SI figures for BG47, BG48).

Interestingly, a lower but significant correlation was observed between photochromic and reference HDAC inhibitors in the absence of light. Given the low affinity of the BG compounds for HDACs and the absence of measurable increase of histone acetylation at the tested concentrations suggests that transcriptional changes are possibly caused by off-target effects that are common to the tested inhibitors, which all share high chemical similarity.

Polypharmcology (DOI: 10.1021/jm400856t) of small molecules is well recognized and inhibition of unintended/unknown targets can contribute to the global biological response. Unintended inhibition of secondary targets can complicate Chemical Genetics approaches using small molecules to dissect protein function. Commonly accepted approaches rely on comparative normalization to "inactive" analogs that establish a background signature. In this context, photochromic ligands offer a significant advantage as they allow one to compare active and inactive states for a specific protein using the same chemical entity rather than comparing two distinct molecules with sometimes significantly different physical and chemical properties.

Figure 15A:
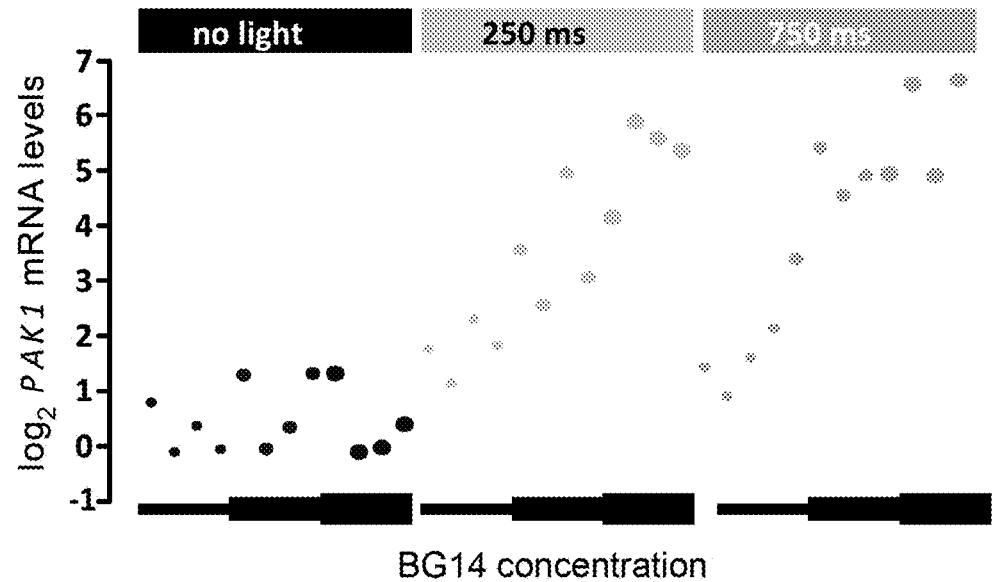
Figure 15B:
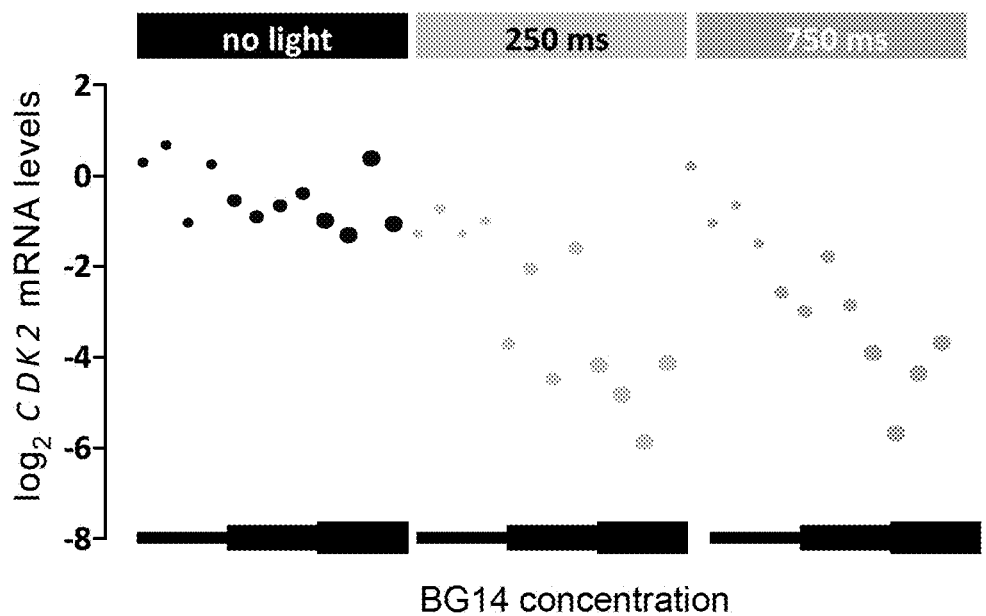
Figure 15C:
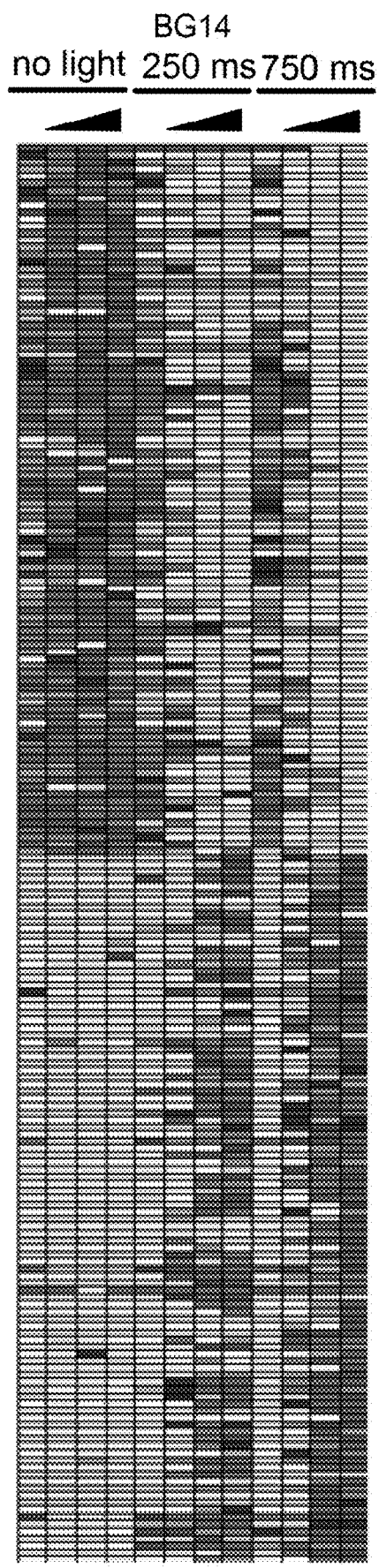

Following this approach, subsets of transcripts that are only differentially expressed in the presence of both light and inhibitor were identified. The relative expression changes directly correlated with average light exposure intensity and inhibitor concentration (see FIG. 15C,D). Importantly, light or inhibitor treatment alone does not induce significant change in the respective transcript levels.

As shown in FIG. 15, a L1000 platform was used to evaluate gene signatures in response to BG14 treatment under different light exposure conditions in MCF7 cell lines. In the absence of light, the vast majority of landmark genes on the L1000 did not show any significant changes in transcript levels. However, increasing amounts of light resulted in significant changes of expression levels of specific landmark genes, such as PAK1mRNA (FIG. 15A) and the cell division gene CDK2 (FIG. 15B), indicating that BG14-cis to BG14-trans transformation successfully occurred in MCF7 cells and is a prerequisite for its activity. To verify the light-dependent nature of BG14's activity, the top 100 up and top 100 downregulated transcripts (both landmark and inferred genes) were identified. Very strikingly, the relative heatmap (FIG. 15C) depicts very little change in transcript levels in absence of light, irrespective of compound concentration, while with increasing amounts of light both a light-dose and concentration-dependent change in expression levels was observed, thus suggesting that light-dependent control of BG14 activity holds true for a large number of genes.

Figure 15D:
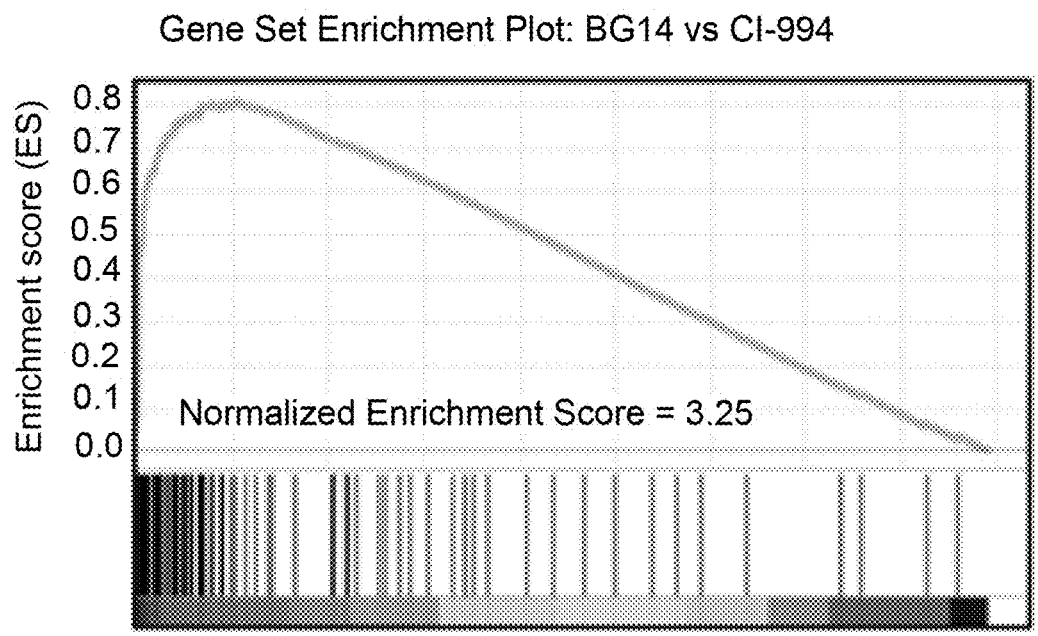
Figure 15E:
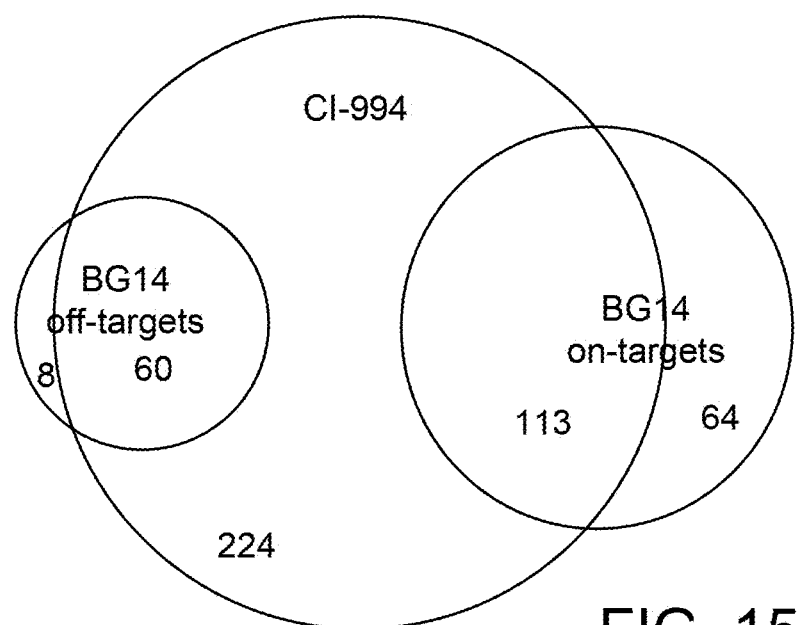

To assess BG14's nature as an HDAC inhibitor beyond its ability to modulate HDAC and histone acetylation levels, Gene Set Enrichment Analysis (GSEA) was performed between BG14 (max concentration, max amount of light) and the known HDAC inhibitor CI-994 (the same concentration) (FIG. 15D). Very remarkably, the Normalized Enrichment Score (NES) of 3.25 indicates a very high degree of similarity between both expression profiles. The identified 177 On-Target Gene List, (landmark genes regulated by light-dependent BG14_trans only), as well as the 68 Off-Target list (landmark genes regulated in absence of light by BG14_cis) were compared to the list of genes regulated by CI-994. 64% of the On-Target genes overlap with CI-994's gene list (FIG. 15E). Genemania-derived network and pathway analysis was performed on the 'Core Gene Set' and multiple significant networks were identified. All identified significant features/networks are related to aspects of cell cycle and mitochondrial regulation and function. Furthermore, the genes in the cell cycle and mitochondria networks consist of the top 25 downregulated genes were within the Core Gene set (FIG. 15F,G).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound selected from the group consisting of:

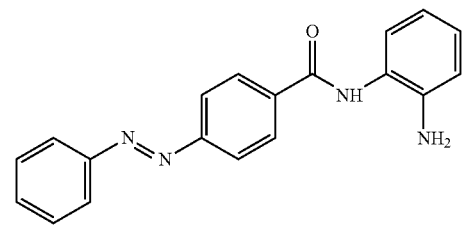

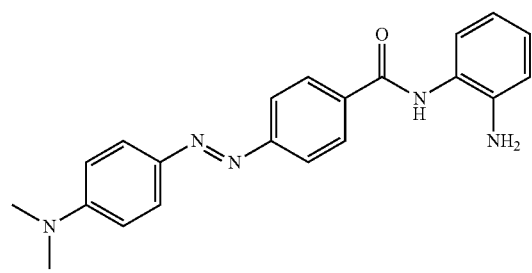

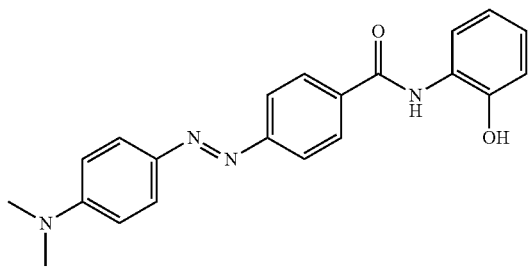

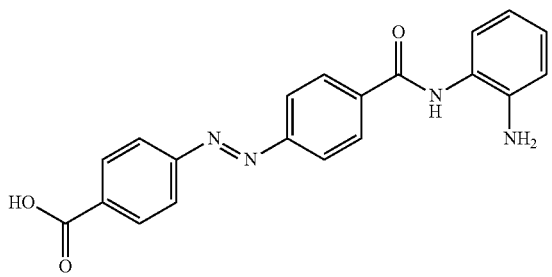

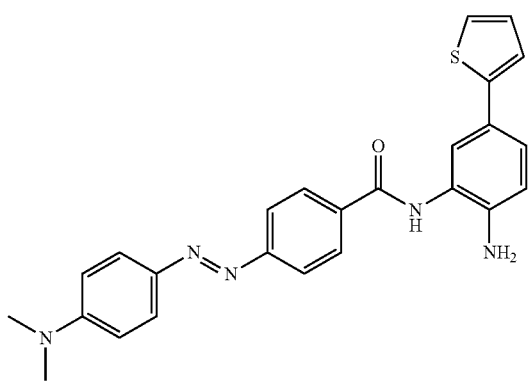

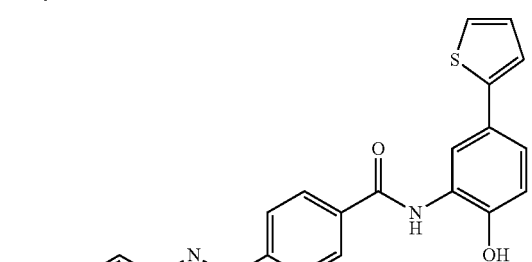

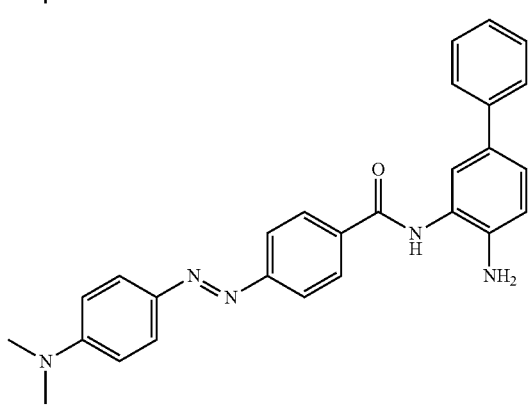

57
-continued
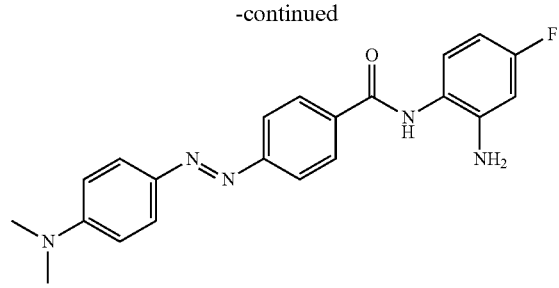
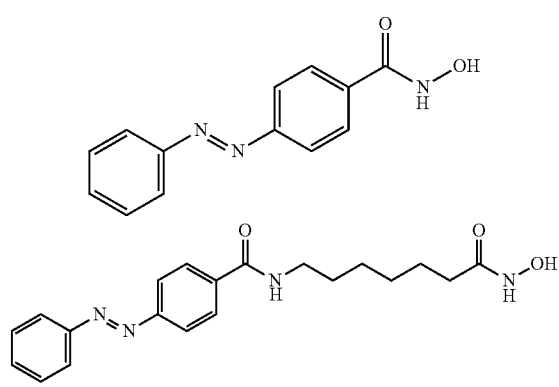
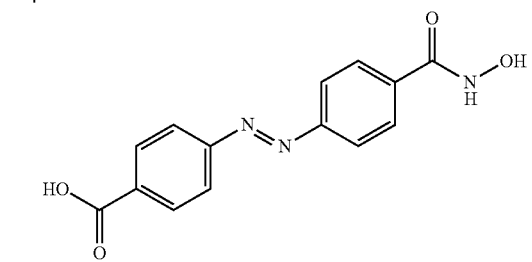
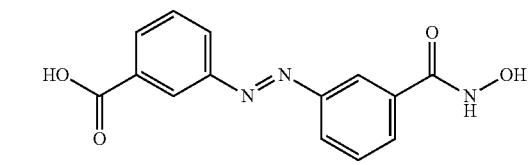
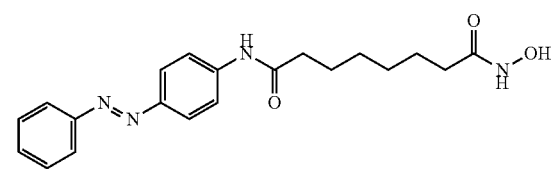
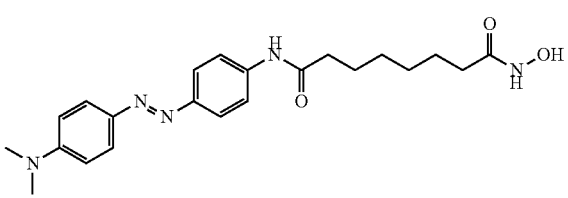
58
-continued
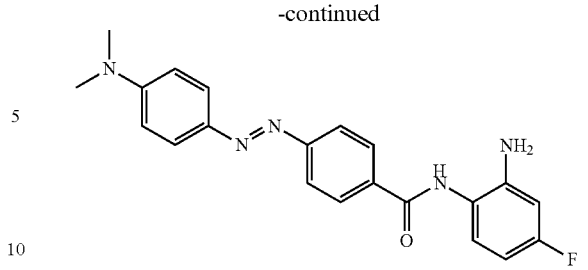
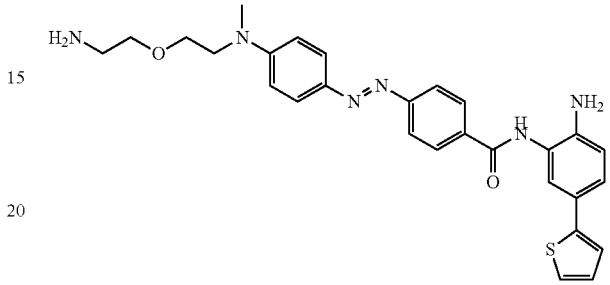
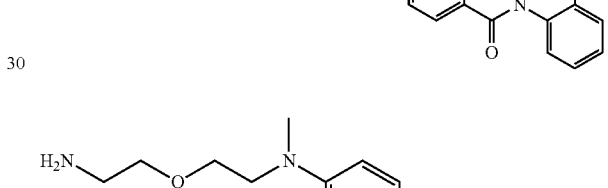
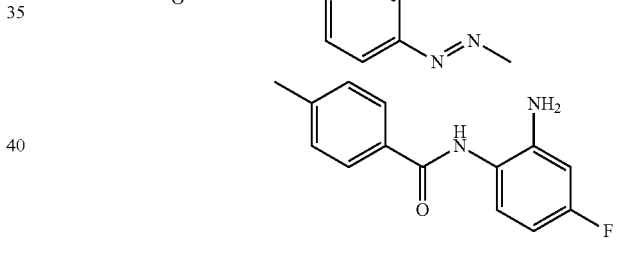
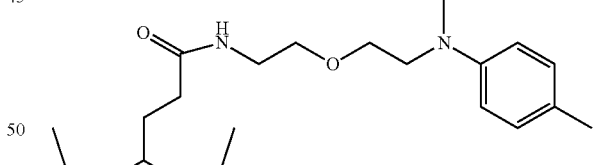
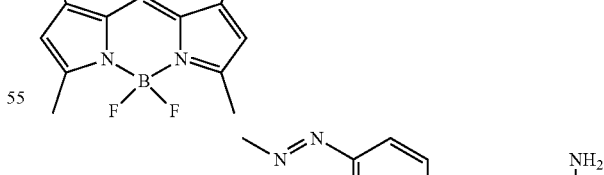

-continued
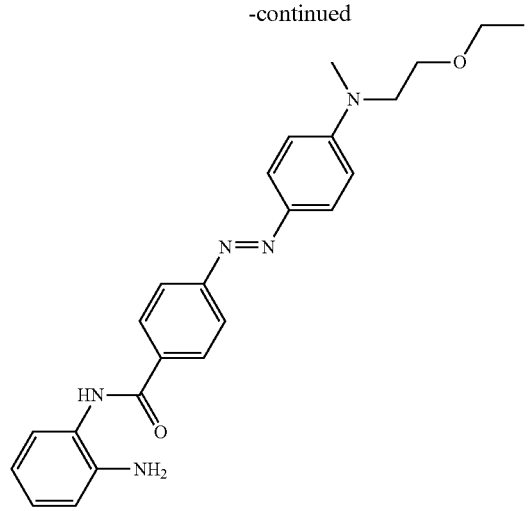
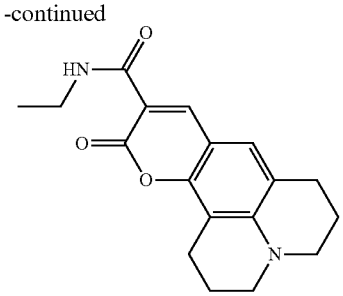
or a pharmaceutically acceptable salt form thereof.
2. A compound selected from any one of the following compounds:
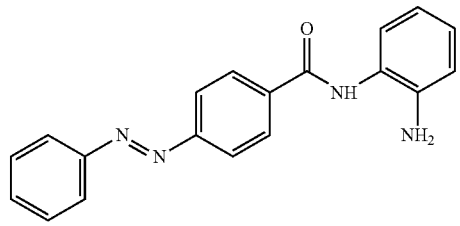
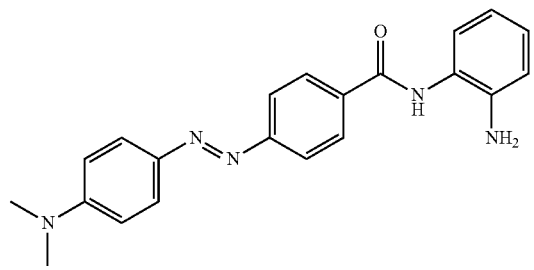
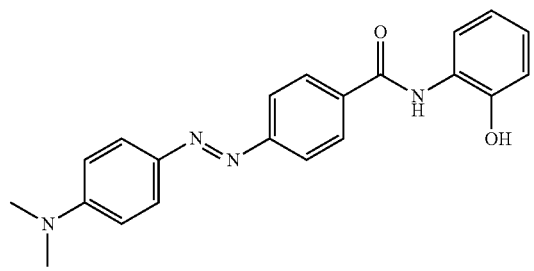
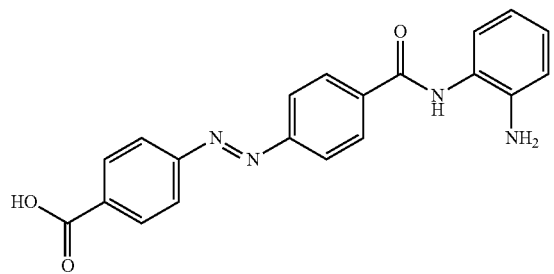

-continued
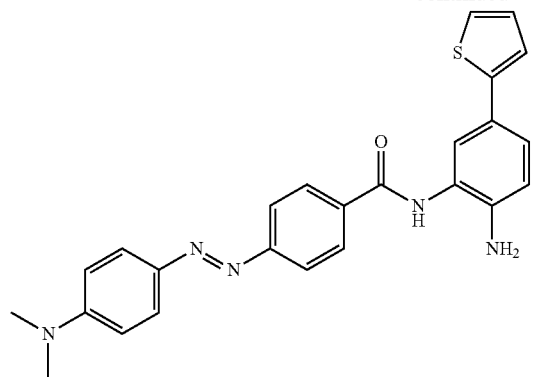
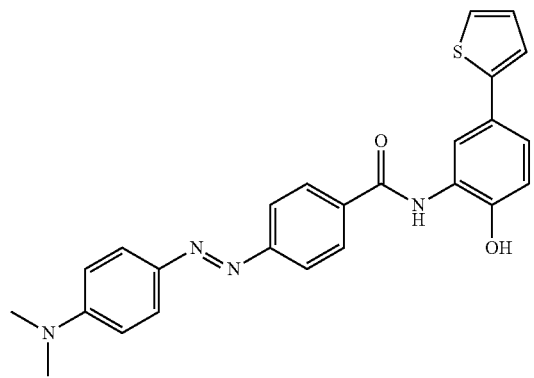
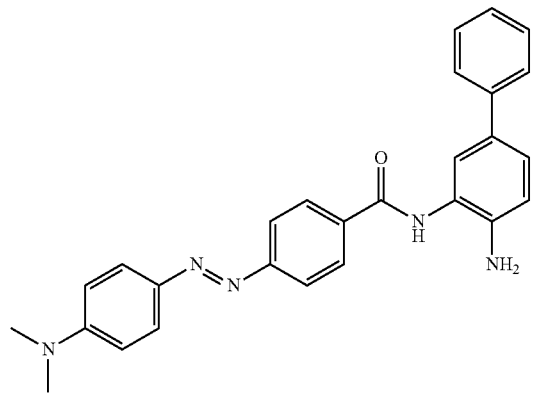
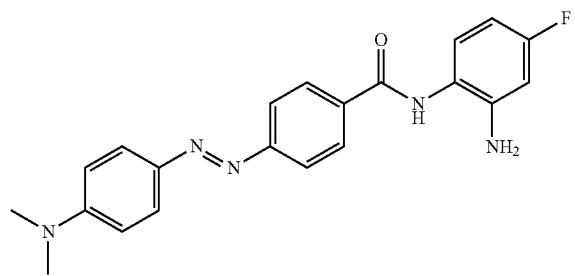

-continued
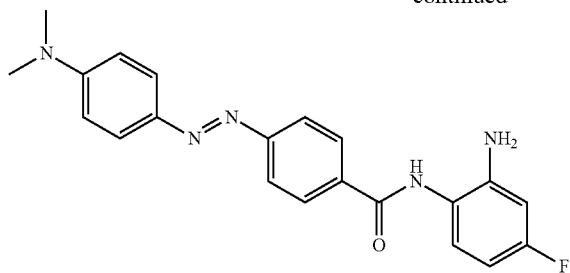
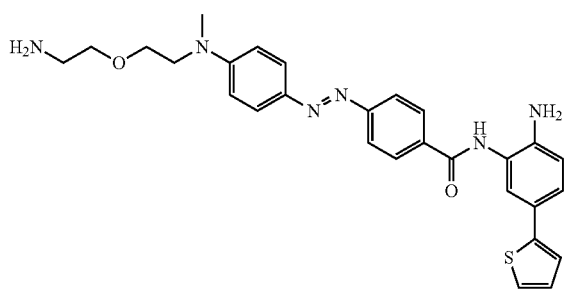
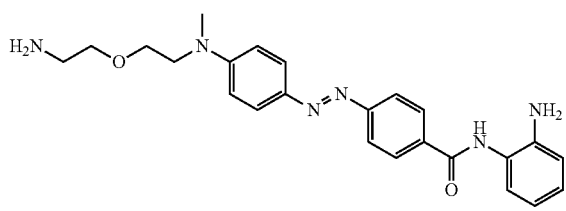
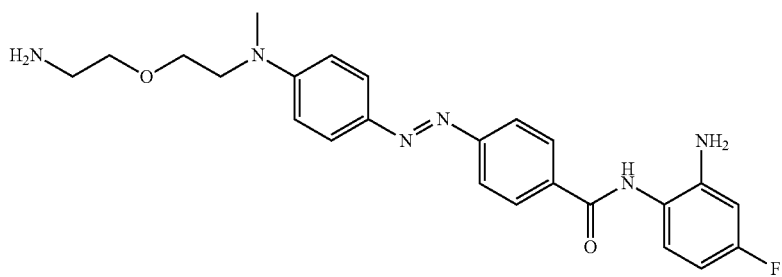
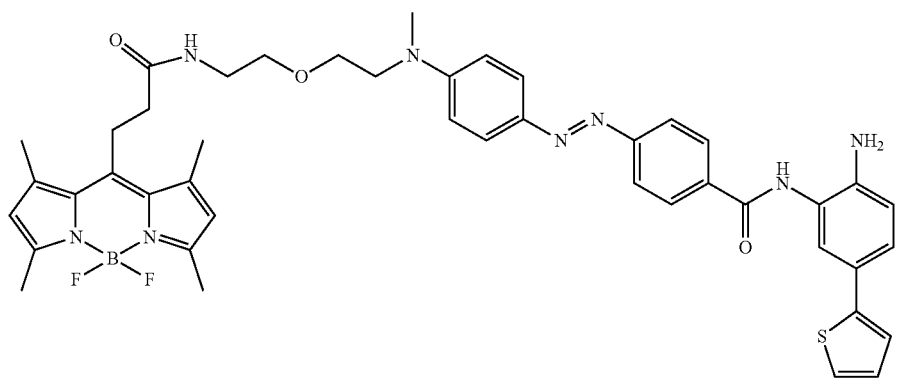

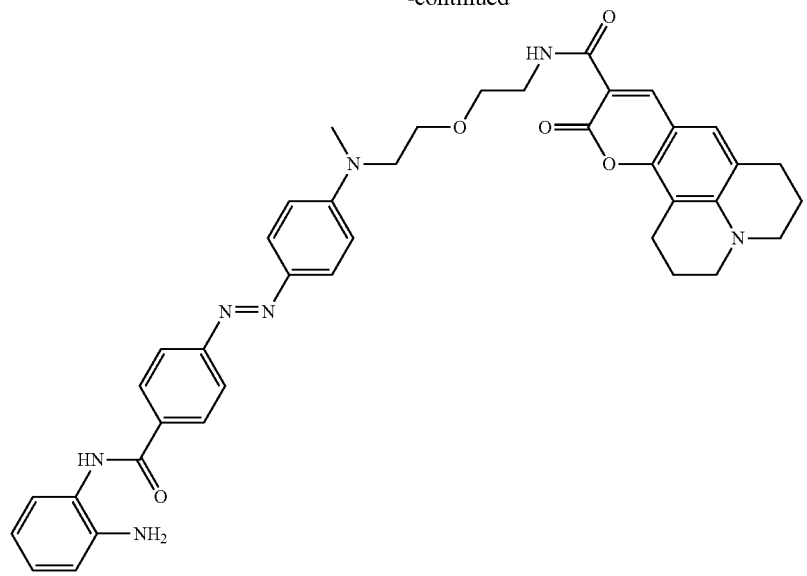
or a pharmaceutically acceptable salt thereof.
3. A compound selected from:
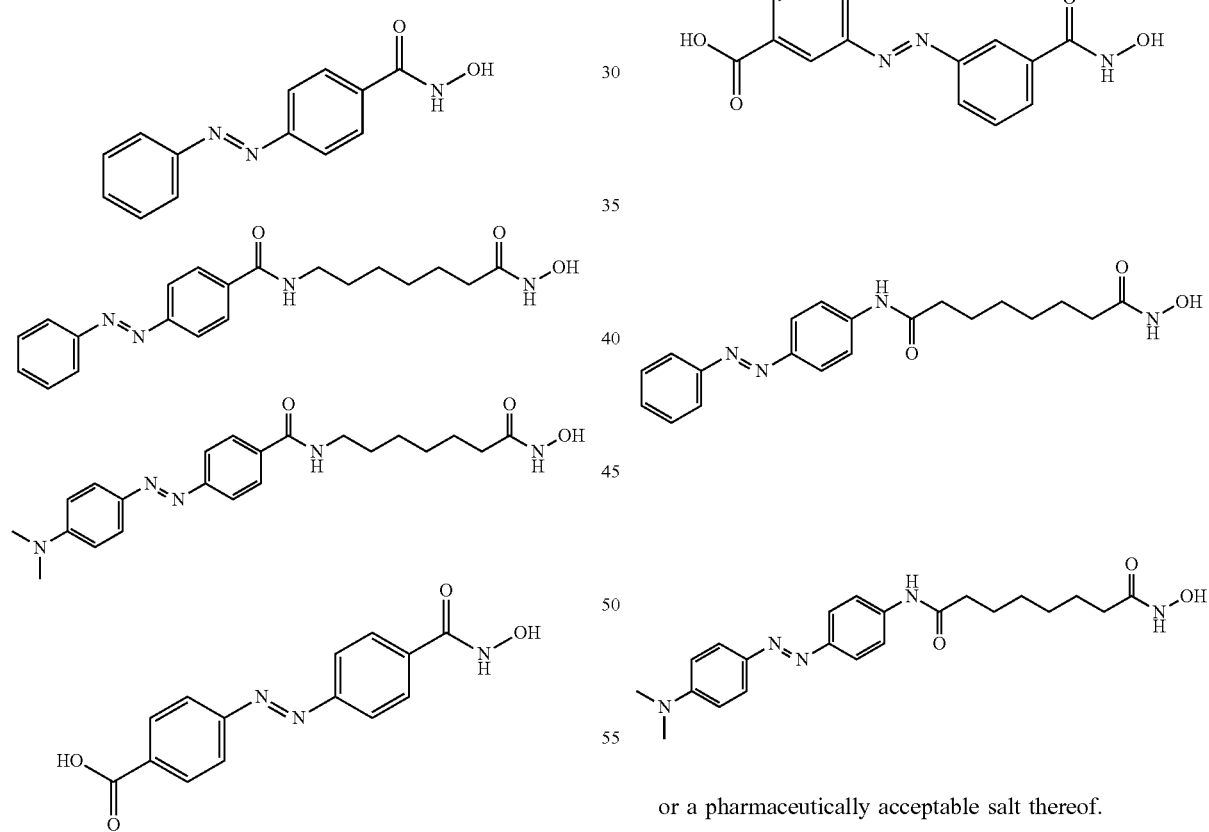
or a pharmaceutically acceptable salt thereof.
* * * * *